(12) United States Patent
Jung et al.

(10) Patent No.: US 9,403,831 B2
(45) Date of Patent: Aug. 2, 2016

(54) TRIAZOLOPYRAZINE DERIVATIVE AND USE THEREOF

(71) Applicants: KOREA RESEARCH INSTITUTE OF CHEMICAL TECHNOLOGY, Daejeon (KR); HANDOK INC., Seoul (KR)

(72) Inventors: Hee Jung Jung, Daejeon (KR); Jae Du Ha, Daejeon (KR); Sung Yun Cho, Daejeon (KR); Hyoung Rae Kim, Daejeon (KR); Kwang Ho Lee, Daejeon (KR); Chong Ock Lee, Seoul (KR); Sang Un Choi, Daejeon (KR); Chi Hoon Park, Daejeon (KR)

(73) Assignees: KOREA RESEARCH INSTITUTE OF CHEMICAL TECHNOLOGY, Daejeon (KR); HANDOK INC., Seoul (KR)

( * ) Notice: Subject to any disclaimer, the term of this patent is extended or adjusted under 35 U.S.C. 154(b) by 0 days.

(21) Appl. No.: 14/435,974

(22) PCT Filed: Sep. 30, 2013

(86) PCT No.: PCT/KR2013/008740
§ 371 (c)(1),
(2) Date: Apr. 15, 2015

(87) PCT Pub. No.: WO2015/046653
PCT Pub. Date: Apr. 2, 2015

(65) Prior Publication Data
US 2015/0259350 A1    Sep. 17, 2015

(51) Int. Cl.
*C07D 487/04*    (2006.01)
*A61K 31/4985*   (2006.01)

(52) U.S. Cl.
CPC .......... *C07D 487/04* (2013.01); *A61K 31/4985* (2013.01)

(58) Field of Classification Search
None
See application file for complete search history.

(56) References Cited

U.S. PATENT DOCUMENTS 7,732,604 B2    6/2010   Cheng et al.

FOREIGN PATENT DOCUMENTS

| KR | 10-2012-0125261 A | 11/2012 |
| WO | WO-2011/079804 A1 | 7/2011 |

OTHER PUBLICATIONS

Hörig et al., J. Translational Med. 2:44 (2004).*
Cui et al., "Discovery of a novel class of exquisitely selective mesenchymal-epithelial transition factor (c-MET) protein kinase inhibitors and identification of the clinical candidate 2-(4-(1-(quinolin-6-ylmethyl)-1H-[1,2,3]triazolo[4,5-b]pyrazin-6-yl)-1H-pyrazol-1-yl)ethanol (PF-04217903) for the treatment of cancer," J Med Chem. 55(18):8091-109 (2012).
International Search Report for International Application No. PCT/KR2013/008740, dated Jun. 30, 2014 (7 pages) (English Translation Included).

* cited by examiner

*Primary Examiner* — Michael Barker
(74) *Attorney, Agent, or Firm* — Clark & Elbing LLP; Susan M. Michaud

(57) ABSTRACT

The present invention relates to a novel triazolopyrazine derivative or a pharmaceutically acceptable salt thereof, and a pharmaceutical composition containing the same as an active ingredient for preventing or treating hyper proliferative disorder. The present invention can be useful as a therapeutic agent for various hyper proliferative disorders associated with excessive cell proliferation and growth caused by abnormal kinase activity, such as cancer, psoriasis, rheumatoid arthritis, and diabetic retinopathy, by efficiently inhibiting c-Met tyrosine kinase activity.

16 Claims, No Drawings

TRIAZOLOPYRAZINE DERIVATIVE AND USE THEREOF

TECHNICAL FIELD

The present invention relates to novel triazolopyrazine derivatives having tyrosin kinase inhibitory activity and a pharmaceutical composition containing the same as an active ingredient for preventing and treating various hyper proliferative disorders.

BACKGROUND ART

Protein kinases (PKs) are enzymes that catalyze the phosphorylation of hydroxy groups on tyrosine, serine and threonine residues of proteins. The protein kinases play a key role in growth factor signaling inducing cell growth, differentiation, and proliferation, and thus activities of the protein kinases affect almost all aspects of cellular life.

Abnormal cell signaling pathways due to mutations or overexpressions of protein kinases are closely connected with stroma diseases including from diseases that are comparatively not life-threatening, like psoriasis, to toxic (pathogenic) diseases, like cancers.

Protein kinases may be classified into tyrosine kinases (TKs) and serine-threonine kinases (STKs).

One of the main aspects of tyrosine kinases is its involvement with growth factor receptors. Growth factor receptors are cell-surface proteins. When bound to growth factor ligands, the growth factor receptors are converted to active forms, which interact with proteins on the inner surface of cell membranes. This leads to the phosphorylation on tyrosine residues of the receptor and other proteins and to the formation of complexes with a variety of cytoplasmic signaling molecules inside the cell that, in turn, affect numerous cellular responses such as cell growth, differentiation, and proliferation and metabolic effects to the extracellular microenvironment, etc (Schleessinger and Ullrich, *Neuron.* 9: 303-391 (1992)).

Growth factor receptors with tyrosine kinase activity are known as receptor tyrosine kinases (RTKs). The receptor tyrosine kinases include a large family of trans-membrane receptors exhibiting diverse biological activities.

At present, at least 19 subfamilies of receptor tyrosine kinases have been identified, named "HER RTK" subfamily which includes epidermal growth factor receptor (EGFR), HER2, HER3, HER4, and the like. These receptor tyrosine kinases are composed of an extracellular glycosylated ligand binding domain, a transmembrane domain, and an intracellular cytoplasmic domain that can phosphorylate tyrosine residues on proteins.

Another receptor tyrosine kinase subfamily is composed of an insulin receptor (IR), an insulin-like growth factor I receptor (IGF-1R), and an insulin receptor related receptor (IRR). IR and IGF-1R interact with insulin, IGF-I, and IGF-II to form a heterotetramer of two completely extracellular-glycosylated α. subunits and two β subunits which cross the cell membrane and contain the tyrosine kinase domain.

Still another receptor tyrosine kinase subfamily is referred to as a platelet derived growth factor receptor (PDGFR) group, which includes PDGFRα, PDGFRβ, CSFIR, c-Kit, and c-Fms. These receptors are made up of glycosylated extracellular domains composed of variable numbers of immunoglobulin-like loops and an intracellular domain. A fetus liver kinase (Flk) receptor subfamily, which is included in the PDGFR group due to its similarity with the PDGFR subfamily, has been known. The Flk subfamily is composed of kinase insert domain-receptor fetal liver kinase-1 (KDR/Flk-1), Flk-1R, Flk-4, and Fms-like tyrosine kinase 1 or 3 (flt-1).

MET, which is a type of tyrosine kinase growth factor receptor family, is called c-Met, and has been considered to play a role in the primary canner growth and metastasis as a human hepatocyte growth factor receptor tyrosin kinase (hHGFR) (Plowman et al., *DN&P,* 7 (6):334-339(1994)).

In addition to the receptor tyrosine kinases (RTKs), there also exists a particular family of complete intracellular TKs called "non-receptor tyrosine kinases" or "cellular tyrosine kinases (CTK)". The non-receptor tyrosine kinases do not contain extracellular and trans-membrane domains, and are composed of Src, Frk, Btk, CskAbl, Zap70, Fes, Fak, Jak, and Ack subfamilies. Of these, the Src subfamily includes Src, Yes, Fyn, Lyn, Lck, Blk, Hck, Fgr, AUR1 (Aurora-B), AUR2 (Aurora-A), AUR3 (Aurora-C), Yrk, and the like (Bolen, *Oncogene.* 8: 2025-2031(1993)).

Pathogenic diseases associated with the receptor tyrosine kinases and non-receptor tyrosine kinases include psoriasis, hepatic cirrhosis, diabetes, angiogenesis, restenosis, ocular diseases, rheumatoid arthritis, autoimmune diseases, atherosclerosis, kidney troubles, and the like.

Of the PKs described above, receptor tyrosine kinases, such as Bcr-Abl, EGFR, and VEGFR, have been heavily studied as favorable anticancer drug targets, and anticancer drugs, such as Gleevec or Iressa, have been developed and marketed.

In addition, many anticancer drugs targeting c-Met (hepatocyte growth factor receptor, HGFR), which is a hepatocyte growth factor/scatter factor (HGF/SF) receptor in the RTKs that have been studied as anticancer drug targets, have been developed (J. G. Christensen, J. Burrows et al., Cancer Letters, 2005, 225, 1-26; WO 2004/076412; WO 2006/021881 A; WO 2006/021886; WO 2007/064797).

c-Met is overexpressed or activated in many human cancers, such as lung cancer, gastric cancer, skin cancer, kidney cancer, colon cancer, and pancreatic cancer, involved in tumor progression and metastasis under tumor formation and increased cell mobility and invasiveness (J. G. Christensen et al., *Cancer Letters,* 225:1-26(2005); W. G. Jiang et al., *Critical Reviews in Oncology/Hematology,* 53:35-69(2005)). c-Met and its ligand HGF are expressed in many tissues, but in normal cases, expressions thereof are restricted in mainly epithelial and mesenchymal progenitor cells. c-Met and HGF/SF are needed in the growth of normal mammals, and have been found to be important for cell metastasis, cell proliferation and survival, morphogenetic differentiation, and organization of three-dimensional tubular structures (renal tubular cells, and line formation). HGF/SF is an angiogenesis factor, and the c-Met signaling in endothelial cells induces cell responses required for an angiogenesis (proliferation, mobility, and invasion).

It was found that c-Met and its ligand HGF, are co-expressed at increased levels in various human cancers. However, since receptors and ligands are normally expressed depending on different cell types, c-Met signaling is generally regulated by a tumor-stroma interaction in most cases.

In addition, gene amplification, mutation, and rearrangement of c-Met were observed in various human cancers. Families with germline mutations that activate c-Met kinase are prone to multiple kidney tumors as well as tumors in other tissues.

It was found that the expression of c-Met and/or HGF/SF is correlated with the state of disease progression of different types of cancers (lung, colon, breast, prostate, liver, pancreas, brain, kidney, ovaries, stomach, skin, and bone cancers), and the overexpression of c-Met and/or HGF/SF is correlated with poor prognoses and disease outcomes in many major human cancers including lung, liver, gastric, and breast cancers. It was reported that c-Met is directly involved in cancers without a successful treatment regimen, such as pancreatic cancer, glioma, and hepatocellular cancer, and it was reported that the lung cancer caused by activation of ERBB3 signaling pathway has resistance against Gefitinib (product name: Iressa) through the overexpression of c-Met (J. A. Engelman, K. Zejnullahu et. al. *Science*, 316:1039-1043(2007)).

HGF/SF binds to an extracellular domain of c-Met to activate c-Met, and the activation of c-Met induces the tyrosine phosphorylation and downstream signaling through activations of PI3-kinase and Ras/MAPK mediated by Gab1 and Grb2, respectively, thereby inducing cell mobility and proliferation.

It was found that c-Met interacts with other proteins inducing receptor activation, transformation, and invasion, and it was reported that c-Met interacts with α6β4 integrin (a receptor to extracellular matrix (ECM), such as laminine) to promote HGF/SF dependent invasive growth.

Thus, the present inventors, while conducting studies for developing protein kinase inhibitors, experimentally observed that morpholino pyrimidine compounds with particular structures have an excellent effect of inhibiting protein kinases, such as c-Met, Ron, KDR, Lck, Flt1, Flt3, Tie2, TrkA, TrkB, b-Raf, and Aurora-A, and thus can be useful for the prevention and treatment of hyper proliferative disorders thereof.

Throughout the entire specification, many papers and patent documents are referenced and their citations are represented. The disclosures of cited papers and patent documents are entirely incorporated by reference into the present specification, and the level of the technical field within which the present invention falls and details of the present invention are explained more clearly.

DETAILED DESCRIPTION OF THE INVENTION

Technical Problem

The present inventors have endeavored to develop a composition for efficiently preventing or treating various hyper proliferative disorders caused by activity of abnormal tyrosin kinase by finding compounds having tyrosine kinase inhibitory activity. As a result, the present inventors have found that novel triazolopyrazine derivatives of chemical formula 1 below, which have not been known until now, bind to hepatocyte growth factor (HGF) to activate the phosphorylation, thereby significantly inhibiting c-Met kinase activity provoking cell proliferation, migration, invasion, and angiogenesis, and thus completed the present invention.

Therefore, the present invention has been made in view of the above-mentioned problems, and an aspect of the present invention is to provide a novel triazolopyrazine derivative or a pharmaceutically acceptable salt thereof.

Another aspect of the present invention is to provide a pharmaceutical composition containing the novel triazolopyrazine derivative or a pharmaceutically acceptable salt or solvate thereof as an active ingredient for inhibiting c-Met tyrosine kinase activity.

Still another aspect of the present invention is to provide a pharmaceutical composition containing the novel triazolopyrazine derivative or a pharmaceutically acceptable salt or solvate thereof as an active ingredient for preventing or treating hyper proliferative disorders.

Other purposes and advantages of the present disclosure will become clarified by the following detailed description of the invention, claims, and drawings.

Other purposes and advantages of the present disclosure will become clarified by the following detailed description of the invention, claims, and drawings.

Technical Solution

In accordance with an aspect of the present invention, there is provided a triazolopyrazine derivative represented by chemical formula 1:

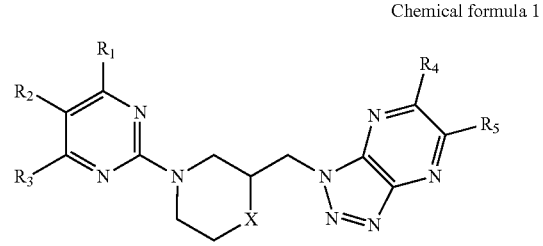

Chemical formula 1 or a pharmaceutically acceptable salt thereof,
wherein:
$R_1$ to $R_3$ are each independently hydrogen, halogen, 5- to 6-membered heterocycloalkyl, 5- to 6-membered heterocycloalkenyl, $C_1$-$C_3$ alkoxy substituted with 5- to 6-membered heterocycloalkyl, $C_1$-$C_5$ alkyl substituted with 5- to 6-membered heterocycloalkyl, $C_1$-$C_3$ alkoxy substituted with 5- to 6-membered heterocycloalkyl, phenyl substituted with halogen, acetyl piperazine, or piperazinyl carbonyl, or 5- to 6-membered heteroaryl substituted with 5- to 6-membered heterocycloalkyl, hydroxy $C_1$-$C_5$ alkyl, or $C_1$-$C_5$ alkyl; wherein at least one of $R_1$ to $R_3$ is not hydrogen;
$R_4$ and $R_5$ are each independently hydrogen, 5- to 6-membered heteroaryl unsubstituted or substituted with $C_1$-$C_5$ alkyl, or phenyl substituted with cyano, halogen, or $C_1$-$C_5$ alkyl; wherein at least one of $R_4$ and $R_5$ is not hydrogen; and
X is oxygen or carbon.

The present inventors have endeavored to develop a composition for efficiently preventing or treating various hyper proliferative disorders caused by activity of abnormal tyrosin kinase by finding compounds having tyrosine kinase inhibitory activity. As a result, the present inventors have found that novel triazolopyrazine derivatives of chemical formula 1 below, which have not been known until now, significantly inhibit c-Met kinase activity.

According to the present invention, the compounds of chemical formula 1 of the present invention bind to hepatocyte growth factor (HGF) to activate the phosphorylation, thereby significantly inhibiting c-Met kinase activity provoking cell proliferation, migration, invasion, and angiogenesis. Therefore, the compounds of the present invention can be useful for the treatment or prevention of various hyper proliferative disorders mediated by cell hyper proliferative activation and excessive angiogenesis.

As used herein, the term "halogen" refers to halogen elements, for example, includes fluorine, chlorine, bromine, and iodine.

As used herein, the term "heterocycloalkyl" refers to a saturated carbon ring containing oxygen, sulfur, or nitrogen as a heteroatom therein. Preferably, the heteroatom is nitrogen or oxygen. The number of heteroatoms is 1 to 4, and preferably 1 to 2. The term "5- to 6-membered heterocycloalkyl" means that the total of carbon atoms and heteroatoms constituting the ring is 5 to 6.

As used herein, the term "alkoxy" refers to a radical formed by the removal of hydrogen from alcohol, and the number of carbon atoms on the substituent is not included in cases where $C_1$-$C_3$ alkoxy is substituted.

As used herein, the term "alkyl" refers to a straight-chain or branched-chain saturated hydrocarbon group, and for example, includes methyl, ethyl, propyl, isobutyl, pentyl, hexyl, and the like. $C_1$-$C_5$ alkyl means an alkyl group having an alkyl unit with 1 to 5 carbon atoms, and the number of carbon atoms on the substituent is not included in cases where $C_1$-$C_5$ alkyl is substituted. In chemical formula 1, $C_1$-$C_5$ alkyl is preferably $C_1$-$C_3$ alkyl, and more preferably $C_1$-$C_2$ alkyl.

As used herein, the term "heteroaryl" refers to a heterocyclic aromatic group containing oxygen, sulfur, or nitrogen as a heteroatom therein. Preferably, the heteroatom is nitrogen or oxygen, and more preferably nitrogen. The number of heteroatoms is 1 to 4, and preferably 1 to 2. In the heteroaryl, the aryl is preferably monoaryl or biaryl.

According to a preferable embodiment of the present invention, in chemical formula 1, $R_1$ to $R_3$ may be each independently hydrogen; halogen; pyrazole substituted with methyl, hydroxy ethyl, piperidine, or N-methyl piperidine; tetrahydropyridine unsubstituted or substituted with methyl or hydroxy ethyl; phenyl substituted with halogen, morpholinoethoxy, piperazinylethoxy, piperazinylmethyl, morpholinomethyl, acetyl piperazine, or piperazinyl carbonyl; morpholinoethoxy; piperazinylethoxy; or piperidine unsubstituted or substituted with methyl or hydroxy ethyl, wherein two of $R_1$ to $R_3$ are hydrogen.

According to a preferable embodiment of the present invention, in chemical formula 1, $R_4$ and $R_5$ may be each independently hydrogen; N-methyl pyrazole; or phenyl substituted with cyano or halogen, wherein one of $R_4$ and $R_5$ is hydrogen.

According to a preferable embodiment of the present invention, the triazolopyrazine represented by chemical formula 1 may be selected from the group consisting of compounds represented by chemical formulas 2 to 50 below:

Chemical formula 2

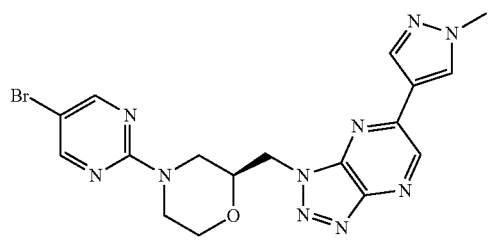

Chemical formula 3

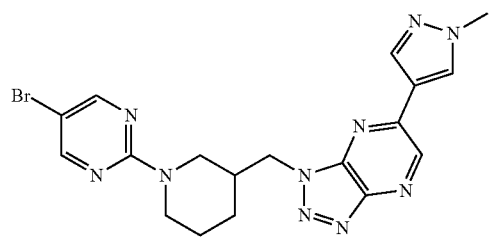

Chemical formula 4

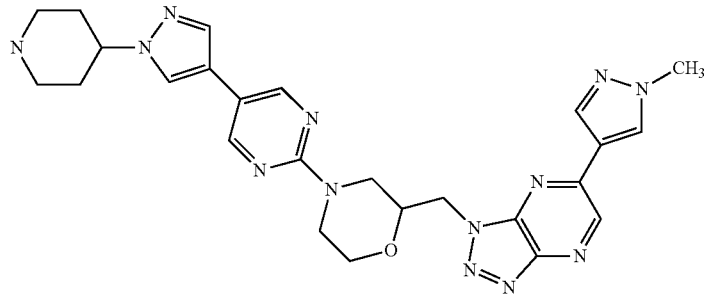

Chemical formula 5

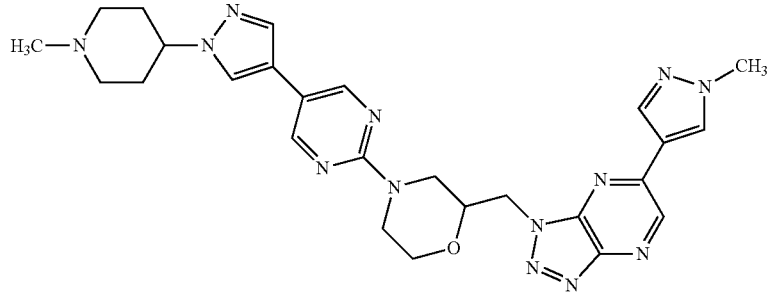

Chemical formula 6

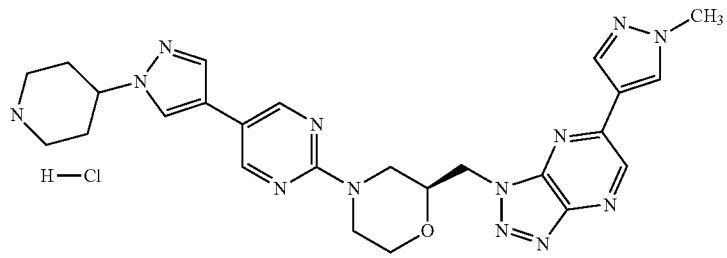

-continued
Chemical formula 7
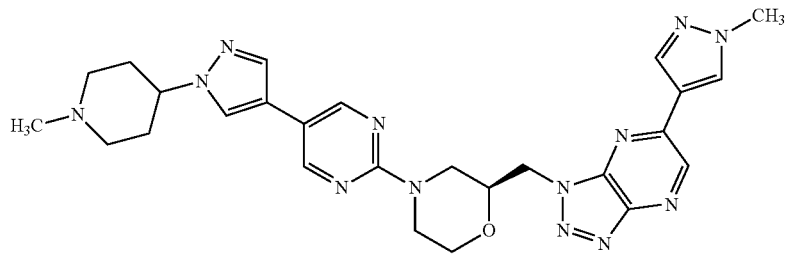
Chemical formula 8
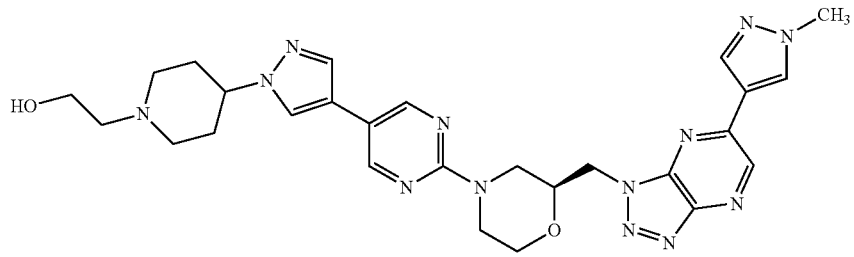
Chemical formula 9
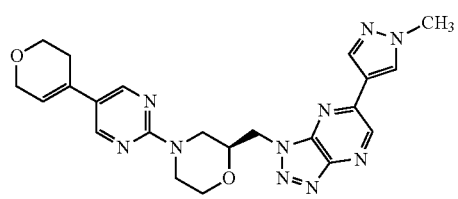
Chemical formula 10
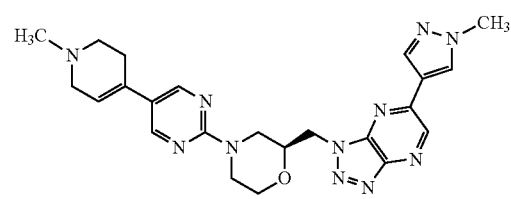
Chemical formula 11
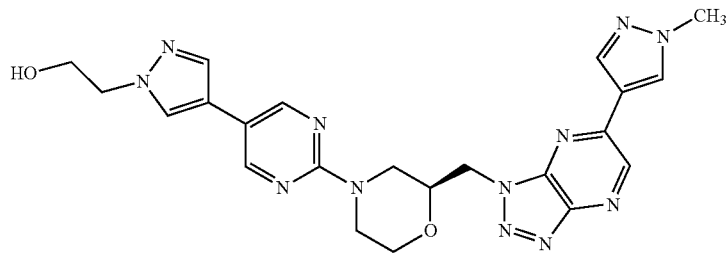
Chemical formula 12
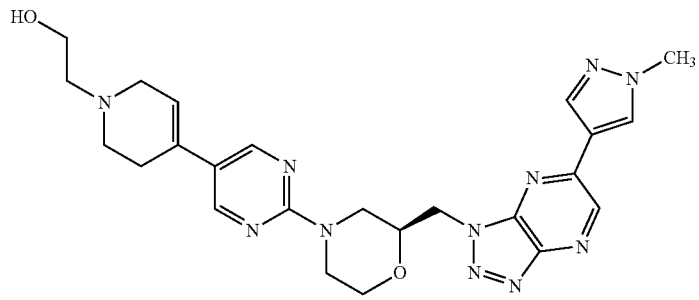
Chemical formula 13
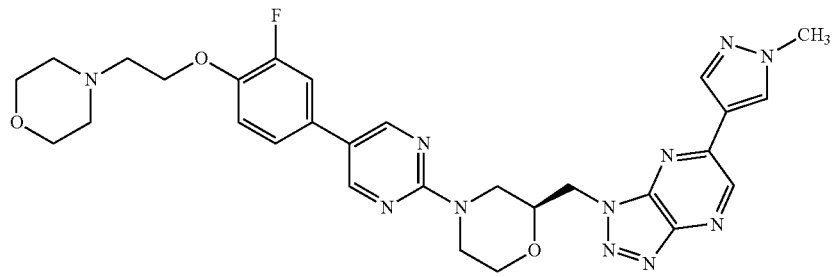

-continued
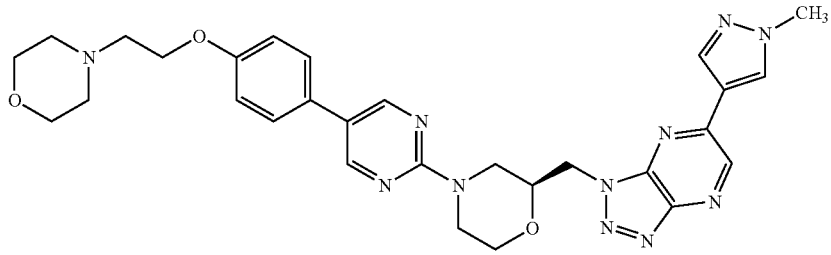
Chemical formula 14
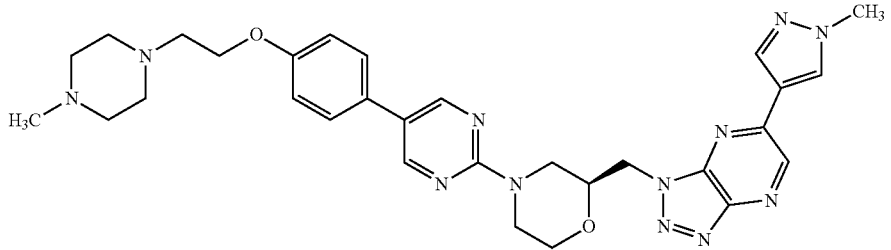
Chemical formula 15
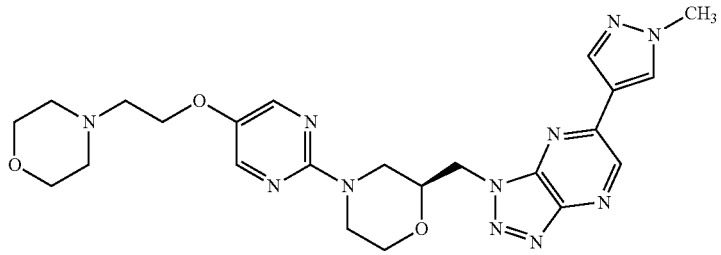
Chemical formula 16
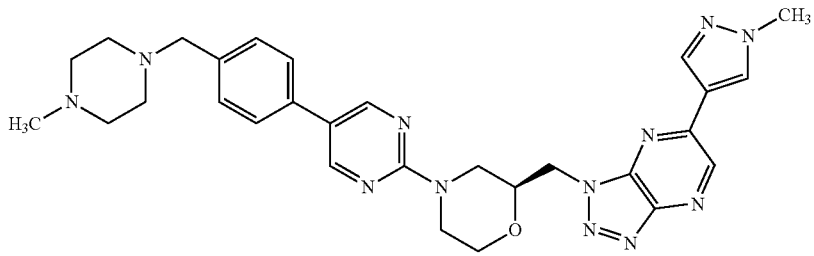
Chemical formula 17
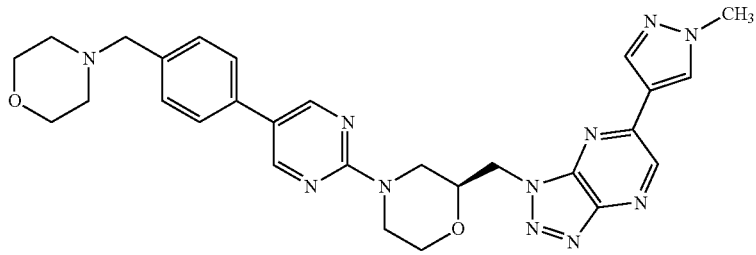
Chemical formula 18
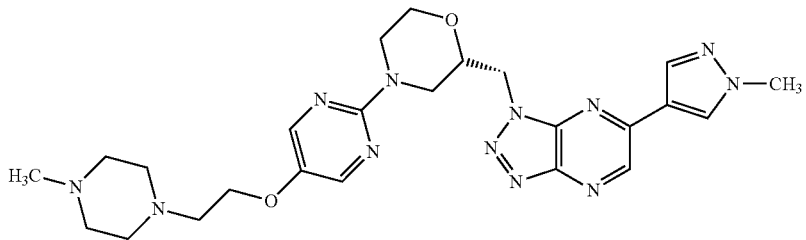
Chemical formula 19

-continued
Chemical formula 20
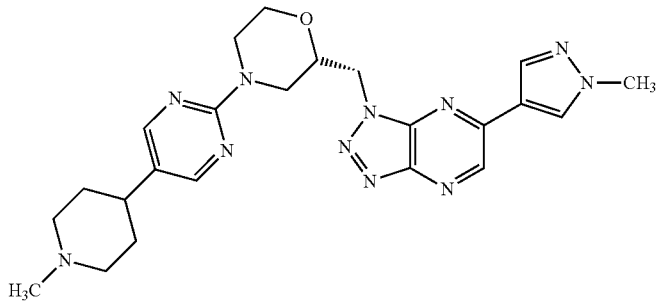
Chemical formula 21
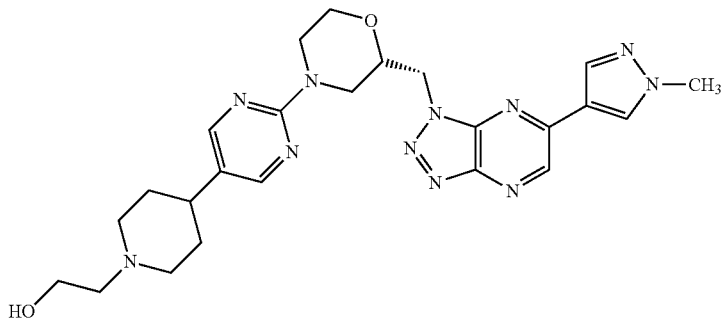
Chemical formula 22
Chemical formula 23
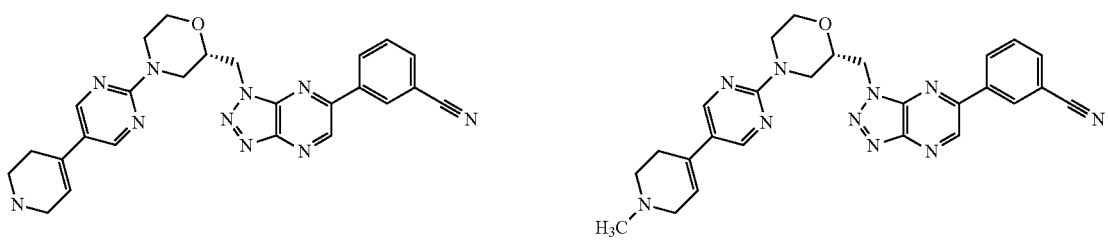
Chemical formula 24
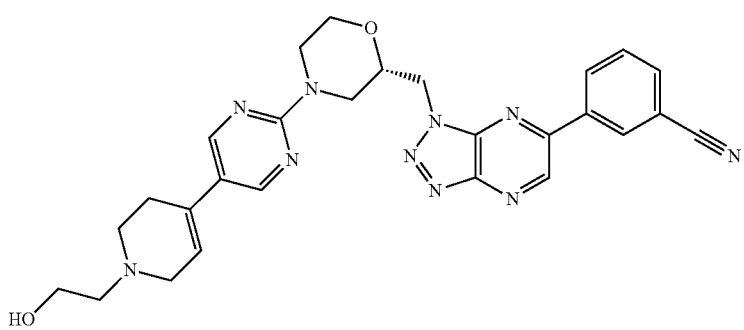
Chemical formula 25
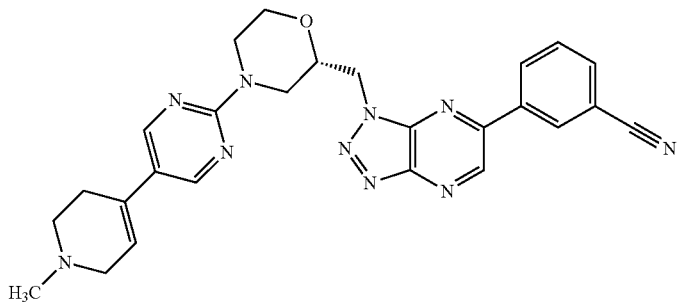

-continued
Chemical formula 26
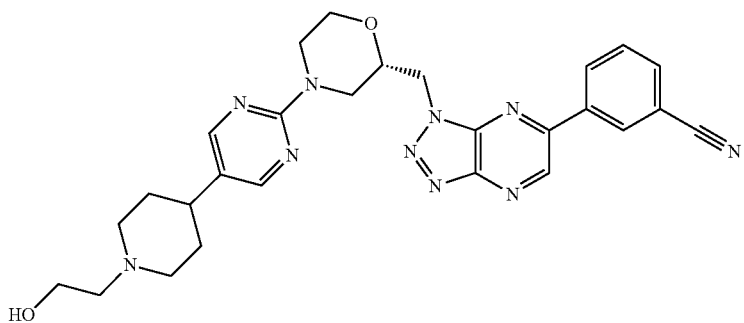
Chemical formula 27
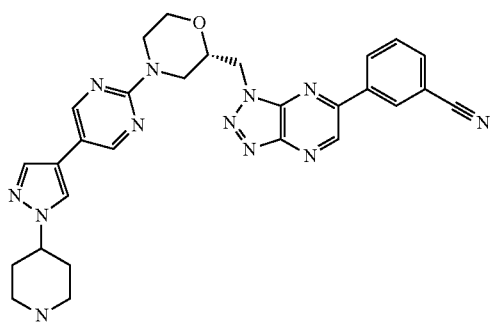
Chemical formula 28
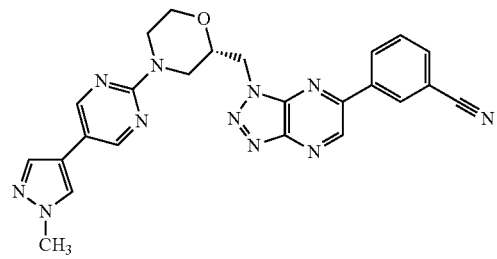
Chemical formula 29
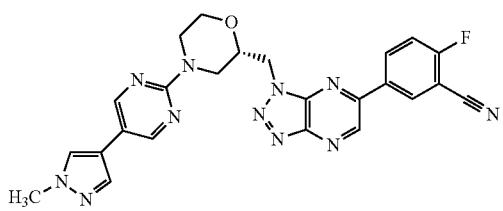
Chemical formula 30
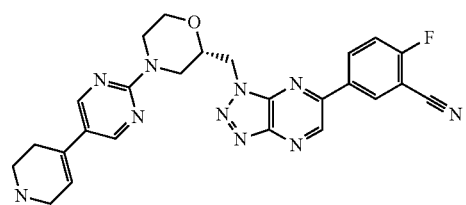
Chemical formula 31
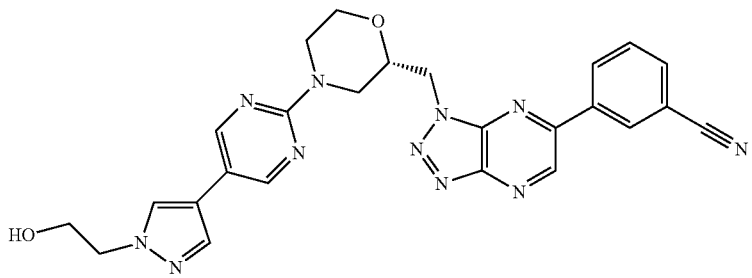
Chemical formula 32
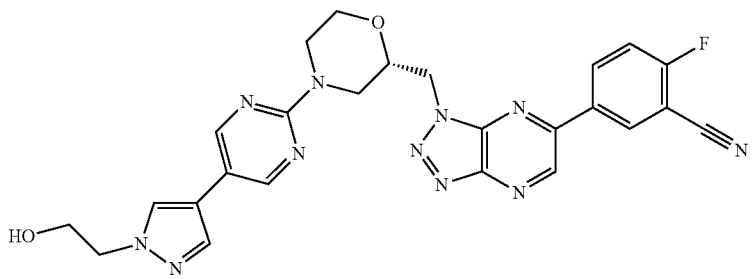

-continued
Chemical formula 33
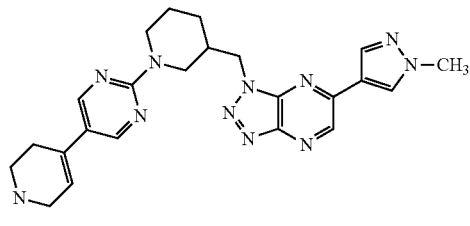
Chemical formula 34
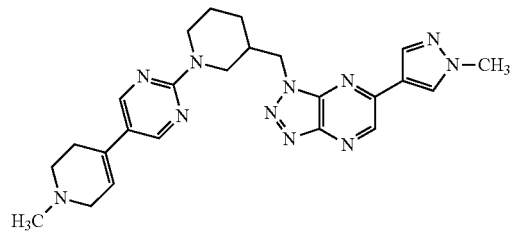
Chemical formula 35
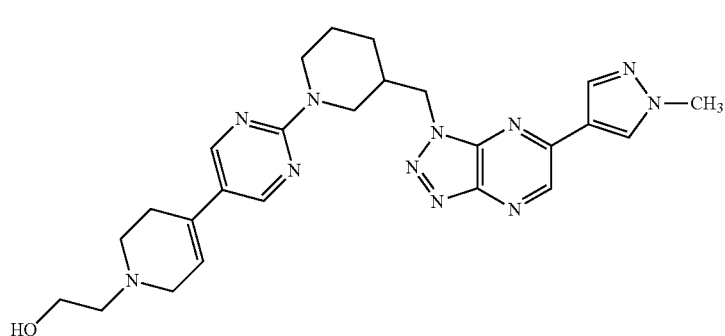
Chemical formula 36
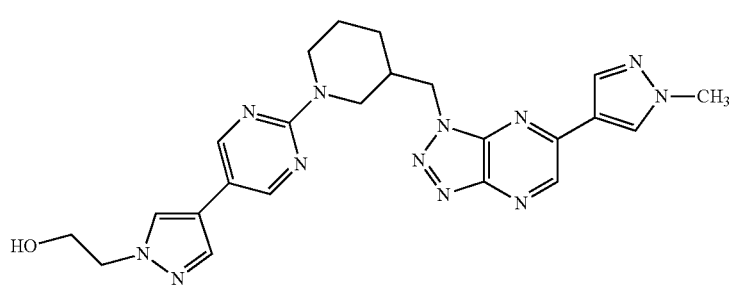
Chemical formula 37
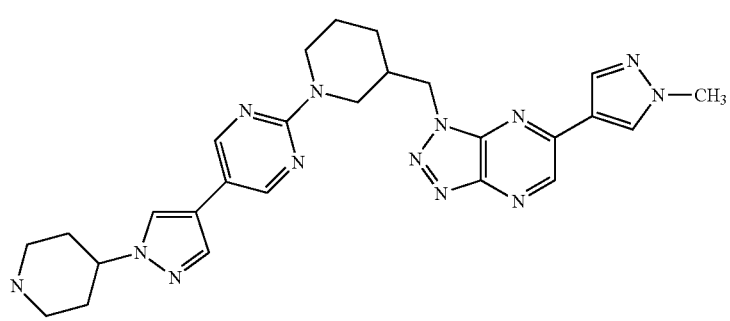
Chemical formula 38
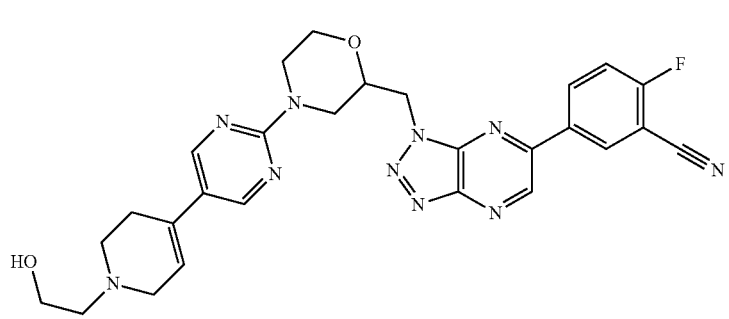

-continued
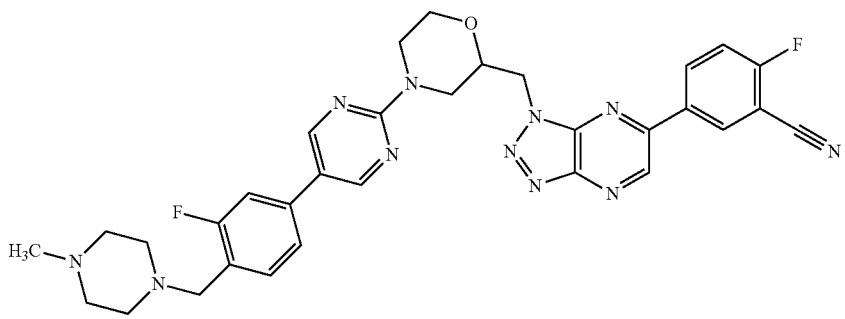
Chemical formula 39
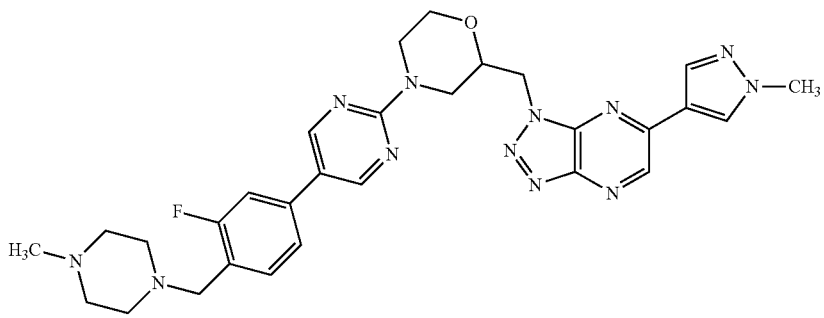
Chemical formula 40
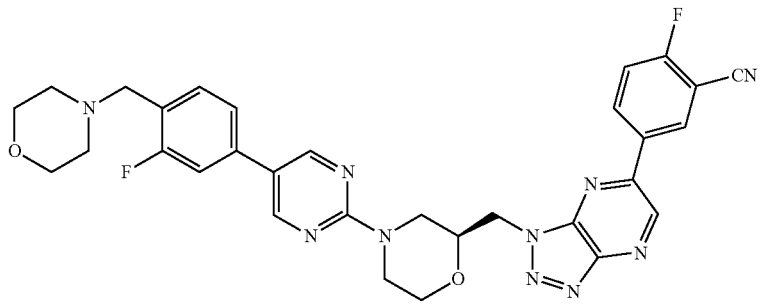
Chemical formula 41
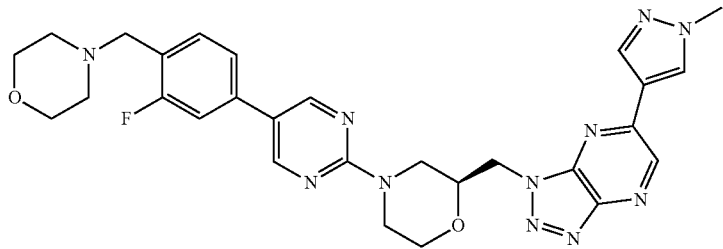
Chemical formula 42
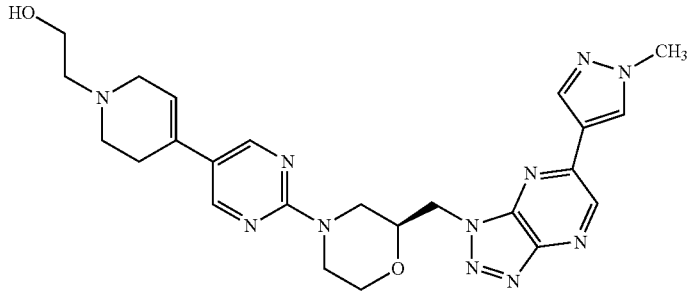
Chemical formula 43

Chemical formula 44
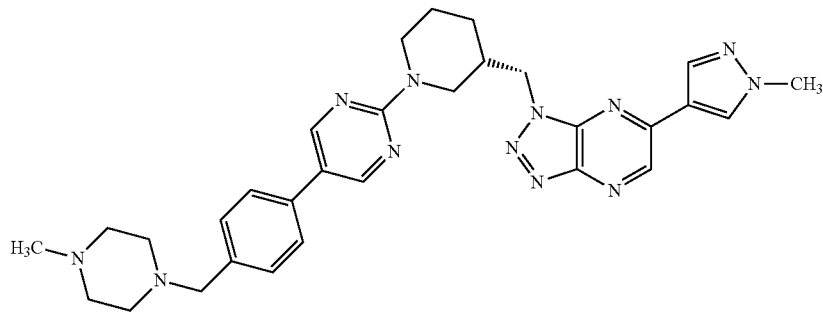
Chemical formula 45
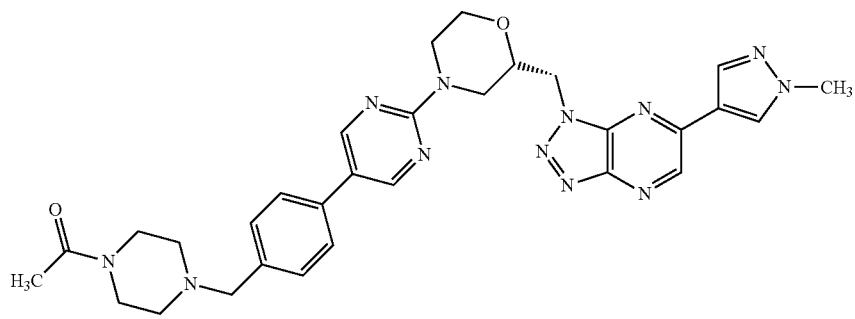
Chemical formula 46
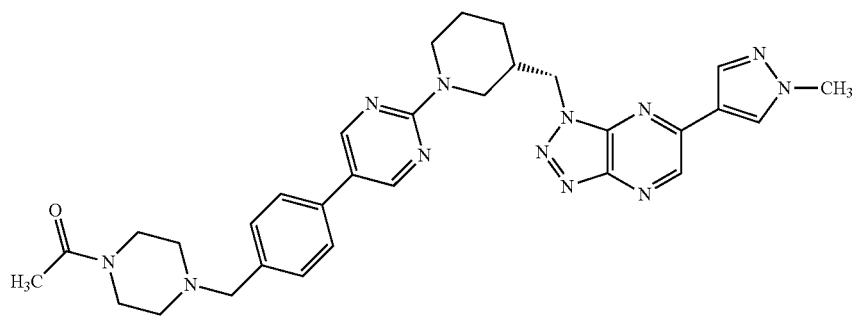
Chemical formula 47
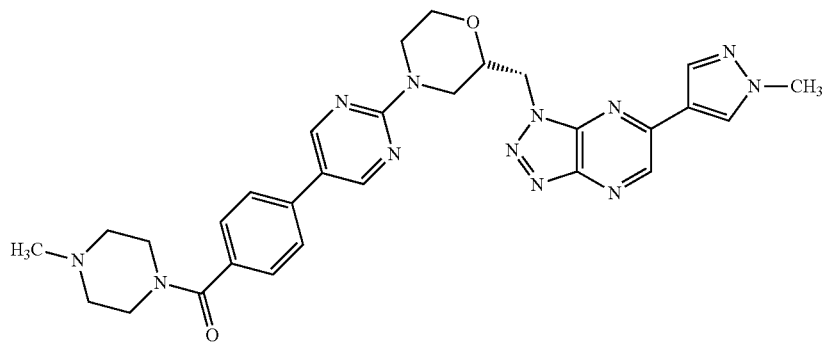
Chemical formula 48
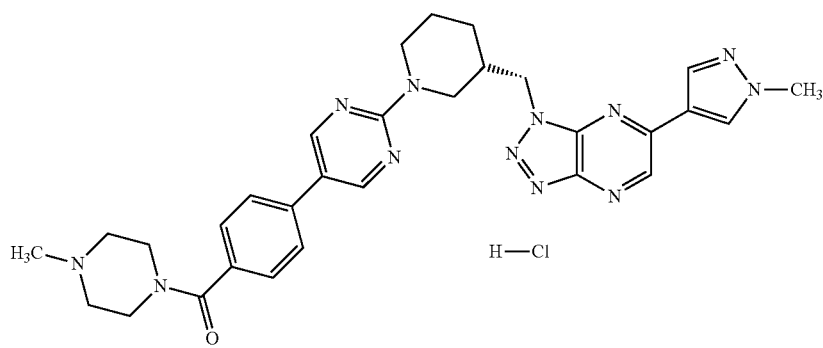

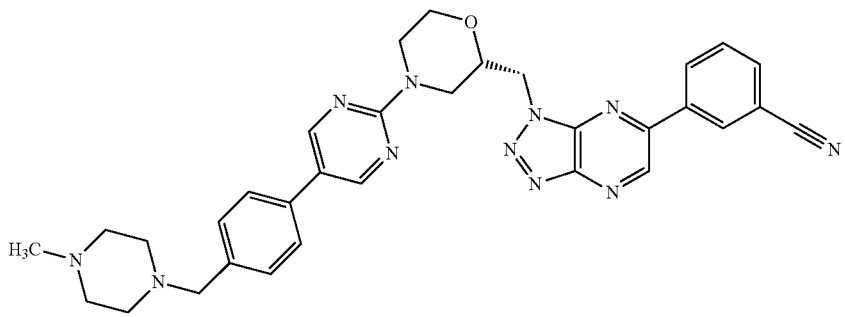

Chemical formula 49

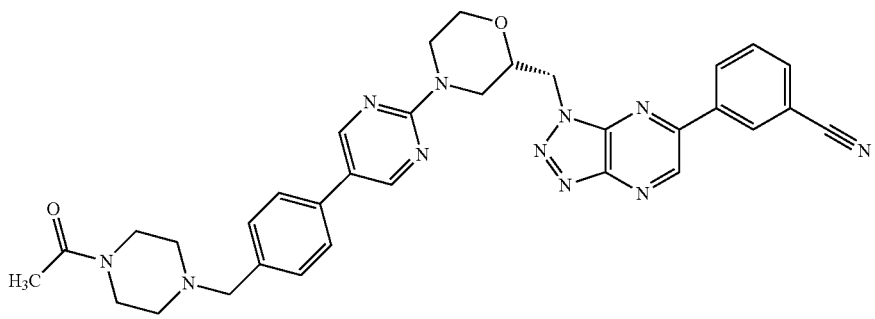

Chemical formula 50

According to a more preferable embodiment of the present invention, the triazolopyrazine derivative may be selected from the group consisting of compounds represented by chemical formulas 6 to 9, 11 to 13, 17, 23, 24, 26 to 32, and 38.

According to the present invention, the listed 18 compounds have very low $IC_{50}$ values in the c-Met kinase inhibitory activity, and inhibit the cancer cell proliferation at high efficiency. Therefore, these compounds can be useful as a very effective therapeutic composition for various hyper proliferative disorders including cancers.

The triazolopyrazine derivative of the present invention can be used as a pharmaceutically acceptable salt, and as the salt, an acid addition salt formed by a pharmaceutically acceptable free acid is useful. As the free acid, an inorganic acid and an organic acid may be used.

Preferably, the pharmaceutically acceptable salt of the triazolopyrazine derivative of the present invention may be selected from the group consisting of hydrochloride, bromate, sulfate, phosphate, citrate, acetate, trifluoroacetate, lactate, tartrate, maleate, fumarate, gluconate, methanesulfonate, glyconate, succinate, 4-toluenesulfonate, gluturonate, embonate, glutamate, or aspartate, but is not limited thereto, and thus includes all salts formed using various inorganic acids and organic acids that are conventionally used in the art.

In addition, the triazolopyrazine derivative of the present invention may exist in a form of a solvate (e.g., hydrate).

In accordance with another aspect of the present invention, there is provided a pharmaceutical composition for inhibiting c-Met tyrosine kinase activity, the pharmaceutical composition containing, as an active ingredient, the foregoing triazolopyrazine derivative of the present invention or a pharmaceutically acceptable salt or solvate thereof.

In accordance with still another aspect of the present invention, there is provided a pharmaceutical composition for preventing or treating hyper proliferative disorder, the pharmaceutical composition containing, as an active ingredient, the forgoing triazolopyrazine derivative of the present invention or a pharmaceutically acceptable salt or solvate thereof.

Since the novel triazolopyrazine derivative used herein has been previously described, the descriptions thereof will be omitted to avoid excessive repetition.

As used herein, the term "hyper proliferative disorder" refers to a disease caused by excessive cell growth, division, and migration, which are not regulated by general restrictions in normally growing animals. Exemplary hyper proliferative diseases that are prevented or treated by the composition of the present invention include cancer, diabetic retinopathy, retinopathy of prematurity, corneal graft rejection, neovascular glaucoma, erythrosis, proliferative retinopathy, psoriasis, rheumatoid arthritis, osteoarthritis, autoimmune diseases, Crohn's disease, restenosis, atherosclerosis, entero-adhesion, ulcers, cirrhosis, glomerulonephritis, diabetic nephropathy, malignant nephrosclerosis, thrombotic microangiopathy, organ transplant rejection, and glomerulopathy, but are not limited thereto, and thus include all hyper proliferative diseases caused by abnormal cell proliferation and excessive angiogenesis.

More preferably, examples of the cancer, which is one of the hyper proliferative diseases that can be prevented or treated by the composition of the present invention, include lung cancer, gastric cancer, pancreatic cancer, colon cancer, ovarian cancer, renal cell cancer, prostate cancer, or brain tumor.

In cases where the composition of the present invention is prepared as a pharmaceutical composition, the pharmaceutical composition of the present invention contains a pharmaceutically acceptable carrier. The pharmaceutically acceptable carrier contained in the pharmaceutical composition of the present invention is one that is conventionally used for the formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present invention may further contain, in addition to the above ingredients, a lubricant, a wetting agent, a sweetening agent, a flavoring agent, an emulsifier, a suspending agent, a preservative, and the like. Suitable pharmaceutically acceptable carriers and agents are described in detail in *Remington's Pharmaceutical Sciences* (19th ed., 1995).

The pharmaceutical composition of the present invention may be administered orally or parenterally, and examples of parenteral administration may include intravenous, subcutaneous, intramuscular, intraperitoneal, and transdermal injections.

A suitable administration dose of the pharmaceutical composition of the present invention may vary depending on various factors, such as method of formulation, manner of administration, age, body weight, sex, and morbidity of the patient, diet, route of administration, excretion rate, and response sensitivity. The dose per day of the pharmaceutical composition of the present invention may be, for example, 0.001 to 100 mg/kg.

The pharmaceutical composition of the present invention may be formulated into a unit dose or a multidose container, as a general dosage form, using the pharmaceutically acceptable carriers and/or excipients according to the methods known to those skilled in the art. The dosage form refers to, for example, oral (tablet, capsule, or powder), intrabuccal, sublingual, intrarectal, intravaginal, intranasal, topical, or parenteral (including intravenous, sponge formulated, muscular, subcutaneous, and intravascular) administration formulations. For example, the compound according to the present invention may be administered orally, intrabuccally, sublingually, in a tablet form containing starch or lactose, a capsule form with or without excipient, or an elixir or suspension form containing sweetening or coloring chemicals. The liquid preparation may be formulated with pharmaceutically acceptable additives, such as a suspension (e.g., semi-synthesized glyceride, such as methylcellulose or Witepsol; or a glyceride mixture, such as a mixture of apricot kernel oil and PEG-6 ester or a mixture of PEG8 and caprylc/capric glyceride). In cases of parenteral administration, for example, intravenous, intracavernous, intramuscular, subcutaneous, and intravascular injections, it is preferable to use a sterilized aqueous solution, and here, the solution may contain other materials (e.g, salt or monosaccharide, such as mannitol or glucose) to be isotonic with the blood.

In accordance with still another aspect of the present invention, there is provided a method for preventing or treating hyper proliferative disorders, the method including administering the foregoing triazolopyrazine derivative of the present invention or a pharmaceutically acceptable salt or solvate thereof.

Since the triazolopyrazine derivative, and a pharmaceutically acceptable salt or solvate thereof, which are used in the present invention, and hyper proliferative diseases that can be prevented or treated by the composition of the present invention have been previously described, the descriptions thereof will be omitted to avoid excessive repetition.

Advantageous Effects

Features and advantages of the present invention are summarized as follows:

(a) The present invention provides a novel triazolopyrazine derivative or pharmaceutically acceptable salt thereof, a pharmaceutical composition containing the same as an active ingredient for inhibiting c-Met tyrosin kinase activity, and a pharmaceutical composition containing the same as an active ingredient for preventing or treating hyper proliferative disorders.

(b) The present invention can be useful as a therapeutic agent for various hyper proliferative disorders associated with excessive cell proliferation and growth caused by abnormal kinase activity, such as cancer, psoriasis, rheumatoid arthritis, and diabetic retinopathy, by efficiently inhibiting c-Met tyrosine kinase activity.

BRIEF DESCRIPTION OF THE DRAWINGS

Hereinafter, the present invention will be described in detail with reference to examples. These examples are only for illustrating the present invention more specifically, and it will be apparent to those skilled in the art that the scope of the present invention is not limited by these examples.

EXAMPLES cl Scheme for Each Compound

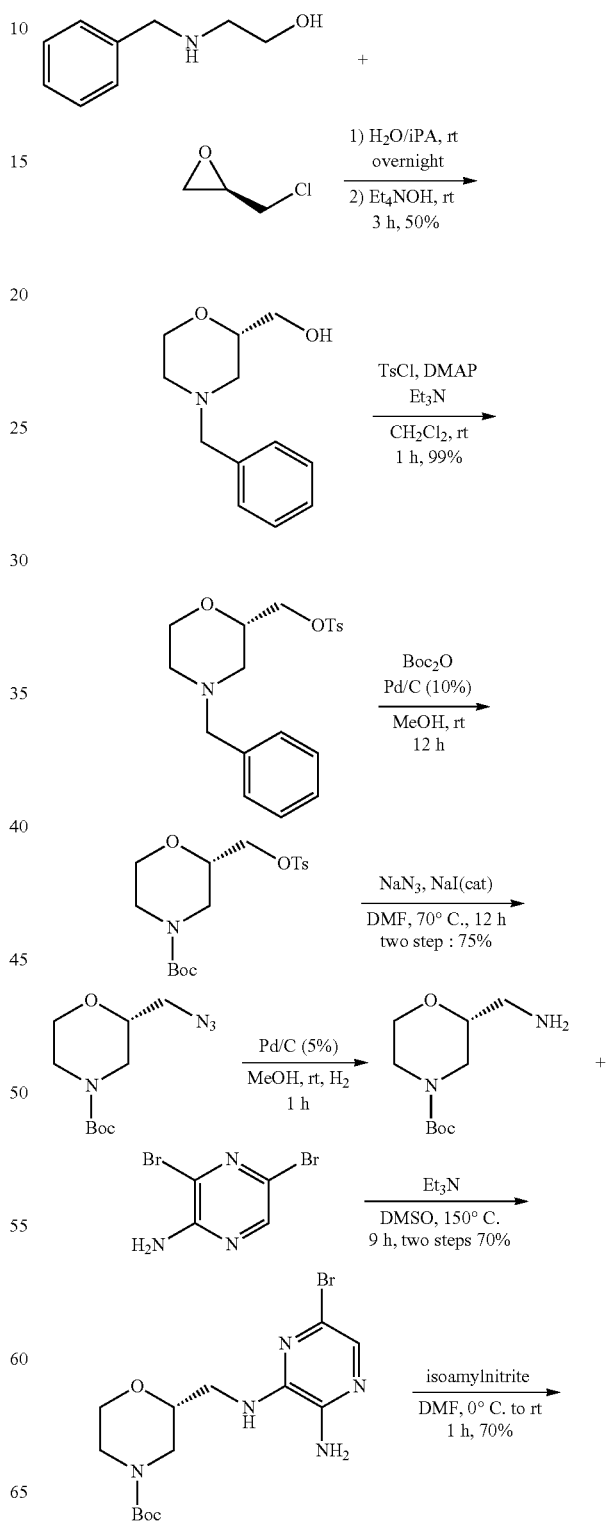

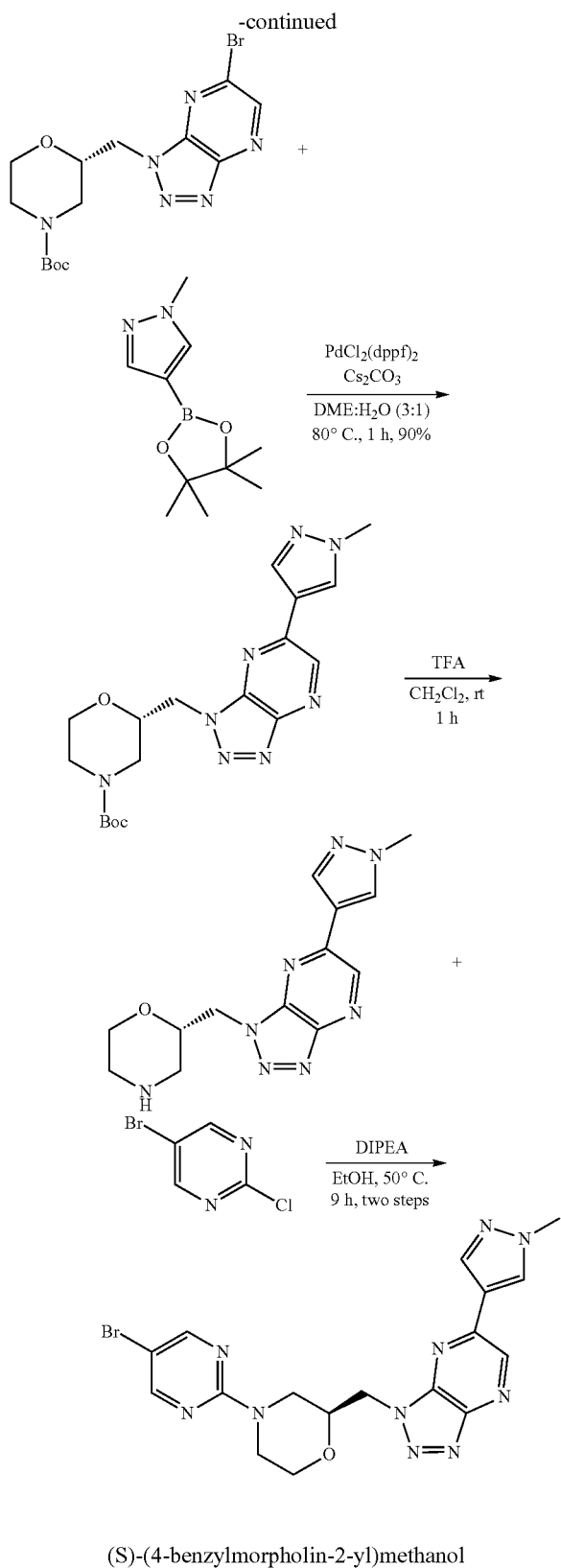

(S)-(4-benzylmorpholin-2-yl)methanol 2-(benzylamino)ethanol 38.3 ml (270.22 mmnol) and (R)-2-(chloromethyl)oxirane 25 g (270.22 mmnol) were dissolved in H₂O/IPA (26 ml+26 ml), and stirred at room temperature overnight. After that, 130 ml of Et₃NOH (35%) dissolved in water was slowly dropped over 1 hour, and stirred at room temperature for 3 hours. After the completion of the reaction, the reaction mixture was adjusted to pH 9 with 1 N HCl, followed by extraction using H₂O and EA, drying (Na₂SO₄), filtration, and concentration under reduced pressure, and the residue was purified by column chromatography (EA:Hex=1:1), to give (S)-(4-benzylmorpholin-2-yl)methanol as a colorless oil (50%).

$^1$H-NMR (300 MHz, CDCl₃) δδ 7.36-7.22 (m, 5H), 3.94-3.85 (m, 1H), 3.76-3.42 (m, 6H), 2.68 (d, J=11.2 Hz, 2H), 2.19 (dt, J=3.1 Hz, 11.2 Hz, 1H), 2.00 (t, J=10.9 Hz, 1H)

(S)-(4-benzylmorpholin-2-yl)methyl 4-methylbenzenesulfonate (S)-(4-benzylmorpholin-2-yl)methanol 36 g (173.68 mmnol) was dissolved in CH₂Cl₂ (400 ml), and TsCl (49.6 g, 260.52 mmol), DMAP (2.12 g, 17.36 mmol), and Et₃N (36.31 ml, 260.52 mmol) were added, followed by stirring at room temperature for 1 hour. After the completion of the reaction, the reaction mixture was extracted with H₂O and EA, followed by drying (Na₂SO₄), filtration, and concentration under reduced pressure, and then the residue was purified by column chromatography (EA:Hex=1:4), to give (S)-(4-benzylmorpholin-2-yl)methyl 4-methylbenzene sulfonate as a white solid (62.15 g, 99%).

(S)-tert-butyl 2-((tosyloxy)methyl)morpholine-4-carboxylate (S)-(4-benzylmorpholin-2-yl)methyl 4-methylbenzene sulfonate (62 g, 171.52 mmol) was dissolved in MeOH (500 ml), and BOC2O (44.9 g, 205.83 mmol) and Pd/C (8 g) were added, followed by stirring at room temperature under 50 psi of H₂ (gas) for 12 hours. After the completion of the reaction, the reaction mixture was filtered through celite, followed by drying, and then the next reaction was advanced.

$^1$H-NMR (300 MHz, CDCl₃) δδ 7.81 (d, J=8.1 Hz, 2H), 7.36 (d, J=8.1 Hz, 2H), 4.07-3.99 (m, 2H), 3.94-3.75(m, 2H), 3.67-3.57 (m, 1H), 3.53-3.41 (m, 1H), 2.99-2.81(m, 1H), 2.76-2.58 (m, 1H), 2.46 (s, 3H), 1.46(s, 9H)

(S)-tert-butyl 2-(azidomethyl)morpholine-4-carboxylate (S)-tert-butyl 2-((tosyloxy)methyl)morpholine-4-carboxylate (63.7 g, 171.52 mmol) was dissolved in DMF (550 ml), and then NaN₃ (44.59 g, 686.08 mmol) and NaI (2.5 g, 17.15 mmol) were added, followed by stirring at 70° C. overnight. After the completion of the reaction, the reaction mixture was extracted with H₂O and EA, followed by drying (Na₂SO₄), filtration, and concentration under reduced pressure, and the residue was purified by column chromatography (EA:Hex=1:5), to give (S)-tert-butyl 2-(azidomethyl)morpholine-4-carboxylate as a white solid (31.1 g, 75%).

$^1$H-NMR (300 MHz, CDCl₃) δδ 4.00-3.76(m, 3H), 3.62-3.48(m, 2H), 3.31(d, J=3.3 Hz, 2H), 3.04-2.86(m, 1H), 2.82-2.64(m, 1H), 1.46(s, 9H)

(R)-tert-butyl 2-(aminomethyl)morpholine-4-carboxylate (S)-tert-butyl 2-(azidomethyl)morpholine-4-carboxylate (31 g, 127.95 mmol) was dissolved in MeOH (400 ml), and Pd/C (5%, 6 g) was added, followed by stirring under H₂ (gas) for 1 hour. After the completion of the reaction, the reaction mixture was filtered through celite, followed by drying, and then the next reaction was advanced.

(R)-tert-butyl 2-(((3-amino-6-bromopyrazine-2-yl)amino)methyl)morpholine-4-carboxylate (R)-tert-butyl 2-(aminomethyl)morpholine-4-carboxylate (26 g, 124.83 mmol) was dissolved in DMSO (300 ml), and 3,5-dibromopyrazine-2-amine (37.8 g, 149.79 mmol) and Et₃N (20.9 ml, 149.79 mmol) were added, followed by stirring at 150° C. for 9 hours. After the completion of the reaction, the reaction mixture was extracted with H₂O, EA, and brine, followed by drying (Na₂SO₄), filtration, and concentration under reduced pressure, and the residue was purified by column chromatography (EA:Hex=1:1), to give (R)-tert-butyl 2-(((3-amino-6-bromopyrazine-2-yl)amino)methyl)morpholine-4-carboxylate (33.9 g, 70%).

¹H-NMR (300 MHz, CDCl₃) δδ 7.46(s, 1H), 4.78-4.68(m, 1H), 4.25(s, 1H), 4.04-3.44(m, 4H), 3.39-3.24(m, 1H), 3.03-2.83(m, 1H), 2.80-2.63(m, 1H), 1.47(s, 9H)

(S)-tert-butyl 2-((6-bromo-1H-[1,2,3]triazolo[4,5-b]pyrazin-1-yl)methyl) morpholine-4-carboxylate (R)-tert-butyl 2-(((3-amino-6-bromopyrazin-2-yl)amino)methyl) morpholine-4-carboxylate (33.9 g, 87.31 mmol) was dissolved in DMF (300 ml), and isoamyl nitrile (14 ml, 104.77 mmol) was slowly dropped at 0° C. After that, the mixture was stirred at 70° C. for 1 hour. After the completion of the reaction, the reaction mixture was extracted with H₂O, EA, and brine, followed by drying (Na₂SO₄), filtration, and concentration under reduced pressure, and the residue was purified by column chromatography (EA:Hex=1:2), to give (S)-tert-butyl 2-((6-bromo-1H-[1,2,3]triazolo[4,5-b]pyrazin-1-yl)methyl)morpholine-4-carboxylate (24.3 g, 70%).

¹H-NMR (300 MHz, CDCl₃) δ 8.78 (s, 1H), 4.84 (dd, J=7.5 Hz, J=14.2 Hz, 1H), 4.73 (dd, J=4.1 Hz, 14.2 Hz, 1H), 4.13-4.02 (m, 2H), 3.87-3.75 (m, 2H), 3.42 (dt, J=2.6 Hz, J=11.7 Hz, 1H), 3.05-2.79 (m, 2H), 1.47 (s, 9H)

(S)-tert-butyl 2-((6-(1-methyl-1H-pyrazol-4-yl)-1H-[1,2,3]triazolo[4,5-b]pyrazin-1-yl)methyl)morpholine-4-carboxylate (S)-tert-butyl 2-((6-bromo-1H-[1,2,3]triazolo[4,5-b]pyrazin-1-yl)methyl)morpholine-4-carboxylate (24.3 g, 60.86 mmol), 1-methyl-4-(4,4,5,5-tetramethyl-1,3,2-dioxaborolane-2-yl)-1H-pyrazole (15.1 g, 73.03 mmol), Pd(dppf)₂Cl₂ (2.48 g, 3.04 mmol), and CS₂CO₃ (59.4 g, 182.58 mmol) were dissolved in DME (300 ml):H₂O (150 ml), and the mixture was degassed with N₂, followed by stirring at 80° C. for 3 hours. After the completion of the reaction, the reaction mixture was extracted with H₂O, EA, and brine, followed by drying (Na₂SO₄), filtration, and concentration under reduced pressure, and the residue was purified by column chromatography (EA:Hex=1:1), to give, (S)-tert-butyl 2-((6-(1-methyl-1H-pyrazol-4-yl)-1H-[1,2,3]triazolo[4,5-b]pyrazin-1-yl)methyl)morpholine-4-carboxylate (21.9 g, 90%).

¹H-NMR (300 MHz, CDCl₃) δδ 8.93 (s, 1H), 8.18 (s, 1H), 8.16 (s, 1H), 4.8 (dd, J=7.5 Hz, J=14.1 Hz, 1H), 4.73 (dd, J=4.5 Hz, J=14.1 Hz, 1H), 4.17-4.11 (m, 2H), 4.05 (s, 3H), 3.923.72 (m, 2H), 3.48 (t, J=11.1 Hz, 1H), 3.02 (t, J=11.1 Hz, 1H), 2.972.85 (m, 1H), 1.47 (s, 9H)

(S)-2-((6-(1-methyl-1H-pyrazol-4-yl)-1H-[1,2,3]triazolo[4,5-b]pyrazin-1-yl)methyl)morpholine (S)-tert-butyl 2-((6-(1-methyl-1H-pyrazol-4-yl)-1H-[1,2,3]triazolo[4,5-b]pyrazin-1-yl)methyl)morpholine-4-carboxylate (21.9 g, 54.69 mmol) was dissolved in CH₂Cl₂ (300 ml), and TFA (5.3 g, 82.04 mmol) was added, followed by stirring at room temperature for 2 hours. After the completion of the reaction, the reaction mixture was concentrated under reduced pressure, and the next reaction was advanced.

¹H-NMR (300 MHz, CDCl₃) δδ 8.93 (s, 1H), 8.18 (s, 1H), 8.14 (s, 1H), 4.87 (dd, J=7.3 Hz, J=14.1 Hz, 1H), 4.68 (dd, J=5.1 Hz, J=14.1 Hz, 1H), 4.31-4.09 (m, 1H), 4.05 (s, 3H), 3.90-3.86 (m, 1H), 3.57 (dt, J=2.6 Hz, J=11.2 Hz, 1H), 3.07-3.03 (m, 1H), 2.91 (dt, J=1.1 Hz, J=9.0 Hz, 1H), 2.86-2.78 (m, 2H)

(S)-4-(5-bromopyrimidin-2-yl)-2-((6-(1-methyl-1H-pyrazol-4-yl)-1H-[1,2,3]triazolo[4,5-b]pyrazin-1-yl)methyl)morpholine (Chemical Formula 2)

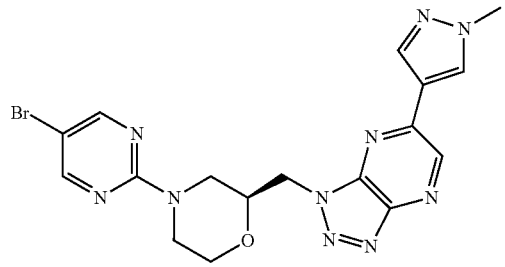 [SMILES: Cn1cc(-c2cnc3nnn(C[C@@H]4CN(c5ncc(Br)cn5)CCO4)c3n2)cn1]

(S)-tert-butyl 2-((6-(1-methyl-1H-pyrazol-4-yl)-1H-[1,2,3]triazolo[4,5-b]pyrazin-1-yl)methyl)morpholine-4-carboxylate (16.4 g, 54.69 mmol) was dissolved in EtOH (500 ml), and 5-bromo-2-chloropyrimidine (12.7 g, 65.62 mmol) and DIPEA (47.6 g, 273.45 mmol) were added, followed by 50° C. for 9 hours. After the completion of the reaction, the reaction mixture was recrystallized with EtOH to give (S)-4-(5-bromopyrimidin-2-yl)-2-((6-(1-methyl-1H-pyrazol-4-yl)-1H-[1,2,3]triazolo[4,5-b]pyrazin-1-yl)methyl)morpholine (18.7 g, 75%).

¹H-NMR (300 MHz, CDCl₃) δ 8.93 (s, 1H), 8.32 (s, 2H), 8.18 (s, 1H), 8.14 (s, 1H), 4.95 (dd, J=7.4 Hz, J=14.2 Hz, 1H), 4.81 (dd, J=4.7 Hz, j=14.2 Hz, 1H), 4.694.63 (m, 1H), 4.414.35 (m, 1H), 4.284.21 (m, 1H), 4.07-4.04 (m, 1H), 4.04 (s, 3H), 3.58 (dt, J=2.6 Hz, J=11.4 Hz, 1H), 3.21-3.14 (m, 1H), 3.09 (dd, J=10.1, Hz J=13.1 Hz, 1H)

(S)-2-((6-(1-methyl-1H-pyrazol-4-yl)-1H-[1,2,3]triazolo[4,5-b]pyrazin-1-yl)methyl)-4-(5-(1-(1-methylpiperidin-4-yl)-1H-pyrazol-4-yl)pyrimidin-2-yl)morpholine (Chemical Formula 7)

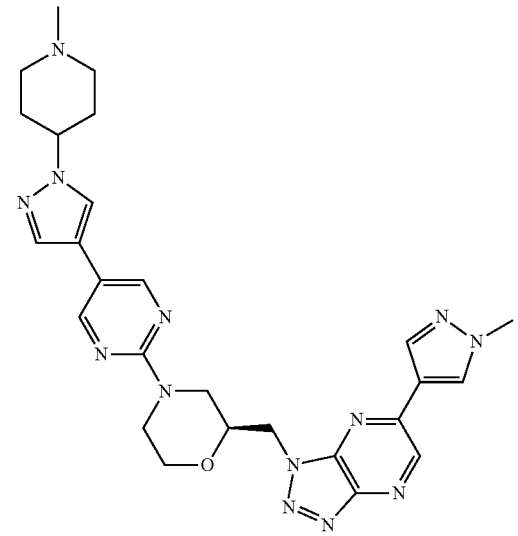 [SMILES: CN1CCC(n2cc(-c3cnc(N4CCO[C@H](Cn5nnc6ncc(-c7cnn(C)c7)nc65)C4)nc3)cn2)CC1]

(S)-tert-butyl 4-(4-(2-(2-((6-(1-methyl-1H-pyrazol-4-yl)-1H-[1,2,3]triazolo[4,5-b]pyrazin-1-yl)methyl)morpholino)pyrimidin-5-yl)-1H-pyrazol-1-yl)piperidine-1-carboxylate 550 mg (0.88 mmol) was dissolved in 35% formaldehyde 0.5 ml and formic acid 2.5 ml, and charged with nitrogen, followed by stirring at 90° C. for 18 hours. After the completion of the reaction, the reaction mixture was cooled in an ice bath, and then adjusted to about pH 10 with a NaOH solution, followed by extraction with EA and brine, and the organic layer was dried over MgSO₄. Column chromatography (methylene chloride:methanol=10:1) gave a product 161 mg (34%).

LCMS calculated for C₂₆H₃₄N₁₃O=541.28; found=542.1

(S)-2-((6-(1-methyl-1H-pyrazol-4-yl)-1H-[1,2,3]
triazolo[4,5-b]pyrazin-1-yl)methyl)-4-(5-(1-(piperi-
din-4-yl)-1H-pyrazol-4-yl)pyrimidin-2-yl)
morpholine HCl salt (Chemical Formula 4)

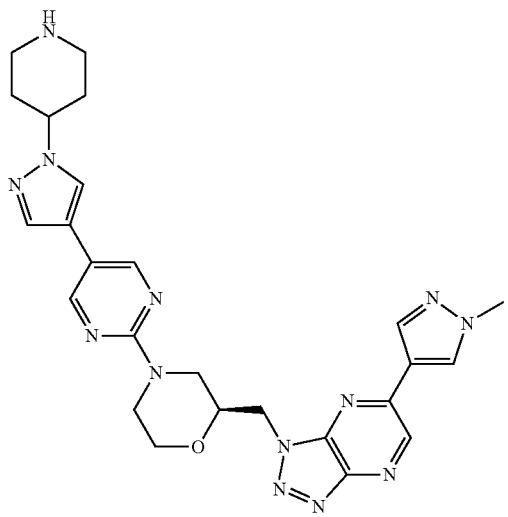 [SMILES: Cn1cc(-c2cnc3nnn(C[C@@H]4CN(c5ncc(-c6cnn(C7CCNCC7)c6)cn5)CCO4)c3n2)cn1]

(S)-tert-butyl 4-(4-(2-(2-((6-(1-methyl-1H-pyrazol-4-yl)-1H-[1,2,3]triazolo[4,5-b]pyrazin-1-yl)methyl)morpholino)pyrimidin-5-yl)-1H-pyrazol-1-yl)piperidine-1-carboxylate 463 mg (0.74 mmol) was dissolved in methylene chloride 20 ml, and 4 M HCl (excess) dissolved in 1,4-dioxane 20 ml was added and then charged with nitrogen, followed by stirring at room temperature for 18 hours. After the completion of the reaction, the reaction mixture was concentrated under reduced pressure to remove methylene chloride and dioxane, thereby giving a yellow solid 493 mg (100%).
LCMS calculated for $C_{25}H_{29}N_{13}O$=527.26, found=528.1

(S)-2-(4-(4-(2-(2-((6-(1-methyl-1H-pyrazol-4-yl)-1H-[1,2,3]triazolo[4,5-b]pyrazin-1-yl)methyl)morpholino)pyrimidin-5-yl)-1H-pyrazol-1-yl)piperidin-1-yl)ethanol (Chemical Formula 8)

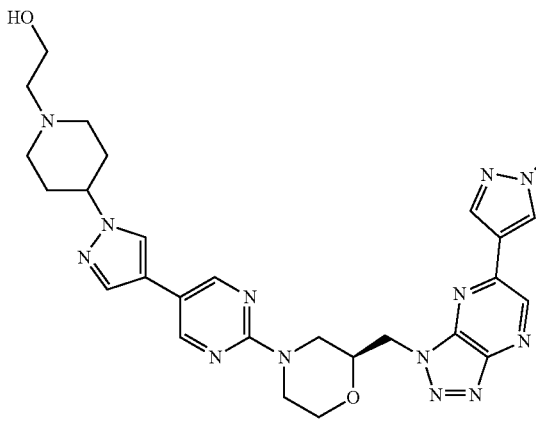

(S)-2-((6-(1-methyl-1H-pyrazol-4-yl)-1H-[1,2,3]triazolo[4,5-b]pyrazin-1-yl)methyl)-4-(5-(1-(piperidin-4-yl)-1H-pyrazol-4-yl)pyrimidin-2-yl)morpholine HCl salt 20 mg (0.04 mmol) was dissolved in dimethylformamide 1 ml, and 2-bromoethanol 6.6 mg (0.05 mmol) and K₂CO₃ 15 mg (0.11 mmol) were added and then charged with nitrogen, followed by stirring at 60° C. for 4 hours. After the reaction, the reaction mixture was concentrated under reduced pressure to remove dimethylformamide, followed by extraction with EA and brine, and the organic layer was dried over MgSO₄. Separation by column chromatography (methylene chloride: methanol=10:1) gave a product 33 mg (65%).
LCMS calculated for $C_{27}H_{33}N_{13}O_2$=571.29, found=572.1

(S)-2-((6-(1-methyl-1H-pyrazol-4-yl)-1H-[1,2,3]
triazolo[4,5-b]pyrazin-1-yl)methyl)-4-(5-(4-(2-mor-
pholinoethoxy)phenyl)pyrimidin-2-yl)morpholine
(Chemical Formula 14)

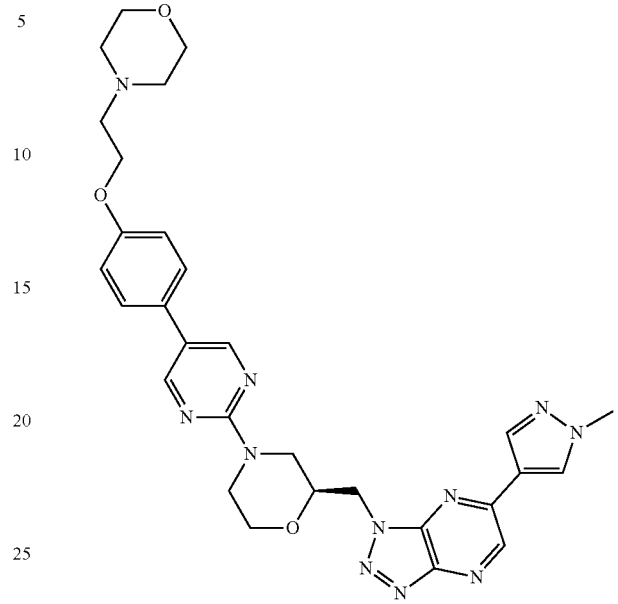

(S)-4-(5-bromopyrimidin-2-yl)-2-((6-(1-methyl-1H-pyrazol-4-yl)-1H-[1,2,3]triazolo[4,5-b]pyrazin-1-yl)methyl)morpholine 15 mg (0.03 mmol) was dissolved in dioxane 1 ml, and 4-(2-(4-(4,4,5,5-tetramethyl-1,3,2-dioxaborolane-2-yl)phenoxy)ethyl)morpholine 16.5 mg (0.05 mmol), 1M Na₂CO₃ 98 μl (0.09 mmol), and Pd(pph₃)₄ 2 mg (0.001 mmol) were added and then charged with nitrogen, followed by stirring at 105° C. for 18 hours. After the reaction, the reaction mixture was extracted with EA and brine, and the organic layer was dried over MgSO₄. Column chromatography (methylene chloride methanol=20:1) gave a product 6 mg (31%).
LCMS calculated for $C_{29}H_{33}N_{11}O_3$=583.28, found=583.8

(S)-2-((6-(1-methyl-1H-pyrazol-4-yl)-1H-[1,2,3]
triazolo[4,5-b]pyrazin-1-yl)methyl)-4-(5-(4-(2-(4-
methylpiperazin-1-yl)ethoxy)phenyl)pyrimidin-2-yl)
morpholine (Chemical Formula 15)

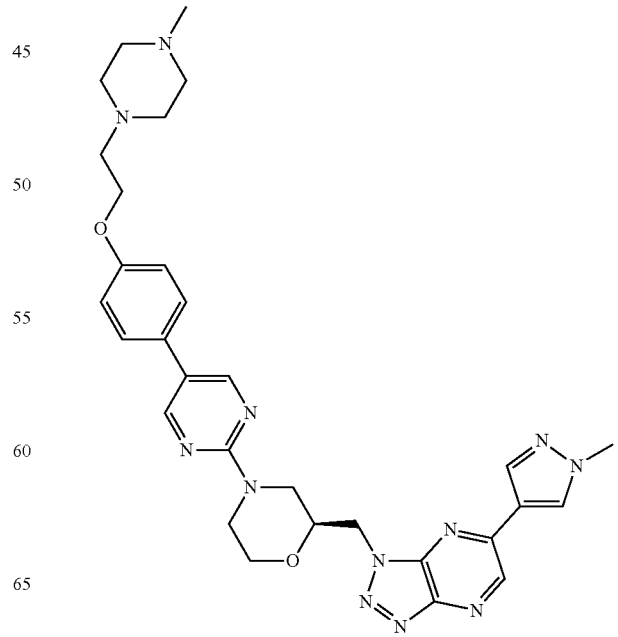

(S)-4-(5-bromopyrimidin-2-yl)-2-((6-(1-methyl-1H-pyrazol-4-yl)-1H-[1,2,3]triazolo[4,5-b]pyrazin-1-yl)methyl)morpholine 15 mg (0.03 mmol) was dissolved in dioxane 1 ml, and 1-methyl-4-(2-(4-(4,4,5,5-tetramethyl-1,3,2-dioxaborolane-2-yl)phenoxy)ethyl)piperazine 17 mg (0.05 mmol), 1M $Na_2CO_3$ 98 μl (0.09 mmol), and $Pd(pph_3)_4$ 2 mg (0.001 mmol) were added and then charged with nitrogen, followed by stirring at 105° C. for 18 hours. After the reaction, the reaction mixture was extracted with EA and brine, and the organic layer was dried over $MgSO_4$. Column chromatography (methylene chloride methanol=20:1) gave a product 0.7 mg (4%).

LCMS calculated for $C_{30}H_{36}N_{12}O_2$=596.31, found=597.2

(S)-2-((6-(1-methyl-1H-pyrazol-4-yl)-1H-[1,2,3]triazolo[4,5-b]pyrazin-1-yl)methyl)-4-(5-(4-(morpholinomethyl)phenyl)pyrimidin-2-yl)morpholine (Chemical Formula 18)

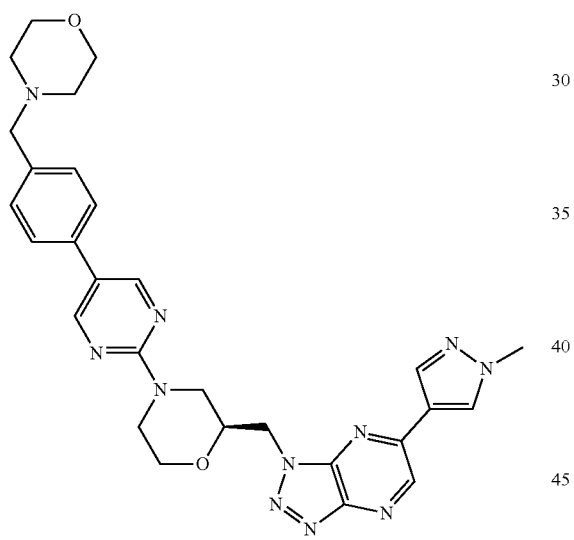

(S)-4-(2-(2-((6-(1-methyl-1H-pyrazol-4-yl)-1H-[1,2,3]triazolo[4,5-b]pyrazin-1-yl)methyl)morpholino)pyrimidin-5-yl)benzaldehyde 40 mg (0.08 mmol) was dissolved in methylene chloride 3 ml, and morpholine 14 μl (0.17 mmol), acetic acid 5.7 μl (0.09 mmol), and $NaBH(OAc)_3$ 26.5 mg (0.12 mmol) were added and then charged with nitrogen, followed by stirring at room temperature for 18 hours. After the reaction, the reaction mixture was cooled and adjusted to pH 8 with $K_2CO_3$(aq.), followed by extraction with MC and water, and the organic layer was dried over $MgSO_4$. Column chromatography (methylene chloride:methanol=20:1) gave a product 18.7 mg (41%).

LCMS calculated for $C_{28}H_{32}N_{11}O_2$=553.27, found=554.0

(S)-2-((6-(1-methyl-1H-pyrazol-4-yl)-1H-[1,2,3]triazolo[4,5-b]pyrazin-1-yl)methyl)-4-(5-(1-methylpiperidin-4-yl)pyrimidin-2-yl)morpholine (Chemical Formula 20)

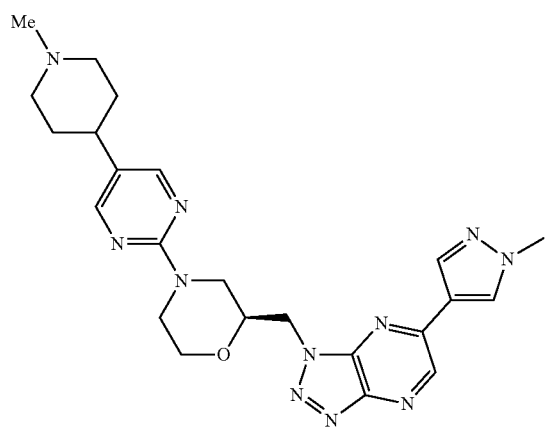 [SMILES: CN1CCC(c2cnc(N3CCO[C@H](Cn4nnc5ncc(-c6cnn(C)c6)nc54)C3)nc2)CC1]

(S)-4-(5-(1-methyl-1,2,3,6-tetrahydropyridin-4-yl)pyrimidin-2-yl)-2-((6-(1-methyl-1H-pyrazol-4-yl)-1H-[1,2,3]triazolo[4,5-b]pyrazin-1-yl)methyl)morpholine 75 mg (0.16 mmol) was dissolved in methanol 3 ml and methylene chloride 2 ml, and an excess of platinum oxide was added. The mixture was degassed, and a hydrogen balloon was connected, followed by reaction at room temperature for 1 day. After the reaction, the platinum oxide was removed using a celite filter, and separated by PLC (methylene chloride:methanol=5:1) to give a yellow solid 13.3 mg (18%).

LCMS calculated for $C_{23}H_{29}N_{11}O$=475.26, found=475.82

(S)-2-(4-(2-(2-((6-(1-methyl-1H-pyrazol-4-yl)-1H-[1,2,3]triazolo[4,5-b]pyrazin-1-yl)methyl)morpholino)pyrimidin-5-yl)piperidin-1-yl)ethanol (Chemical Formula 21)

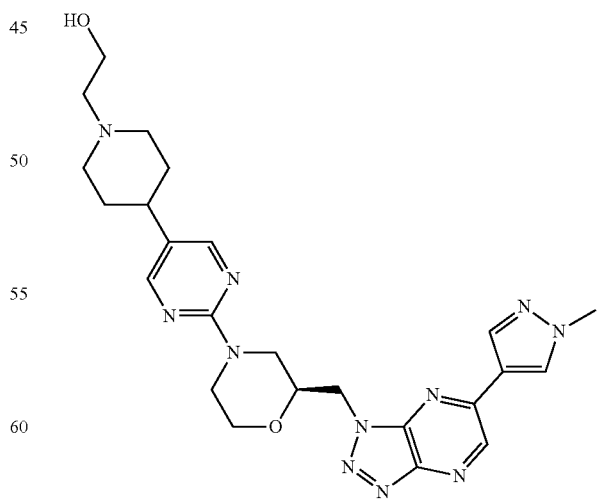

(S)-2-(4-(2-(2-((6-(1-methyl-1H-pyrazol-4-yl)-1H-[1,2,3]triazolo[4,5-b]pyrazin-1-yl)methyl)morpholino)pyrimidin-5-yl)-5,6-dihydropyridin-1(2H)-yl)ethanol 54 mg (0.11 mmol) was dissolved in methanol 3 ml and methylene chloride 2 ml, and an excess of platinum oxide was added. The mixture was degassed, and a hydrogen balloon was connected, followed by reaction at room temperature for 1 day. After the reaction, the platinum oxide was removed using a celite filter, and separation by PLC (methylene chloride:methanol=5:1) gave a yellow solid 7.7 mg (14%).

LCMS calculated for $C_{24}H_{31}N_{11}O_2$=505.27, found=506.28

(S)-tert-butyl 4-(2-(2-((6-(1-methyl-1H-pyrazol-4-yl)-1H-[1,2,3]triazolo[4,5-b]pyrazin-1-yl)methyl)morpholino)pyrimidin-5-yl)-5,6-dihydropyridine-1(2H)-carboxylate Under a sealed tube, (S)-4-(5-bromopyrimidin-2-yl)-2-((6-(1-methyl-1H-pyrazol-4-yl)-1H-[1,2,3]triazolo[4,5-b]pyrazin-1-yl)methyl)morpholine (70 mg, 0.15 mmol), tert-butyl 4-(4,4,5,5-tetramethyl-1,3,2-dioxaborolane-2-yl)-5,6-

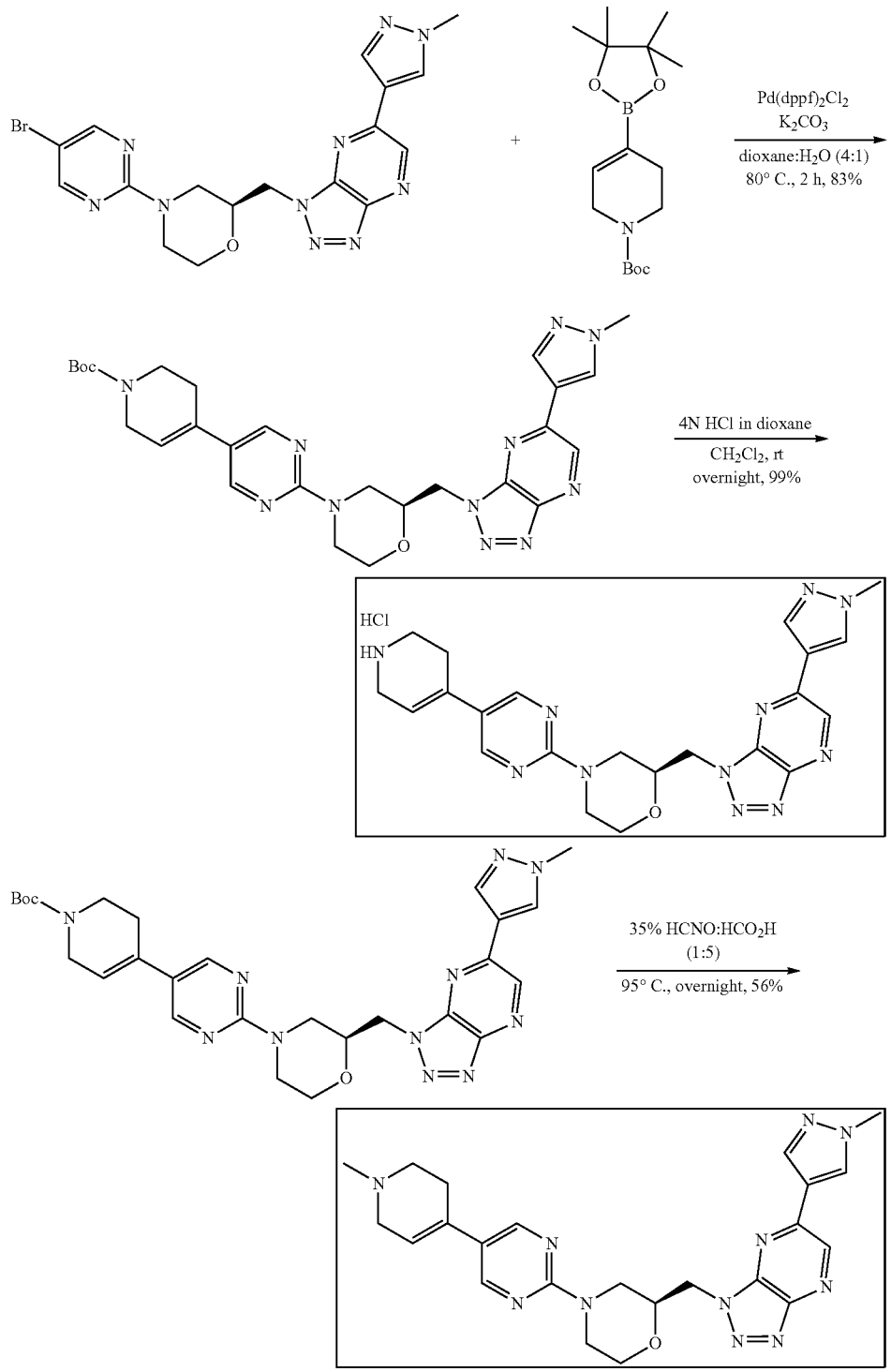

dihydropyridine-1(2H)-carboxylate (57 mg, 0.18 mmol), Pd(dppf)$_2$Cl$_2$ (6.3 mg, 0.0078 mmol), and K$_2$CO$_3$ (64 mg, 0.46 mmol) were dissolved in dioxane (2 ml)+H$_2$O (0.5 ml), and degassed with N$_2$ (gas), followed by stirring at 80° C. for 2 hours. After the completion of the reaction, the reaction mixture was extracted with H$_2$O, EA, and brine, followed by drying (Na$_2$SO$_4$), filtration, and concentration under reduced pressure, and the residue was purified by column chromatography (EA:Hex=2:1), to give (S)-tert-butyl 4-(2-(2-((6-(1-methyl-1H-pyrazol-4-yl)-1H-[1,2,3]triazolo[4,5-b]pyrazin-1-yl)methyl)morpholine)pyrimidin-5-yl)-5,6-dihydropyridine-1(2H)-carboxylate (71 mg, 83%).

$^1$H-NMR(300 MHz, CDCl$_3$) δ 8.91 (s, 1H), 8.34 (s, 2H), 8.16 (s, 1H), 8.12 (s, 1H), 5.92 (brs, 1H), 4.95 (d, J=7.5 Hz, J=14.1 Hz, 1H), 4.80 (dd, J=4.5 Hz, J=14.1 Hz, 1H), 4.75-4.66 (m, 1H), 4.47-4.38 (m, 1H), 4.32-4.20 (m, 1H), 4.10-3.93 (m, 3H), 4.03 (s, 3H), 3.69-3.52 (m, 3H), 3.25-3.03 (m, 2H), 2.48-2.38 (m, 2H), 1.49 (s, 9H)

(S)-2-((6-(1-methyl-1H-pyrazol-4-yl)-1H-[1,2,3]triazolo[4,5-b]pyrazin-1-yl)methyl)-4-(5-(1,2,3,6-tetrahydropyridin-4-yl)pyrimidin-2-yl)morpholine hydrochloride (Salt of Chemical Formula 9)

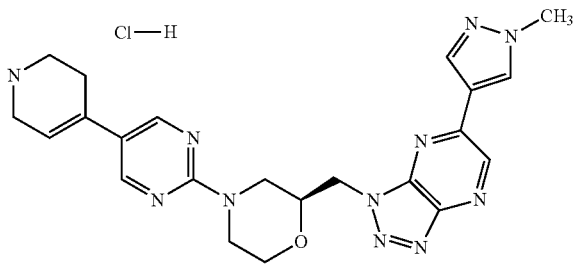 [SMILES: Cn1cc(-c2cnc3nnn(C[C@@H]4CN(c5ncc(C6=CCNCC6)cn5)CCO4)c3n2)cn1 ; Cl]

(S)-tert-butyl 4-(2-(2-((6-(1-methyl-1H-pyrazol-4-yl)-1H-[1,2,3]triazolo[4,5-b]pyrazin-1-yl)methyl)morpholino)pyrimidin-5-yl)-5,6-hydropyridine-1(2H)-carboxylate (33 mg, 0.06 mmol) was dissolved in CH$_2$Cl$_2$ (2 ml), and 4 N HCl in dioxane (1 ml) was added, followed by stirring at room temperature overnight. After the completion of the reaction, the reaction mixture was concentrated under reduced pressure to give (S)-2-((6-(1-methyl-1H-pyrazol-4-yl)-1H-[1,2,3]triazolo[4,5-b]pyrazin-1-yl)methyl)-4-(5-(1,2,3,6-tetrahydropyridin-4-yl)pyrimidin-2-yl)morpholine hydrochloride (29 mg, 99%).

$^1$H-NMR (300 MHz, CDCl$_3$) δ 8.91 (s, 1H), 8.34 (s, 2H), 8.16 (s, 1H), 8.12 (s, 1H), 5.92 (brs, 1H), 4.95 (d, J=7.5 Hz, J=14.1 Hz, 1H), 4.80 (dd, J=4.5 Hz, J=14.1 Hz, 1H), 4.75-4.66 (m, 1H), 4.47-4.38 (m, 1H), 4.32-4.20 (m, 1H), 4.10-3.93 (m, 3H), 4.03 (s, 3H), 3.69-3.52 (m, 3H), 3.25-3.03 (m, 2H), 2.48-2.38 (m, 2H)

(S)-4-(5-(1-methyl-1,2,3,6-tetrahydropyridin-4-yl)pyrimidin-2-yl)-2-((6-(1-methyl-1H-pyrazol-4-yl)-1H-[1,2,3]triazolo[4,5-b]pyrazin-1-yl)methyl)morpholine (Chemical Formula 10)

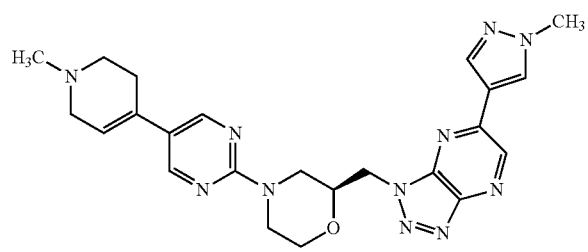

(S)-tert-butyl 4-(2-(2-((6-(1-methyl-1H-pyrazol-4-yl)-1H-[1,2,3]triazolo[4,5-b]pyrazin-1-yl)methyl)morpholino)pyrimidin-5-yl)-5,6-dihydropyridine-1(2H)-carboxylate (36 mg, 0.06 mmol) was dissolved in 35% HCHO (0.1 ml) and acetic acid (0.5 ml), followed by stirring at 95° C. overnight. After the completion of the reaction, the reaction mixture was adjusted to pH 11-12 with NaOH (aq.), and extracted with H$_2$O and EA, followed by drying (Na$_2$SO$_4$), filtration and concentration under reduced pressure, and the residue was purified by column chromatography (MeOH:MC=1:10), to give (S)-4-(5-(1-methyl-1,2,3,6-tetrahydropyridin-4-yl)pyrimidin-2-yl)-2-((6-(1-methyl-1H-pyrazol-4-yl)-1H-[1,2,3]triazolo[4,5-b]pyrazin-1-yl)methyl)morpholine (16.9 mg, 56%).

$^1$H-NMR (300 MHz, CDCl$_3$) δ 8.93 (s, 1H), 8.37 (s, 2H), 8.18 (s, 1H), 8.14 (s, 1H), 5.96 (brs, 1H), 4.97 (d, J=7.7 Hz, J=14.1 Hz, 1H), 4.81 (dd, J=4.2 Hz, J=14.1 Hz, 1H), 4.74-4.68 (m, 1H), 4.46-4.40 (m, 1H), 4.31-4.23 (m, 1H), 4.04 (s, 3H), 4.02-3.97 (m, 1H), 3.59 (dt, J=2.8 Hz, J=11.4 Hz, 1H), 3.23-3.16 (m, 1H), 3.16-3.07 (m, 3H), 2.71 (t, J=5.6 Hz, 2H), 2.55-2.50 (m, 2H), 2.44 (s, 3H)

(2S)-2-((6-(1-methyl-1H-pyrazol-4-yl)-1H-[1,2,3]triazolo[4,5-b]pyrazin-1-yl)methyl)-4-(5-(1-2-(tetrahydro-2H-pyran-2-yloxy)ethyl)-1H-pyrazol-4-yl)pyrimidin-2-yl)morpholine (S)-4-(5-bromopyrimidin-2-yl)-2-((6-(1-methyl-1H-pyrazol-4-yl)-1H-[1,2,3]triazolo[4,5-b]pyrazin-1-yl)methyl)morpholine 300 mg (0.66 mmol) was dissolved in dimethoxymethane 12 ml, and 1-(2-(tetrahydro-2H-pyran-2-yloxy)ethyl)-4-(4,4,5,5-tetramethyl-1,3,2-dioxaborolane-2-yl)-1H-pyrazole 450 mg (1.39 mmol) was added. Cesium carbonate 641 mg (1.97 mmol) was dissolved in distilled water 3 ml, which was then added to the reaction solution. PdCl$_2$(dppf)$_2$ 27 mg (0.03 mmol) was added, and the mixture was purged with N$_2$ (g), followed by stirring at 80° C. for 4 hours. After the completion of the reaction, the reaction mixture was extracted with ethyl acetate and brine, and the organic layer was dried over Na$_2$SO$_4$. Prep LC with 5% MeOH/MC gave a product 290 mg (77%).

$^1$H-NMR (300 MHz, CDCl$_3$) δ 8.91 (s, 1H), 8.43 (s, 2H), 8.16 (s, 1H), 8.12 (s, 1H), 7.68 (s, 1H), 7.67 (s, 1H), 4.99-4.91 (m, 1H), 4.83-4.77 (m, 1H), 4.70 (d, J=12.4 Hz, 1H), 4.55 (s, 1H), 4.44 (s, 1H), 4.36 (t, J=5.2 Hz, 2H), 4.28-4.24 (m, 1H), 4.12-4.05 (m, 1H), 4.01 (s, 3H), 4.00 (d, J=12.4 Hz, 1H), 3.83-3.75 (m, 1H), 3.69-3.59 (m, 2H), 3.48-3.43 (m, 1H), 3.24-3.07 (m, 2H), 2.01 (s, 1H), 1.75 (s, 1H), 1.57-1.49 (m, 4H)

(S)-2-(4-(2-(2-((6-(1-methyl-1H-pyrazol-4-yl)-1H-[1,2,3]triazolo[4,5-b]pyrazin-1-yl)methyl)morpholino)pyrimidin-5-yl)-1H-pyrazol-1-yl)ethanol hydrochloride (Salt of Chemical Formula 11)

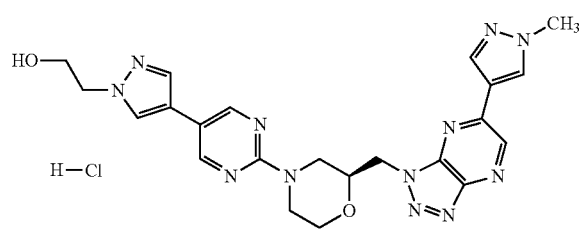 [SMILES: Cn1cc(-c2cnc3nnn(C[C@@H]4CN(c5ncc(-c6cnn(CCO)c6)cn5)CCO4)c3n2)cn1 ; Cl]

(2S)-2-((6-(1-methyl-1H-pyrazol-4-yl)-1H-[1,2,3]triazolo[4,5-b]pyrazin-1-yl)methyl)-4-(5-(1-(2-(tetrahydro-2H-pyran-2-yloxy)ethyl)-1H-pyrazol-4-yl)pyrimidin-2-yl)morpholine 290 mg (0.51 mmol) was dissolved in MC 20 ml, and 4 M HCl in dioxane 2 ml was added. The mixture was stirred at room temperature overnight, and when the reaction was completed, the reaction mixture was concentrated under reduced pressure. MC and 4 M HCl in dioxane were removed, and ether was added to precipitate a solid, followed by decanting, to give a product 236 mg (89%).

$^1$H-NMR (300 MHz, CDCl$_3$) δ 9.20 (s, 1H), 8.65 (s, 2H), 8.63 (s, 1H), 8.30 (s, 1H), 8.11 (s, 1H), 7.85 (s, 1H), 4.93-4.88 (m, 2H), 4.65 (d, J=12.1 Hz, 1H), 4.31 (d, J=12.1 Hz, 1H), 4.12 (t, J=5.1 Hz, 2H), 3.94 (s, 3H), 3.92-3.87 (m, 1H), 3.75 (t, J=5.1 Hz, 1H), 3.56 (s, 1H), 3.07-3.03 (m, 2H), 2.72 (s, 1H), 2.27 (s, 1H)

(S)-tert-butyl 4-(2-(2-((6-(1-methyl-1H-pyrazol-4-yl)-1H-[1,2,3]triazolo[4,5-b]pyrazin-1-yl)methyl)morpholino)pyrimidin-5-yl)-5,6-dihydropyridine-1(2H)-carboxylate (S)-4-(5-bromopyrimidin-2-yl)-2-((6-(1-methyl-1H-pyrazol-4-yl)-1H-[1,2,3]triazolo[4,5-b]pyrazin-1-yl)methyl)morpholine 500 mg (1.09 mmol) was dissolved in dimethoxymethane 8 ml, and then tert-butyl 4-(4,4,5,5-tetramethyl-1,3,2-dioxaborolane-2-yl)-5,6-dihydropyridine-1(2H)-carboxylate 406 mg (1.31 mol) was added. Potassium carbonate 453 mg (3.28 mmol) was dissolved in distilled water 2 ml, which was then added to the reaction solution. PdCl$_2$(dppf)$_2$ 45 mg (0.0547 mmol) was added, and the mixture was purged with N$_2$ (g), followed by stirring at 80° C. for 2 hours. After the completion of the reaction, the reaction mixture was extracted with ethyl acetate and brine, and the organic layer was dried over Na$_2$SO$_4$. 3% MeOH/MC chromatography gave a product 478 mg (78%).

$^1$H-NMR (300 MHz, CDCl$_3$) δ 8.91 (s, 1H), 8.34 (s, 2H), 8.16 (s, 1H), 8.11 (s, 1H), 5.91 (s, 1H), 4.98-4.90 (m, 1H), 4.80-4.72 (m, 1H), 4.70 (d, J=12.7 Hz, 1H), 4.42 (d, J=12.7 Hz, 1H), 4.31-4.23 (m, 1H), 4.06 (s, 2H), 4.02 (s, 3H), 4.02-3.93 (m, 1H), 3.69-3.53 (m, 3H), 3.23-3.06 (m, 2H), 2.43 (s, 2H), 1.95 (s, 1H), 1.48 (s, 9H)

(S)-2-((6-(1-methyl-1H-pyrazol-4-yl)-1H-[1,2,3]triazolo[4,5-b]pyrazin-1-yl)methyl)-4-(5-(1,2,3,6-tetrahydropyridin-4-yl)pyrimidin-2-yl)morpholine HCl salt (Salt of Chemical Formula 9)

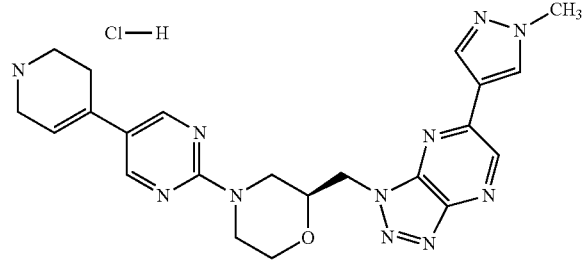

(S)-tert-butyl 4-(2-(2-((6-(1-methyl-1H-pyrazol-4-yl)-1H-[1,2,3]triazolo[4,5-b]pyrazin-1-yl)methyl)morpholino)pyrimidin-5-yl)-5,6-hydropyridine-1(2H)-carboxylate 472 mg (0.84 mmol) was dissolved in MC 15 ml, and 4 N HCl in dioxane (2.5 ml) was added, followed by stirring at room temperature over night. When the reaction was completed, the reaction mixture was concentrated under reduced pressure to remove MC and 4 M HCl in dioxane, and ether was added to precipitate a solid, thereby obtaining the title compound 330 mg (79%).

$^1$H-NMR (300 MHz, CDCl$_3$) δ 8.91 (s, 1H), 8.35 (s, 2H), 8.16 (s, 1H), 8.11 (s, 1H), 5.97 (s, 1H), 4.99-4.93 (m, 1H), 4.86-4.77 (m, 1H), 4.75 (d, J=12.4 Hz, 1H), 4.48 (d, J=12.4 Hz, 1H), 4.37-4.29 (m, 1H), 4.08 (s, 2H), 4.04 (s, 3H), 4.02-3.93 (m, 1H), 3.72-3.58 (m, 3H), 3.32-3.15 (m, 2H), 2.45 (s, 2H), 1.99 (s, 1H)

(S)-2-(4-(2-(2-((6-(1-methyl-1H-pyrazol-4-yl)-1H-[1,2,3]triazolo[4,5-b]pyrazin-1-yl)methyl)morpholino)pyrimidin-5-yl)-5,6-dihydropyridin-1(2H)-yl)ethanol (Chemical Formula 12)

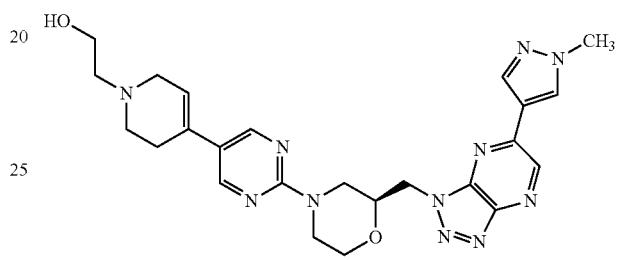

(S)-2-((6-(1-methyl-1H-pyrazol-4-yl)-1H-[1,2,3]triazolo[4,5-b]pyrazin-1-yl)methyl)-4-(5-(1,2,3,6-tetrahydropyridin-4-yl)pyrimidin-2-yl)morpholine HCl salt 330 mg (0.67 mmol) was dissolved in DMF 10 ml, and potassium carbonate 276 mg (1.99 mmol), bromo ethanol 71 μl (0.99 mmol), and TEA 1 ml were added, followed by stirring at room temperature overnight. When the reaction was completed, the reaction mixture was extracted several times with ethyl acetate and brine, and the organic layer was dried over Na$_2$SO$_4$. 7% MeOH/MC chromatography gave a product 210 mg (62%).

$^1$H-NMR (300 MHz, CDCl$_3$) δ 8.91 (s, 1H), 8.35 (s, 2H), 8.16 (s, 1H), 8.11 (s, 1H), 5.95 (s, 1H), 4.98-4.95 (m, 1H), 4.93-4.76 (m, 1H), 4.70 (d, J=12.9 Hz, 1H), 4.42 (d, J=12.9 Hz, 1H), 4.25 (brs, 1H), 3.98-3.93 (m, 1H), 3.70 (t, J=4.5 Hz, 2H), 3.56 (d, J=12.9 Hz, 1H), 3.23 (s, 2H), 3.15 (d, J=12.9 Hz, 1H), 3.08 (d, J=12.9 Hz, 1H), 2.80 (t, J=5.2 Hz, 2H), 2.69 (d, J=4.8 Hz, 2H), 2.49 (s, 2H)

(S)-4-(5-(3-fluoro-4-(2-morpholinoethoxy)phenyl)pyrimidin-2-yl)-2-((6-(1-methyl-1H-pyrazol-4-yl)-1H-[1,2,3]triazolo[4,5-b]pyrazin-1-yl)methyl)morpholine (Chemical Formula 13)

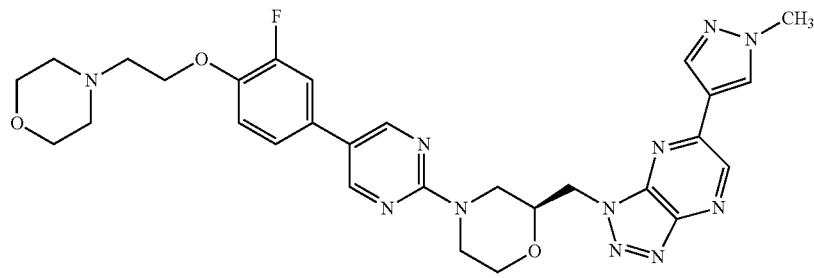 [SMILES: Cn1cc(-c2cnc3nnn(C[C@@H]4CN(c5ncc(-c6ccc(OCCN7CCOCC7)c(F)c6)cn5)CCO4)c3n2)cn1]

(S)-4-(5-bromopyrimidin-2-yl)-2-((6-(1-methyl-1H-pyrazol-4-yl)-1H-[1,2,3]triazolo[4,5-b]pyrazin-1-yl)methyl)morpholine 15 mg (0.033 mmol) was dissolved in dioxane 1 ml, and 4-(2-(2-fluoro-4-(4,4,5,5-tetramethyl-1,3,2-dioxaborolane-2-yl)phenoxy)ethyl)morpholine 17 mg (0.049 mmol) and 1M sodium carbonate 98.4 ul (0.098 mmol) were added. Pd(PPh$_3$)$_4$ 2 mg (0.0016 mmol) was added, and the mixture was purged with N$_2$ (g), followed by stirring at 105° C. for 4 hours. When the reaction was completed, the reaction mixture was extracted with ethyl acetate and brine, and the organic layer was dried over Na$_2$SO$_4$. Prep LC with 4% MeOH/MC gave a product 7.8 mg (40%).

$^1$H-NMR (300 MHz, CDCl$_3$) δ 8.92 (s, 1H), 8.48 (s, 2H), 8.17 (s, 1H), 8.12 (s, 1H), 7.71-7.64 (m, 1H), 7.57-7.48 (m, 1H), 7.16 (d, J=12.1 Hz, 1H), 7.07-7.01 (m, 1H), 4.99-4.92 (m, 1H), 4.85-4.72 (m, 2H), 4.46 (d, J=12.1 Hz, 1H), 4.22 (t, J=5.4 Hz, 2H), 4.02 (s, 3H), 3.37 (s, 4H), 3.63-3.56 (m, 2H), 3.26-3.09 (m, 3H), 2.86 (t, J=4.8 Hz, 2H), 2.62 (s, 4H)

(S)-2-((6-(1-methyl-1H-pyrazol-4-yl)-1H-[1,2,3]triazolo[4,5-b]pyrazin-1-yl)methyl)-4-(5-(4,4,5,5-tetramethyl-1,3,2-dioxaborolane-2-yl)pyrimidin-2-yl)morpholine (S)-4-(5-bromopyrimidin-2-yl)-2-((6-(1-methyl-1H-pyrazol-4-yl)-1H-[1,2,3]triazolo[4,5-b]pyrazin-1-yl)methyl)morpholine 100 mg (0.22 mmol) was dissolved in dioxane 3 ml, and 4,4,4',4',5,5,5',5'-octamethyl-2,2'-bi(1,3,2-dioxaborolane) 83 mg (0.33 mmol) and potassium acetate 85 mg (0.87 mmol) were added, followed by strong injection of N$_2$ (g) purge. PdCl$_2$(dppf)$_2$ 11 mg (0.013 mmol) and dppf 7 mg (0.013 mmol) were added, and the mixture was purged with N$_2$ (g), followed by stirring at 80° C. overnight. When the reaction was completed, the reaction mixture was extracted with ethyl acetate and brine, and the organic layer was dried over Na$_2$SO$_4$ to give a crude compound 109 mg (100%).

$^1$H-NMR (300 MHz, CDCl$_3$) δ 8.91 (s, 1H), 8.16 (s, 1H), 8.11 (s, 2H), 8.10 (s, 1H), 4.95-4.90 (m, 1H), 4.80-4.75 (m, 1H), 4.56 (d, J=12.4 Hz, 1H), 4.31-4.25 (m, 2H), 4.02 (s, 3H), 3.94 (d, J=12.4 Hz, 1H), 3.59-3.53 (m, 1H), 3.13-2.99 (m, 2H), 1.28 (s, 12H)

(S)-2-(2-((6-(1-methyl-1H-pyrazol-4-yl)-1H-[1,2,3]triazolo[4,5-b]pyrazin-1-yl)methyl)morpholino)pyrimidin-5-ol (S)-2-((6-(1-methyl-1H-pyrazol-4-yl)-1H-[1,2,3]triazolo[4,5-b]pyrazin-1-yl)methyl)-4-(5-(4,4,5,5-tetramethyl-1,3,2-dioxaborolane-2-yl)pyrimidin-2-yl)morpholine 109 mg (0.22 mmol) was dissolved in THF 3 ml and distilled water 3 ml, and NaBO$_3$ 65 mg (0.651 mmol) was added. The mixture was stirred at room temperature for 1 hour. When the reaction was completed, the reaction mixture was extracted with MC and water, and the organic layer was dried over Na$_2$SO$_4$. Prep LC with 4% MeOH/MC gave a product 54 mg (63%).

$^1$H-NMR (300 MHz, CDCl$_3$) δ 8.91 (s, 1H), 8.16 (s, 1H), 8.12 (s, 2H), 8.11 (s, 1H), 4.98-4.93 (m, 1H), 4.82-4.77 (m, 1H), 4.56 (d, J=12.2 Hz, 1H), 4.33-4.26 (m, 2H), 4.02 (s, 3H), 3.96 (d, J=12.2 Hz, 1H), 3.60-3.55 (m, 1H), 3.15-3.00 (m, 2H)

(S)-4-(5-(2-chloroethoxy)pyrimidin-2-yl)-2-((6-(1-methyl-1H-pyrazol-4-yl)-1H-[1,2,3]triazolo[4,5-b]pyrazin-1-yl)methyl)morpholine (S)-2-(2-((6-(1-methyl-1H-pyrazol-4-yl)-1H-[1,2,3]triazolo[4,5-b]pyrazin-1-yl)methyl) morpholino)pyrimidin-5-ol 15 mg (0.04 mmol) was dissolved in DMF 2 ml, and 1-bromo-2-chloromethane 16 μl (0.19 mmol) and potassium carbonate 16 mg (0.11 mmol) were added, followed by stirring at 60° C. overnight. When the reaction was completed, the reaction mixture was extracted several times with ethyl acetate and brine, and the organic layer was dried over Na$_2$SO$_4$. Prep LC with 4% MeOH/MC gave a product 9.7 mg (53%).

$^1$H-NMR (300 MHz, CDCl$_3$) δ 8.91 (s, 1H), 8.16 (s, 1H), 8.12 (s, 2H), 8.11 (s, 1H), 4.96-4.91 (m, 1H), 4.80-4.76 (m, 1H), 4.57 (d, J=7.6 Hz, 1H), 4.30-4.24 (m, 2H), 4.20 (t, J=3.3 Hz, 2H), 4.02 (s, 3H), 3.97 (d, J=7.6 Hz, 1H), 3.78 (t, J=3.3 Hz, 2H), 3.61-3.55 (m, 1H), 3.15-3.01 (m, 2H)

(S)-2-((6-(1-methyl-1H-pyrazol-4-yl)-1H-[1,2,3]triazolo[4,5-b]pyrazin-1-yl)methyl)-4-(5-(2-(4-methylpiperazin-1-yl)ethoxy)pyrimidin-2-yl)morpholine (Compound 16)

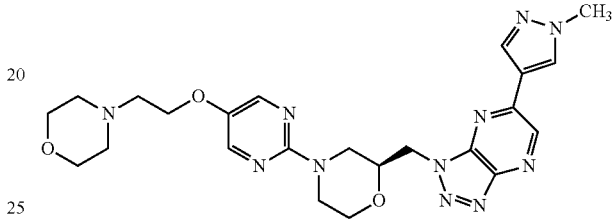

(S)-4-(5-(2-chloroethoxy)pyrimidin-2-yl)-2-((6-(1-methyl-1H-pyrazol-4-yl)-1H-[1,2,3]triazolo[4,5-b]pyrazin-1-yl)methyl)morpholine 9 mg (0.019 mmol) was dissolved in DMF 1 ml, and 1-methylpiperazine 4 μl (0.39 mmol) and KI 4 mg (0.022 mmol) were added. The mixture was stirred at 75° C. overnight. When the reaction was completed, the reaction mixture was extracted several times with ethyl acetate and brine, and the organic layer was dried over Na$_2$SO$_4$. Prep LC with 7% MeOH/MC gave a product 7.8 mg (76%).

$^1$H-NMR (300 MHz, CDCl$_3$) δ 8.91 (s, 1H), 8.16 (s, 1H), 8.11 (s, 1H), 8.10 (s, 2H), 4.98-4.93 (m, 1H), 4.81-4.74 (m, 1H), 4.56 (d, J=12.1 Hz, 1H), 4.27 (d, J=12.1 Hz, 2H), 4.07 (t, J=5.6 Hz, 2H), 4.02 (s, 3H), 3.97 (d, J=12.1 Hz, 1H), 3.66-3.54 (m, 2H), 3.06-2.98 (m, 1H), 2.78 (t, J=5.5 Hz, 2H), 2.62 (brs, 4H), 2.52 (brs, 4H), 2.31 (s, 3H)

LCMS calculated for C$_{24}$H$_{32}$N$_{12}$O$_2$ LCMS=520.28, found=520.97

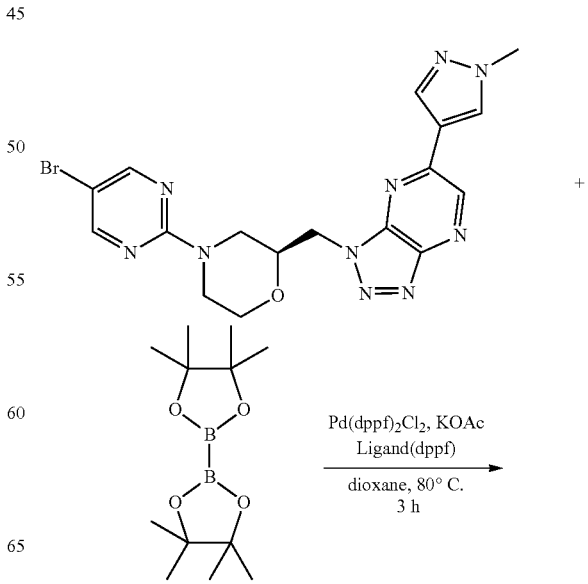

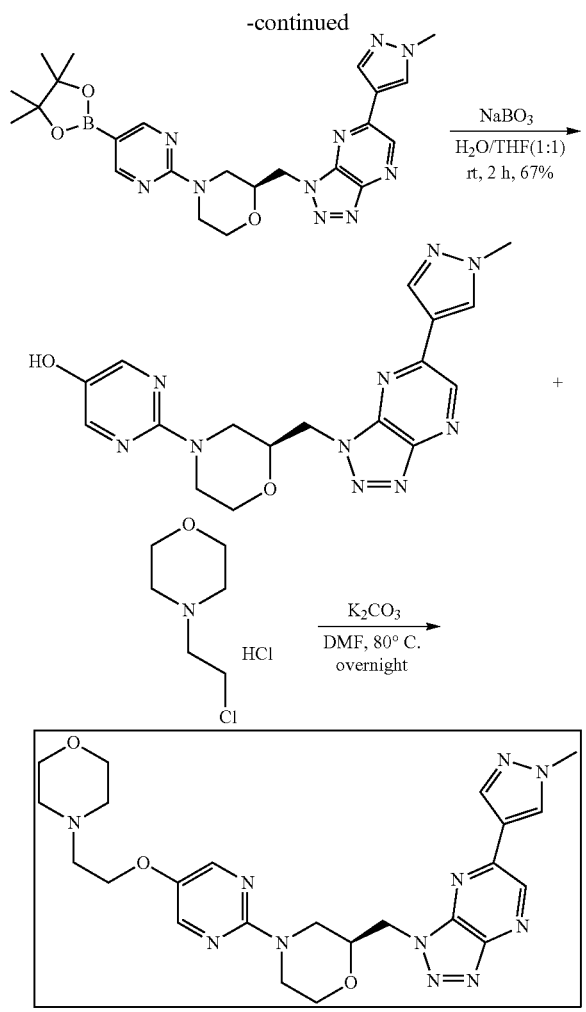

(S)-2-((6-(1-methyl-1H-pyrazol-4-yl)-1H-[1,2,3]
triazolo[4,5-b]pyrazin-1-yl)methyl)-4-(5-(4,4,5,5-
tetramethyl-1,3,2-dioxaborolane-2-yl)pyrimidin-2-
yl)morpholine Under a pressure tube, (S)-4-(5-bromopyrimidin-2-yl)-2-((6-(1-methyl-1H-pyrazol-4-yl)-1H-[1,2,3]triazolo[4,5-b]pyrazin-1-yl)methyl)morpholine 50 mg (0.11 mmol), 4,4,4',4',5,5,5',5'-octamethyl-2,2'-bi(1,3,2-dioxaborolane) 42 mg (0.16 mmol), potassium acetate 43 mg (0.44 mmol), Pd(dppf)2Cl2 5.4 mg (0.007 mmol), and dppf 3.7 mg (0.007 mmol) were dissolved in dioxane 3 ml, and degassed with N2 (gas), followed by stirring at 80° C. for 3 hours. After the completion of the reaction, the reaction mixture was extracted with H2O and EA, followed by drying (Na2SO4), filtration, and concentration under reduced pressure, and the next reaction was advanced.

(S)-2-(2-((6-(1-methyl-1H-pyrazol-4-yl)-1H-[1,2,3]
triazolo[4,5-b]pyrazin-1-yl)methyl)morpholino)pyri-
midin-5-ol (S)-2-((6-(1-methyl-1H-pyrazol-4-yl)-1H-[1,2,3]triazolo[4,5-b]pyrazin-1-yl)methyl)-4-(5-(4,4,5,5-tetramethyl-1,3,2-dioxaborolane-2-yl)pyrimidin-2-yl)morpholine 55 mg (0.11 mmol) was dissolved in THF 2 ml and H2O 2 ml, and NaBO3 16 mg (0.16 mmol) was added, followed by stirring at room temperature for 2 hours. After the completion of the reaction, the reaction mixture was extracted with H2O, EA, and brine, followed by drying (Na2SO4), filtration, and concentration under reduced pressure, and the residue was purified by column chromatography (MeOH:MC=1:10), to give (S)-2-(2-((6-(1-methyl-1H-pyrazol-4-yl)-1H-[1,2,3]triazolo[4,5-b]pyrazin-1-yl)methyl)morpholino)pyrimidin-5-ol 29 mg (two steps: 67%).

$^1$H-NMR (300 MHz, DMSO) δ 9.30(brs, 1H), 9.14(s, 1H), 8.58(s, 1H), 8.25 (s, 1H), 8.01(s, 2H), 4.88-4.77(m, 2H), 4.46-4.34(m, 1H), 4.19-4.01(m, 2H), 3.90(s, 3H), 3.86-3.77(m, 1H), 3.47-3.34(m, 1H), 2.94-2.74(m, 2H)

(S)-2-((6-(1-methyl-1H-pyrazol-4-yl)-1H-[1,2,3]
triazolo[4,5-b]pyrazin-1-yl)methyl)-4-(5-(2-mor-
pholinoethoxy)pyrimidin-2-yl)morpholine (Chemi-
cal Formula 16)

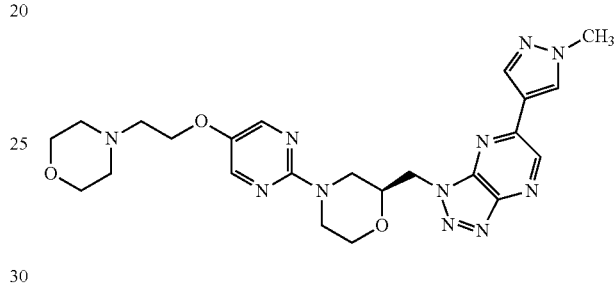

(S)-2-(2-((6-(1-methyl-1H-pyrazol-4-yl)-1H-[1,2,3]triazolo[4,5-b]pyrazin-1-yl)methyl)morpholino)pyrimidin-5-ol 26 mg (0.066 mmol) was dissolved in DMF 2 ml, and 4-(2-chloroethyl)morpholinehydrochloride 14.8 mg (0.079 mmol) and potassium carbonate 28 mg (0.19 mmol) were added, followed by stirring at 80° C. overnight. After the completion of the reaction, the reaction mixture was extracted with H2O, EA, and brine, followed by drying (Na2SO4), filtration, and concentration under reduced pressure, and the residue was purified by column chromatography (MeOH:MC=1:10), to give (S)-2-((6-(1-methyl-1H-pyrazol-4-yl)-1H-[1,2,3]triazolo[4,5-b]pyrazin-1-yl)methyl)-4-(5-(2-morpholinoethoxy)pyrimidin-2-yl)morpholine 5 mg (15%).

$^1$H-NMR (300 MHz, CDCl3) δ 8.91 (s, 1H), 8.17 (s, 1H), 8.12 (s, 1H), 8.11 (s, 2H), 4.95 (dd, J=7.5 Hz, J=14.1 Hz, 1H), 4.78 (dd, J=4.5 Hz, J=14.1 Hz, 1H), 4.61-4.51 (m, 1H), 4.33-4.21 (m, 2H), 4.10 (t, J=4.5 Hz, 2H), 4.02 (s, 3H), 4.00-3.93 (m, 1H), 3.76 (t, J=3.7 Hz, 4H), 3.58 (dt, J=2.8 Hz, J=11.4 Hz, 1H), 3.17-3.07 (m, 1H), 3.03 (dd, J=10.1 Hz, J=13.1 Hz, 1H), 2.79 (t, J=4.5 Hz, 2H), 2.64-2.54 (m, 4H)

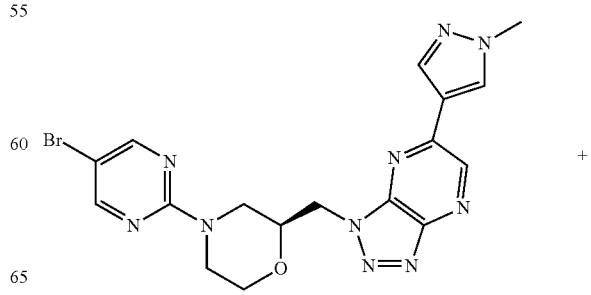

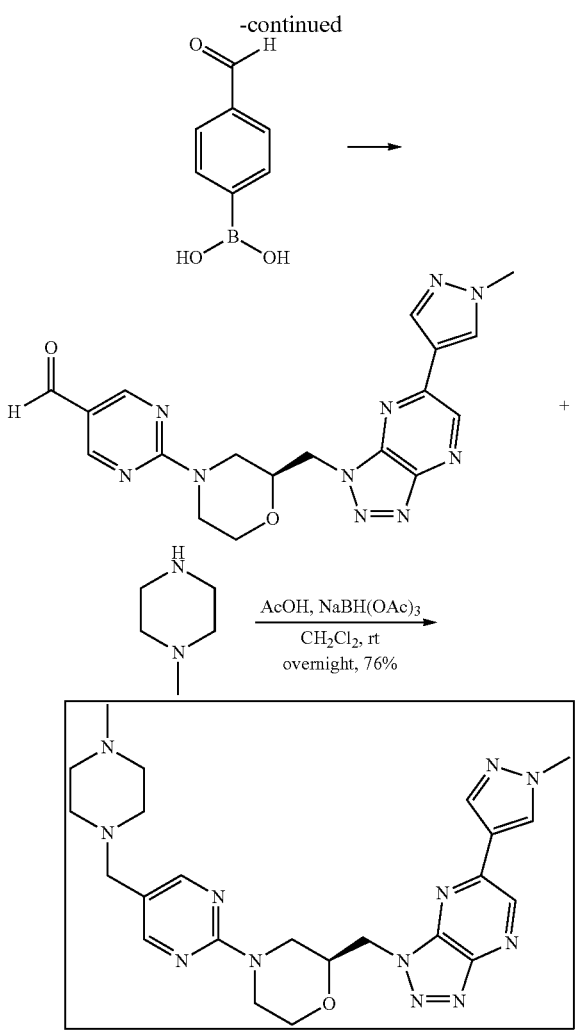

(S)-2-((6-(1-methyl-1H-pyrazol-4-yl)-1H-[1,2,3]triazolo[4,5-b]pyrazin-1-yl)methyl)-4-(5-((4-methylpiperazin-1-yl)methyl)pyrimidin-2-yl)morpholine (S)-2-(2-((6-(1-methyl-1H-pyrazol-4-yl)-1H-[1,2,3]triazolo[4,5-b]pyrazin-1-yl)methyl)morpholino)pyrimidine-5-carboaldehyde 16 mg(0.033 mmol) was dissolved in CH$_2$Cl$_2$ 2 ml, and 1-methylpiperazine 7.4 µl (0.066 mmol), AcOH 2.3 µl, and NaBH(OAc)$_3$ 11 mg (0.05 mmol) were added, followed by stirring at room temperature overnight. After the completion of the reaction, the reaction mixture was adjusted to pH 8 with aq. K$_2$CO$_3$ (5%), and extracted with H$_2$O, EA, and brine, followed by drying (Na$_2$SO$_4$), filtration, and concentration under reduced pressure. The residue was purified by column chromatography (MeOH:MC=1:10), to give (S)-2-((6-(1-methyl-1H-pyrazol-4-yl)-1H-[1,2,3]triazolo[4,5-b]pyrazin-1-yl)methyl)-4-(5-((4-methylpiperazin-1-yl)methyl)pyrimidin-2-yl)morpholine 14.1 mg, (76%).

$^1$H-NMR (300 MHz, CDCl$_3$) δ 8.91 (s, 1H), 8.55 (s, 2H), 8.17 (s, 1H), 8.12 (s, 1H), 7.46-7.35 (m, 4H), 4.96 (dd, J=7.5 Hz, J=14.1 Hz, 1H), 4.84 (dd, J=4.5 Hz, J=14.1 Hz, 1H), 4.81-4.74 (m, 1H), 4.52-4.41 (m, 1H), 4.34-4.23 (m, 1H), 4.01 (s, 3H), 4.01-3.95 (m, 1H), 3.63 (dt, J=2.5 Hz, J=11.5 Hz, 1H), 3.55 (s, 3H), 3.29-3.21 (m, 1H), 3.16 (dd, J=10.1 Hz, J=13.1 Hz, 1H), 2.59-2.38 (m, 8H), 2.31 (s, 3H)

3-(1-(((2S)-4-(5-(1-(2-((tetrahydro-2H-pyran-2-yl)oxy)ethyl)-1H-pyrazol-4-yl)pyrimidin-2-yl)morpholine-2-yl)methyl)-1H-[1,2,3]triazolo[4,5-b]pyrazin-6-yl)benzonitrile In a pressure tube reactor, (S)-3-(1-((4-(5-bromopyrimidin-2-yl)morpholine-2-yl)methyl)-1H-[1,2,3]-triazolo[4,5-b]pyrazin-6-yl)benzonitrile 50 mg (0.10 mmol) was added, and then potassium carbonate 43 mg (0.31 mmol) was added. Pd(dppf)$_2$Cl$_2$ 4 mg (0.005 mmol) was further added, 1,4-dioxane 2 ml and 1-(2-((tetrahydro-2H-pyran-2-yl)oxy)ethyl)-4-(4,4,5,5-tetramethyl-1,3,2-dioxaborolane-2-yl)-1H-pyrazole 40 mg (0.13 mmol) were added, and then H$_2$O 0.5 ml was added. The mixture was stirred at room temperature for 10 minutes under nitrogen gas, and then stirred at 80° C. for 2 hours. When the reaction was completed, the organic layer was extracted with ethyl acetate and water, and the extra water was removed by sodium sulfate, followed by concentration under reduced pressure. Column chromatography using 50% ethyl acetate/hexane gave 3-(1-(((2S)-4-(5-(1-(2-((tetrahydro-2H-pyran-2-yl)oxy)ethyl)-1H-pyrazol-4-yl)pyrimidin-2-yl)morpholine-2-yl)methyl)-1H-[1,2,3]triazolo[4,5-b]pyrazin-6-yl)benzonitrile 48 mg (0.08 mmol) with a yield of 70%.

$^1$H-NMR (300 MHz, CDCl$_3$) δ 9.23(s, 1H), 8.51(s, 1H), 8.45(s, 2H), 8.38(d, J=7.9 Hz 1H), 7.83(d, J=7.7 Hz, 1H), 7.69(d, J=7.5 Hz, 3H), 5.09-5.01 (m, 1H), 4.95-4.89(m, 1H), 4.76(d, J=12.9 Hz, 1H), 4.56 s, 1H), 4.45-4.26(m, 5H), 4.13-4.05(m, 2H), 4.00-3.96(m, 1H), 3.83-3.74(m, 2H), 4.00-3.96 (m, 1H), 3.83-3.74(m, 2H), 3.68-3.55(m, 3H), 3.74-3.43(m, 2H), 3.22-3.08(m, 2H), 2.09-2.04(m, 1H), 1.78-1.42(m, 9H), 1.31-1.23(m, 2H)

(S)-3-(1-((4-(5-(1-(2-hydroxyethyl)-1H-pyrazol-4-yl)pyrimidin-2-yl)morpholin-2-yl)methyl)-1H-[1,2,3]triazolo[4,5-b]pyrazin-6-yl)benzonitrile (Chemical Formula 31)

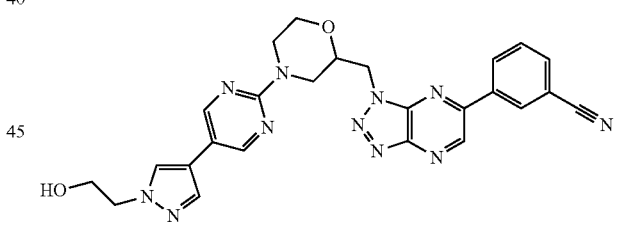

3-(1-(((2S)-4-(5-(1-(2-((tetrahydro-2H-pyran-2-yl)oxy)ethyl)-1H-pyrazol-4-yl)pyrimidin-2-yl)morpholine-2-yl)methyl)-1H-[1,2,3]triazolo[4,5-b]pyrazin-6-yl)benzonitrile 48 mg (0.08 mmol) was dissolved in MeOH ml, and 4M HCl in 1,4-dioxane (3 ml) was added, followed by stirring at room temperature for 13 hours. When the reaction was completed, the reaction mixture was concentrated under reduced pressure to remove a solvent, thereby obtaining (S)-3-(1-((4-(5-(1-(2-hydroxyethyl)-1H-pyrazol-4-yl)pyrimidin-2-yl)morpholine-2-yl)methyl)-1H-[1,2,3]triazolo[4,5-b]pyrazin-6-yl)benzonitrile 46 mg (0.084 mmol) with a yield of 100%.

$^1$H-NMR (300 MHz, CDCl$_3$) δ 9.23 (s, 1H), 8.51 (s, 1H), 8.45 (s, 2H), 8.38 (d, J=7.9 Hz 1H), 7.83 (d, J=7.7 Hz, 1H), 7.69 (d, J=7.5 Hz, 3H), 5.09-5.01 (m, 1H), 4.95-4.89 (m, 1H), 4.76 (d, J=12.9 Hz, 1H), 4.56 (s, 1H), 4.45-4.26 (m, 5H), 4.13-4.05 (m, 2H), 4.00-3.96 (m, 1H), 3.83-3.74(m, 2H), 4.00-3.96 (m, 1H), 3.83-3.74(m, 2H), 3.68-3.55 (m, 3H), 3.74-3.43 (m, 2H), 3.22-3.08 (m, 2H), 2.09-2.04 (m, 1H)

2-fluoro-5-(1-(((2S)-4-(5-(1-(2-((tetrahydro-2H-pyran-2-yl)oxy)ethyl)-1H-pyrazol-4-yl)-pyrimidin-2-yl)morpholine-2-yl)methyl)-1H-[1,2,3]triazolo[4,5-b]pyrazin-6-yl)benzonitrile In a pressure tube reactor, ((S)-5-(1-((4-(5-bromopyrimidin-2-yl)morpholine-2-yl)methyl)-1H-[1,2,3]triazolo[4,5-b]pyrazin-6-yl)-2-fluorobenzonitrile 50 mg (0.10 mmol) was added, and then potassium carbonate 41 mg (0.30 mmol) was added. Pd(dppf)$_2$Cl$_2$ 4 mg (0.005 mmol) was further added, followed by 1,4-dioxane ml, 1-(2-((tetrahydro-2H-pyran-2-yl)oxy)ethyl)-4-(4,4,5,5-tetra methyl-1,3,2-dioxaborolane-2-yl)-1H-pyrazole 38 mg (0.12 mmol) and then H$_2$O 0.5 ml. The mixture was stirred at room temperature for 10 minutes under nitrogen gas, and then stirred at 80° C. for 2 hours. When the reaction was completed, the organic layer was extracted with ethyl acetate and water, and the extra water was removed by sodium sulfate, followed by concentration under reduced pressure. Column chromatography using 60% ethyl acetate/hexane gave 2-fluoro-5-(1-(((2S)-4-(5-(1-(2-((tetrahydro-2H-pyran-2-yl)oxy)ethyl)-1H-pyrazol-4-yl)pyrimidin-2-yl)morpholine-2-yl)-methyl)-1H-[1,2,3]triazolo[4,5-b]pyrazin-6-yl)benzonitrile 49 mg (0.08 mmol) with a yield of 80%.

$^1$H-NMR (300 MHz, CDCl$_3$) δ 9.20(s, 1H), 8.51(d, J=5.8 Hz, 1H), 8.45-8.39(m, 3H), 7.69(d, J=7.9 Hz 2H), 7.57(s, 1H), 7.45(t, J=8.4 Hz, 1H), 5.07-5.00(m, 1H), 4.94-4.88(m, 1H), 4.76(d, J=13.0 Hz, 1H), 4.56(brs, 2H), 4.45-4.28(m, 5H), 4.15-4.06(m, 2H), 3.97(d, J=11.5 Hz, 1H), 3.83-3.74(m, 2H), 3.68-3.55(m, 2H), 3.47-3.44 (m, 1H), 3.23-3.07 (m, 2H), 2.04(s, 1H), 1.78-1.49(m, 9H), 1.25(t, J=7.2 Hz, 2H)

(S)-2-fluoro-5-(1-((4-(5-(1-(2-hydroxyethyl)-1H-pyrazol-4-yl)pyrimidin-2-yl)morpholine-2-yl)methyl)-1H-[1,2,3]triazolo[4,5-b]pyrazin-6-yl)benzonitrile (Chemical Formula 32)

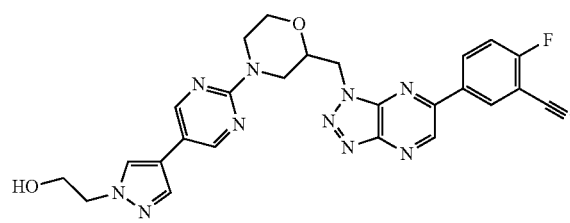

2-fluoro-5-(1-(((2S)-4-(5-(1-(2-((tetrahydro-2H-pyran-2-yl)oxy)ethyl)-1H-pyrazol-4-yl)pyrimidin-2-yl)morpholine-2-yl)-methyl)-1H-[1,2,3]triazolo[4,5-b]pyrazin-6-yl)benzonitrile 49 mg (0.08 mmol) was dissolved in MeOH 1 ml, and 4 M HCl dissolved in 1,4-dioxane 3 ml was added, followed by stirring at room temperature for 13 hours. When the reaction was completed, the reaction mixture was concentrated under reduced pressure to remove a solvent, thereby obtaining (S)-2-fluoro-5-(1-((4-(5-(1-(2-hydroxyethyl)-1H-pyrazol-4-yl)pyrimidin-2-yl)morpholine-2-yl)methyl)-1H-[1,2,3]triazolo[4,5-b]pyrazin-6-yl)benzonitrile 46 mg (0.084 mmol) with a yield of 100%.

$^1$H-NMR (300 MHz, CDCl$_3$) δ9.20(s, 1H), 8.51(d, J=5.8 Hz, 1H), 8.45-8.39(m, 3H), 7.69(d, J=7.9 Hz 2H), 7.57(s, 1H), 7.45(t, J=8.4 Hz, 1H), 5.07-5.00(m, 1H), 4.94-4.88(m, 1H), 4.76(d, J=13.0 Hz, 1H), 4.56(brs, 2H), 4.45-4.28(m, 5H), 4.15-4.06(m, 2H), 3.97(d, J=11.5 Hz, 1H), 3.83-3.74(m, 2H), 3.68-3.55(m, 2H), 3.47-3.44(m, 1H), 3.23-3.07(m, 2H)

(S)-tert-butyl4-(2-(2-((6-(3-cyano-4-fluorophenyl)-1H-[1,2,3]triazolo[4,5-b]pyrazin-1-yl)methyl)morpholino)pyrimidin-5-yl)-5,6-dihydropyridin-1(2H)-carboxylate In a pressure tube reactor, ((S)-5-(1-((4-(5-bromopyrimidin-2-yl)morpholine-2-yl)methyl)-1H-[1,2,3]triazolo[4,5-b]pyrazin-6-yl)-2-fluorobenzonitrile 100 mg (0.20 mmol) was added, and potassium carbonate 83 mg (0.60 mmol) was added. Pd(dppf)$_2$Cl$_2$ 8 mg (0.01 mmol) was further added, followed by 1,4-dioxane 3 ml, tert-butyl 4-(4,4,5,5-tetramethyl-1,3,2-dioxaborolane-2-yl)-5,6-dihydropyridine-1(2H)-carboxylate 74 mg (0.24 mmol), and H$_2$O 0.5 ml. The mixture was stirred at room temperature for 10 minutes under nitrogen gas, and then stirred at 80° C. for 2 hours. When the reaction was completed, the organic layer was extracted with ethyl acetate and water, and the extra water was removed by sodium sulfate, followed by concentration under reduced pressure. Column chromatography using 50% ethylacetate/hexane gave (S)-tert-butyl 4-(2-(2-((6-(3-cyano-4-fluorophenyl)-1H-[1,2,3]triazolo[4,5-b]pyrazin-1-yl)methyl)morpholino)pyrimidin-5-yl)-5,6-dihydropyridine-1(2H)-carboxylate 104 mg (0.17 mmol) with a yield of 87%.

$^1$H-NMR (300 MHz, CDCl$_3$) δ 9.19 (s, 1H), 8.50 (d, J=5.8 Hz, 1H), 8.41-8.36 (m, 3H), 7.44 (t, J=8.4 Hz, 1H), 5.06-4.99 (m, 1H), 4.92-4.86 (m, 1H), 4.77 (d, J=13.4 Hz, 1H), 4.44 (d, J=13.3 Hz, 1H), 4.26 (brs, 2H), 4.15-4.10 (m, 1H), 4.06 (brs, 2H), 3.96 (d, J=10.7 Hz, 1H), 3.65-3.61 (m, 2H), 3.57-3.53 (m, 1H), 3.20-3.06 (m, 2H), 2.43 (brs, 2H), 2.04 (s, 2H), 1.56 (s, 1H), 1.49 (s, 9H), 1.25 (t, J=7.1 Hz, 2H)

(S)-2-fluoro-5-(1-((4-(5-(1,2,3,6-tetrahydropyridin-4-yl)pyrimidin-2-yl)morpholine-2-yl)methyl)-1H-[1,2,3]triazolo[4,5-b]pyrazin-6-yl)benzonitrile (Chemical Formula 30)

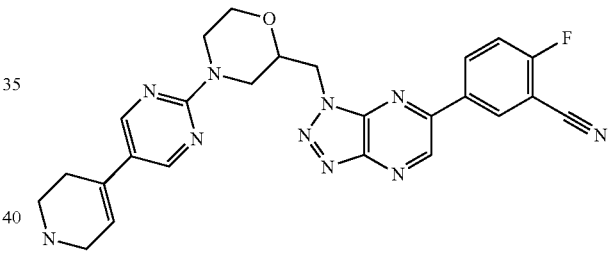

(S)-tert-butyl 4-(2-(2-((6-(3-cyano-4-fluorophenyl)-1H-[1,2,3]triazolo[4,5-b]pyrazin-1-yl)methyl)morpholino)pyrimidin-5-yl)-5,6-hydropyridine-1(2H)-carboxylate 104 mg (0.17 mmol) was dissolved in MeOH 1 ml, and 4 M HCl dissolved in 1,4-dioxane (3 mL) was added. The mixture was stirred at room temperature for 3 hours, and when the reaction was completed, the reaction mixture was concentrated under reduced pressure to remove a solvent, and then extracted two times with dichloromethane and NaHCO$_3$. The extra water was removed by sodium sulfate, followed by concentration under reduced pressure. Column chromatography using 5% dichloromethane/methanol gave (S)-2-fluoro-5-(1-((4-(5-(1,2,3,6-tetrahydropyridin-4-yl)pyrimidin-2-yl)morpholine-2-yl)methyl)-1H-[1,2,3]triazolo[4,5-b]pyrazin-6-yl)benzonitrile 44 mg (0.09 mmol) with a yield of 51%.

$^1$H-NMR (300 MHz, CDCl$_3$) δ 9.19 (s, 1H), 8.50 (d, J=5.8 Hz, 1H), 8.41-8.36 (m, 3H), 7.44 (t, J=8.4 Hz, 1H), 5.06-4.99 (m, 1H), 4.92-4.86 (m, 1H), 4.77 (d, J=13.4 Hz, 1H), 4.44 (d, J=13.3 Hz, 1H), 4.26 (brs, 2H), 4.15-4.10 (m, 1H), 4.06 (brs, 2H), 3.96 (d, J=10.7 Hz, 1H), 3.65-3.61 (m, 2H), 3.57-3.53

(m, 1H), 3.20-3.06 (m, 2H), 2.43 (brs, 2H), 2.04 (s, 2H), 1.56 (s, 1H), 1.25 (t, J=7.1 Hz, 2H)

(S)-2-fluoro-5-(1-((4-(5-(1-(2-hydroxyethyl)-1,2,3,6-tetrahydropyridin-4-yl)pyrimidin-2-yl)morpholine-2-yl)methyl)-1H-[1,2,3]triazolo[4,5-b]pyrazin-6-yl)benzonitrile (Chemical Formula 38)

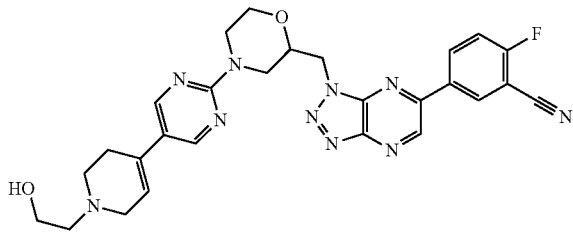 [SMILES: N#Cc1cc(-c2cnc3nnn(CC4CN(c5ncc(C6=CCN(CCO)CC6)cn5)CCO4)c3n2)ccc1F]

(S)-2-fluoro-5-(1-((4-(5-(1,2,3,6-tetrahydropyridin-4-yl)pyrimidin-2-yl)morpholine-2-yl)methyl)-1H-[1,2,3]triazolo[4,5-b]pyrazin-6-yl)benzonitrile 44 mg (0.09 mmol) was dissolved in DMF 1 ml. Potassium carbonate 36 mg (0.26 mmol) and 2-bromoethanol 0.009 ml (0.13 mmol) were added, and Et$_3$N (2 drop) were added, followed by stirring at room temperature for 13 hours under nitrogen gas. When the reaction was completed, the reaction mixture was extracted two times or more with ethyl acetate and water, and concentrated under reduced pressure. PCL using 10% dichloromethane/methanol gave (S)-2-fluoro-5-(1-((4-(5-(1-(2-hydroxyethyl)-1,2,3,6-tetrahydropyridin-4-yl)pyrimidin-2-yl)morpholin-2-yl)methyl)-1H-[1,2,3]triazolo[4,5-b]pyrazin-6-yl)benzonitrile 9 mg (0.017 mmol) with a yield of 19%.

$^1$H-NMR (300 MHz, CDCl$_3$) δ 9.19 (s, 1H), 8.50 (d, J=5.8 Hz, 1H), 8.40-8.37 (m, 3H), 7.44 (t, J=8.4 Hz, 1H), 5.06-4.97 (m, 1H), 4.92-4.86 (m, 1H), 4.76 (d, J=13.2 Hz, 1H), 4.43 (d, J=12.6 Hz, 1H), 4.26 (brs, 1H), 3.96 (d, J=10.9 Hz, 1H), 3.74-3.69 (m, 2H), 3.57 (t, J=11.0 Hz, 1H), 3.49 (s, 1H), 3.24 (brs, 2H), 3.17-3.06 (m, 2H), 3.82-3.27 (m, 2H), 2.71-2.68 (m, 2H), 2.50 (brs, 2H)

4-bromo-1-(bromomethyl)-2-fluorobenzene

NBS (1.07 g, 6.05 mmol) and AIBN (83 mg, 0.50 mmol) were dissolved in CCl$_4$ (10 mL), and 1-bromo-2-fluoro-4-methylbenzene (1 g, 5.04 mmol) was added, followed by heating at 100° C. under reflux for 13 hours. When the reaction was completed, the reaction mixture was cooled at room temperature, and the generated solid was filtered off, followed by extraction with CCl$_4$ and water two times or more. The organic layer was treated with sodium sulfate to remove extra water, followed by concentration under reduced pressure, to give 4-bromo-1-(bromomethyl)-2-fluorobenzene (1.2 g, 4.47 mmol) with a yield of 89%.

$^1$H-NMR (300 MHz, CDCl$_3$) δ 7.51-7.41 (m, 1H), 7.09 (d, J=9.0 Hz, 1H), 6.99 (d, J=8.2 Hz, 1H), 4.34 (s, 2H)

4-(4-bromo-2-fluorobenzyl)morpholine 4-bromo-1-(bromomethyl)-2-fluorobenzene (600 mg, 2.24 mmol) was dissolved in DMF (8 mL), and KI (400 mg, 2.46 mmol) was added and morpholine (0.78 mL, 8.96 mmol) was added, followed by stirring at 60° C. for 13 hours. When the reaction was completed, the reaction mixture was concentrated under reduced pressure to remove DMF, and extracted two times or more with ethyl acetate and brine. The organic layer was treated with sodium sulfate to remove extra water, and then concentrated under reduced pressure, followed by column chromatography using 30% ethyl acetate/hexane, to give 4-(4-bromo-2-fluorobenzyl)morpholine (278 mg, 1.01 mmol) with a yield of 45%.

$^1$H-NMR (300 MHz, CDCl$_3$) δ 7.47(t, J=7.2 Hz, 1H), 7.15(d, J=9.4 Hz, 1H), 6.99(d, J=8.0 Hz, 1H), 3.70(brs, 4H), 3.44(s, 2H), 2.43(brs, 4H)

4-(2-fluoro-4-(4,4,5,5-tetramethyl-1,3,2-dioxaborolane-2-yl)benzyl)morpholine

In a pressure tube reactor, 4,4,4',4',5,5,5',5'-octamethyl-2,2'-bi(1,3,2-dioxaborolane) (2.22 g, 8.75 mmol) was added, and Pd(dppf)$_2$Cl$_2$ (285 mg, 0.35 mmol) was added, followed by KOAC (2.28 g, 23.3 mmol) and DMF (20 mL). 4-(4-bromo-2-fluorobenzyl)morpholine (1.6 g, 5.83 mmol) was further added, and the mixture was stirred at 85° C. for 13 hours under nitrogen gas. When the reaction was completed, the reaction mixture was extracted two times or more with ethyl acetate and water, and the organic layer was treated with sodium sulfate to remove extra water, followed by concentration under reduced pressure. Column chromatography using 30% ethylacetate/hexane gave 4-(2-fluoro-4-(4,4,5,5-tetramethyl-1,3,2-dioxaborolane-2-yl)benzyl)morpholine (1.8 g, 5.6 mmol) with a yield of 96%.

$^1$H-NMR (300 MHz, CDCl$_3$) δ 7.47 (t, J=7.2 Hz, 1H), 7.15 (d, J=9.4 Hz, 1H), 6.99 (d, J=8.0 Hz, 1H), 3.70 (brs, 4H), 3.44 (s, 2H), 2.43 (brs, 4H), 1.35 (s, 12H)

(S)-2-fluoro-5-(1-((4-(5-(3-fluoro-4-(morpholinomethyl)phenyl)pyrimidin-2-yl)morpholine-2-yl)methyl)-1H-[1,2,3]triazolo[4,5-b]pyrazin-6-yl)benzonitrile (Chemical Formula 41)

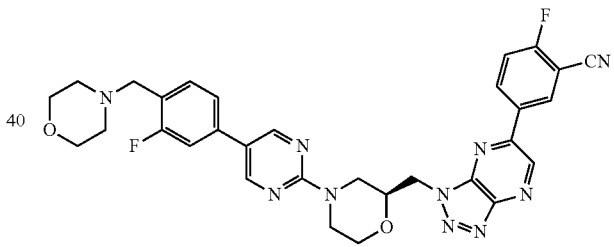

In a pressure tube reactor, ((S)-5-(1-((4-(5-bromopyrimidin-2-yl)morpholine-2-yl)methyl)-1H-[1,2,3]triazolo[4,5-b]pyrazin-6-yl)-2-fluorobenzonitrile (40 mg, 0.08 mmol) was added, and then K$_2$CO$_3$ (33 mg, 0.24 mmol) was added. Pd(dppf)$_2$Cl$_2$ (3 mg, 0.004 mmol) was further added, and then 1,4-dioxane (2 mL) and water (0.5 mL) were added. 4-(2-fluoro-4-(4,4,5,5-tetramethyl-1,3,2-dioxaborolane-2-yl)benzyl)morpholine (12 g, 0.13 mmol) was added, and then stirred at room temperature under nitrogen gas for 10 minutes, followed by stirring at 85° C. for 2 hours. When the reaction was completed, the organic layer was extracted with ethyl acetate and water, and the extra water was removed by sodium sulfate, followed by concentration under reduced pressure. Column chromatography using 5% dichloromethane/methanol gave (S)-2-fluoro-5-(1-((4-(5-(3-fluoro-4-(morpholinomethyl)phenyl)-pyrimidin-2-yl)morpholine-2-yl)methyl)-1H-[1,2,3]triazolo[4,5-b]pyrazin-6-yl)benzonitrile (46 mg, 0.075 mmol) with a yield of 46%.

$^1$H-NMR (300 MHz, CDCl$_3$) δ 9.19(s, 1H), 8.53-8.49(m, 2H), 8.45-8.38(m, 1H), 7.44(t, J=8.4 Hz, 1H), 7.33-7.26(m, 2H), 7.19-7.1 (m, 2H), 5.08-5.11(m, 1H), 4.94-4.88(m, 1H), 4.83(d, J=12.9 Hz, 1H), 4.50 (d, J=13.6 Hz, 1H), 4.29(brs, 1H), 4.15-4.08(m, 1H), 3.98 (d, J=11.7 Hz, 1H), 3.73(brs, 4H), 3.63-3.55(m, 1H), 3.52(s, 2H), 3.26-3.12(m, 2H), 2.47 (brs, 4H)

(S)-4-(5-(3-fluoro-4-(morpholinomethyl)phenyl) pyrimidin-2-yl)-2-((6-(1-methyl-1H-pyrazol-4-yl)-1H-[1,2,3]triazolo[4,5-b]pyrazin-1-yl)methyl)morpholine (Chemical Formula 42)

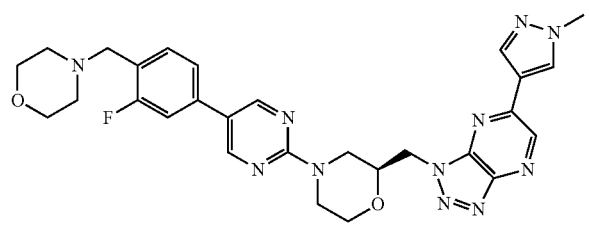 [SMILES: Cn1cc(-c2cnc3nnn(C[C@@H]4CN(c5ncc(-c6ccc(CN7CCOCC7)c(F)c6)cn5)CCO4)c3n2)cn1]

In a pressure tube reactor, (S)-4-(5-bromopyrimidin-2-yl)-2-((6-(1-methyl-1H-pyrazol-4-yl)-1H-[1,2,3]triazolo[4,5-b]pyrazin-1-yl)methyl)morpholine (40 mg, 0.08 mmol) was added, and then K$_2$CO$_3$ (36 mg, 0.26 mmol) was added. Pd(dppf)$_2$Cl$_2$ (4 mg, 0.004 mmol) was further added, and 1,4-dioxane (2 mL) and water (0.5 mL) were added. 4-(2-fluoro-4-(4,4,5,5-tetramethyl-1,3,2-dioxaborolane-2-yl) benzyl)morpholine (42 mg, 0.13 mmol) was added, and then stirred at room temperature under nitrogen gas for 10 minutes, followed by stirring at 85° C. for 2 hours. When the reaction was completed, the organic layer was extracted with ethyl acetate and water, and the extra water was removed by sodium sulfate, followed by concentration under reduced pressure. Column chromatography using 50% ethyl acetate/hexane gave (S)-4-(5-(3-fluoro-4-(morpholinomethyl)phenyl)pyrimidin-2-yl)-2-((6-(1-methyl-1H-pyrazol-4-yl)-1H-[1,2,3]triazolo[4,5-b]pyrazin-1-yl)methyl)morpholine (51 mg, 0.089 mmol) with a yield of 46%.

$^1$H-NMR (300 MHz, CDCl$_3$) δ 8.91 (s, 1H), 8.52 (s, 1H), 8.15 (d, J=8.4 Hz, 1H), 7.32-7.26 (m, 2H), 7.20-7.16 (m, 2H), 5.08-4.92 (m, 1H), 4.84-4.76 (m, 2H), 4.49 (d, J=12.9 Hz, 1H), 4.28 (brs, 1H), 4.02 (s, 3H), 3.74-3.71 (m, 4H), 3.64-3.56 (m, 1H), 3.51 (s, 2H), 3.27-3.10 (m, 2H), 2.47 (brs, 4H)

2-fluoro-4-(4,4,5,5-tetramethyl-1,3,2-dioxaborolane-2-yl)benzaldehyde

In a pressure tube reactor, 4-bromo-2-fluorobenzaldehyde (500 mg, 2.46 mmol) and 4,4,4',4',5,5,5',5'-octamethyl-2,2'-bi(1,3,2-dioxaborolane) (938 mg, 3.69 mmol) were added, and then Pd(dppf)$_2$Cl$_2$ (120 mg, 0.15 mmol) was added. dppf (78 mg, 0.15 mmol) and KOAc (965 mg, 9.84 mmol) were further added, and 1,4-dioxane (8 mL) was added, followed by stirring at 85° C. under nitrogen gas for 13 hours. When the reaction was completed, the reaction mixture was extracted two times or more with ethyl acetate and water, and the organic layer was treated with sodium sulfate to remove extra water. After concentration under reduced pressure, column chromatography using 20% ethyl acetate/hexane gave 2-fluoro-4-(4,4,5,5-tetramethyl-1,3,2-dioxaborolane-2-yl) benzaldehyde with a yield of 96%.

$^1$H-NMR (300 MHz, CDCl$_3$) δ 10.38 (s, 1H), 7.85-7.81 (m, 1H), 7.67-7.65 (m, 1H), 7.57 (s, J=10.4 Hz, 1H), 1.35 (s, 12H)

(S)-2-fluoro-5-(1-((4-(5-(3-fluoro-4-formylphenyl) pyrimidin-2-yl)morpholin-2-yl)methyl)-1H-[1,2,3] triazolo[4,5-b]pyrazin-6-yl)benzonitrile In a pressure tube reactor, ((S)-5-(1-((4-(5-bromopyrimidin-2-yl)morpholine-2-yl)methyl)-1H-[1,2,3]triazolo[4,5-b]pyrazin-6-yl)-2-fluorobenzonitrile (50 mg, 0.10 mmol) was added, and then 1M Na$_2$CO$_3$ (0.31 mL, 0.31 mmol) was added. Pd(PPh$_3$)$_4$ (6 mg, 0.005 mmol) was further added, and 1,4-dioxane (1 mL) and 2-fluoro-4-(4,4,5,5-tetramethyl-1,3,2-dioxaborolane-2-yl)benzaldehyde (38 mg, 0.15 mmol) were added. The mixture was stirred at room temperature for 10 minutes under nitrogen gas, and then stirred at 105° C. for 3 hours. When the reaction was completed, the organic layer was extracted with ethyl acetate and water, and the extra water was removed by sodium sulfate, followed by concentration under reduced pressure. Solid was generated using ether and hexane, followed by filtration, to give (S)-2-fluoro-5-(1-((4-(5-(3-fluoro-4-formylphenyl)pyrimidin-2-yl)morpholin-2-yl)methyl)-1H-[1,2,3]triazolo[4,5-b]pyrazin-6-yl)benzonitrile (49 mg, 0.091 mmol) with a yield of 90%.

$^1$H-NMR (300 MHz, CDCl$_3$) δ 10.36 (s, 1H), 9.19 (s, 1H), 8.53-8.45 (m, 1H), 8.61 (s, 2H), 7.97-7.92 (m, 1H), 7.49-7.39 (m, 3H), 5.08-5.01 (m, 1H), 4.94-4.88 (m, 1H), 4.56 (d, J=12.9 Hz, 1H), 4.27 (brs, 1H), 4.01-3.93 (m, 1H), 3.67-3.56 (m, 1H), 3.27-3.09 (m, 2H)

(S)-2-fluoro-5-(1-((4-(5-(3-fluoro-4-((4-methylpiperazin-1-yl)methyl)phenyl)pyrimidin-2-yl)morpholine-2-yl)methyl)-1H-[1,2,3]triazolo[4,5-b]pyrazin-6-yl) benzonitrile (Chemical Formula 39)

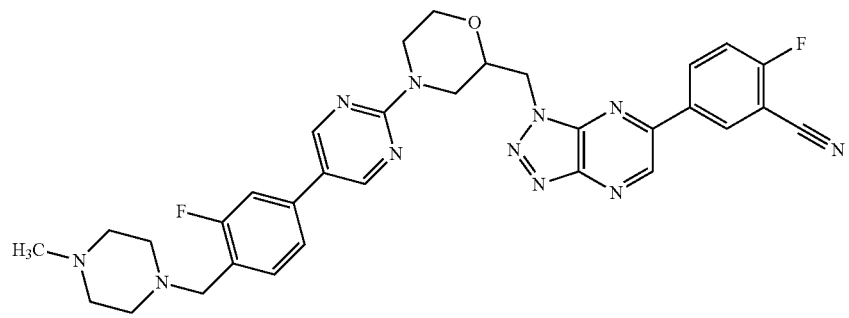 [SMILES: CN1CCN(Cc2ccc(-c3cnc(N4CCOC(Cn5nnc6ncc(-c7ccc(F)c(C#N)c7)nc65)C4)nc3)cc2F)CC1]

S)-2-fluoro-5-(1-((4-(5-(3-fluoro-4-formylphenyl)pyrimidin-2-yl)morpholine-2-yl)methyl)-1H-[1,2,3]triazolo[4,5-b]pyrazin-6-yl)benzonitrile (49 mg, 0.09 mmol) was dissolved in dichloromethane (3 mL), and then AcOH (0.006 mL, 0.11 mmol) and 1-methylpiperazine (0.011 mL, 0.10 mmol) were added. The mixture was stirred at room temperature for 30 minutes, and then NaBH(OAC)$_3$ (29 mg, 0.14 mmol) was added, followed by stirring at room temperature for 13 hours. When the reaction was completed, the reaction mixture was adjusted to pH 8 with 5% K$_2$CO$_3$, followed by extraction with dichloromethane and water two times or more. The organic layer was extracted with ethyl acetate and water, and the extra water was removed by sodium sulfate, followed by concentration under reduced pressure. PLC using 10% dichloromethane/methanol gave (S)-2-fluoro-5-(1-((4-(5-(3-fluoro-4-((4-methylpiperazin-1-yl)methyl)phenyl)pyrimidin-2-yl)morpholine-2-yl)methyl)-1H-[1,2,3]triazolo[4,5-b]pyrazin-6-yl)benzonitrile (24 mg, 0.038 mmol) with a yield of 45%.

¹H-NMR (300 MHz, CDCl₃) δ 9.19 (s, 1H), 8.54-8.50 (m, 3H), 8.43-8.38 (m, 1H), 7.49-7.41 (m, 1H), 7.22 (d, J=8.04 Hz, 2H), 7.14 (d, J=10.8 Hz, 1H), 5.08-5.01 (m, 1H), 4.94-4.81 (m, 2H), 4.50 (d, J=12.9 Hz, 1H), 4.30 (brs, 1H), 3.98 (d, J=10.8 Hz, 1H), 3.63-3.55 (m, 3H), 3.28-3.11 (m, 2H), 2.54 (brs, 8H), 2.30 (s, 3H)

(S)-2-fluoro-4-(2-(2-((6-(1-methyl-1H-pyrazol-4-yl)-1H-[1,2,3]triazolo[4,5-b]pyrazin-1-yl)methyl)morpholino)pyrimidin-5-yl)benzaldehyde In a pressure tube reactor, (S)-4-(5-bromopyrimidin-2-yl)-2-((6-(1-methyl-1H-pyrazol-4-yl)-1H-[1,2,3]triazolo[4,5-b]pyrazin-1-yl)methyl)morpholine (50 mg, 0.11 mmol) was added, and then 1M Na₂CO₃ (0.33 mL, 0.33 mmol) was added. Pd(PPh₃)₄ (6 mg, 0.005 mmol) was further added, and then 1,4-dioxane (1 mL) and 2-fluoro-4-(4,4,5,5-tetramethyl-1,3,2-dioxaborolane-2-yl)benzaldehyde (41 mg, 0.16 mmol) were added. The mixture was stirred at room temperature for 10 minutes under nitrogen gas, and then stirred at 105° C. for 13 hours. When the reaction was completed, the organic layer was extracted with ethyl acetate and water, and the extra water was removed by sodium sulfate, followed by concentration under reduced pressure. Solid was generated using ether and hexane, followed by filtration, to give (S)-2-fluoro-4-(2-(2-((6-(1-methyl-1H-pyrazol-4-yl)-1H-[1,2,3]triazolo[4,5-b]pyrazin-1-yl)-methyl)morpholino)pyrimidin-5-yl)benzaldehyde (41 mg, 0.087 mmol) with a yield of 76%.

¹H-NMR (300 MHz, CDCl₃) δ 10.36 (s, 1H), 8.92 (s, 1H), 8.59 (s, 2H), 8.17 (s, 1H), 8.12 (s, 1H), 7.94 (t, J=7.56 Hz, 1H), 7.36 (d, J=8.1 Hz, 1H), 4.99-4.92 (m, 1H), 4.85-4.79 (m, 1H), 4.54 (d, J=12.9 Hz, 1H), 4.27 (brs, 1H), 4.02 (s, 3H), 3.64-3.56 (m, 1H), 3.28-3.13 (m, 2H)

(S)-4-(5-(3-fluoro-4-((4-methylpiperazin-1-yl)methyl)phenyl)pyrimidin-2-yl)-2-((6-(1-methyl-1H-pyrazol-4-yl)-1H-[1,2,3]triazolo[4,5-b]pyrazin-1-yl)methyl)morpholine (Chemical Formula 40)

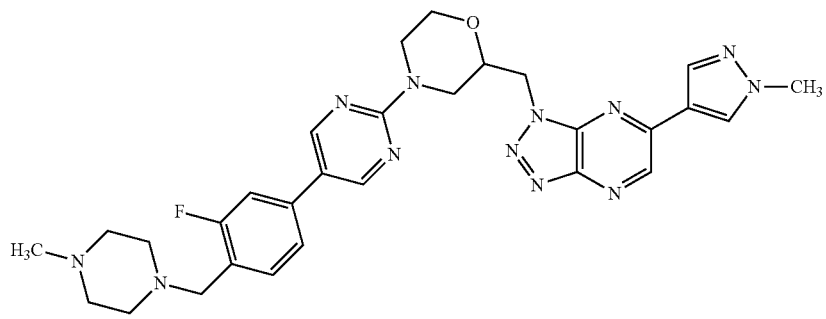

(S)-2-fluoro-4-(2-(2-((6-(1-methyl-1H-pyrazol-4-yl)-1H-[1,2,3]triazolo[4,5-b]pyrazin-1-yl)-methyl)morpholino)pyrimidin-5-yl)benzaldehyde (41 mg, 0.09 mmol) was dissolved in dichloromethane (3 mL), and then AcOH (0.006 mL, 0.10 mmol) and 1-methylpiperazine (0.02 mL, 0.17 mmol) were added. The mixture was stirred at room temperature for 30 minutes, and then NaBH(OAc)₃ (28 mg, 0.13 mmol) was added, followed by stirring at room temperature for 13 hours. When the reaction was completed, the reaction mixture was adjusted to pH 8 with 5% K₂CO₃, followed by extraction with dichloromethane and water two times or more. The organic layer was extracted with ethyl acetate and water, and the extra water was removed by sodium sulfate, followed by concentration under reduced pressure. PLC using 10% dichloromethane/methanol gave (S)-4-(5-(3-fluoro-4-((4-methylpiperazin-1-yl)methyl)phenyl)pyrimidin-2-yl)-2-((6-(1-methyl-1H-pyrazol-4-yl)-1H-[1,2,3]triazolo[4,5-b]pyrazin-1-yl)methyl)morpholine (20 mg, 0.034 mmol) with a yield of 46%.

¹H-NMR (300 MHz, CDCl₃) δ 8.92 (s, 1H), 8.52 (s, 2H), 8.17 (s, 1H), 8.12 (s, 1H), 7.21 (t, J=7.56 Hz, 1H), 7.13 (d, J=8.1 Hz, 1H), 4.85-4.75 (m, 2H), 4.49 (d, J=12.9 Hz, 1H), 4.27 (brs, 1H), 4.02 (s, 3H), 3.64-3.56 (m, 1H), 3.28-3.13 (m, 2H), 2.53 (brs, 8H), 2.30 (s, 3H)

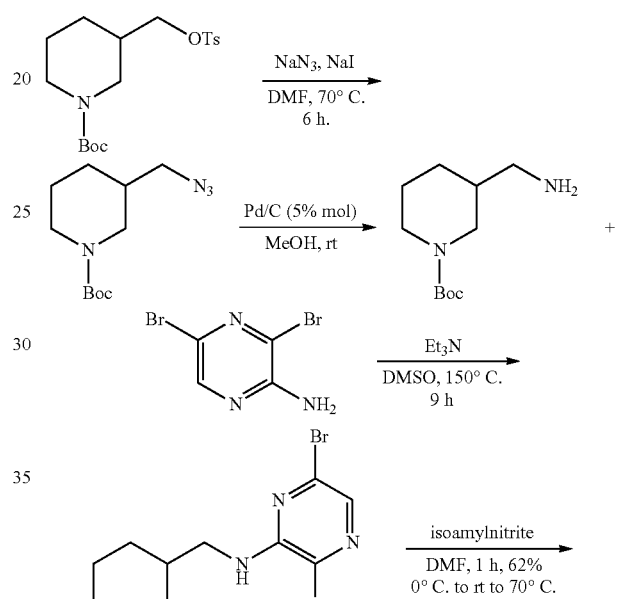

-continued

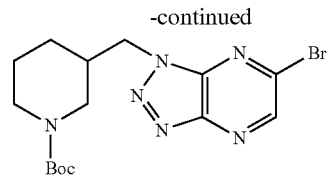

-continued

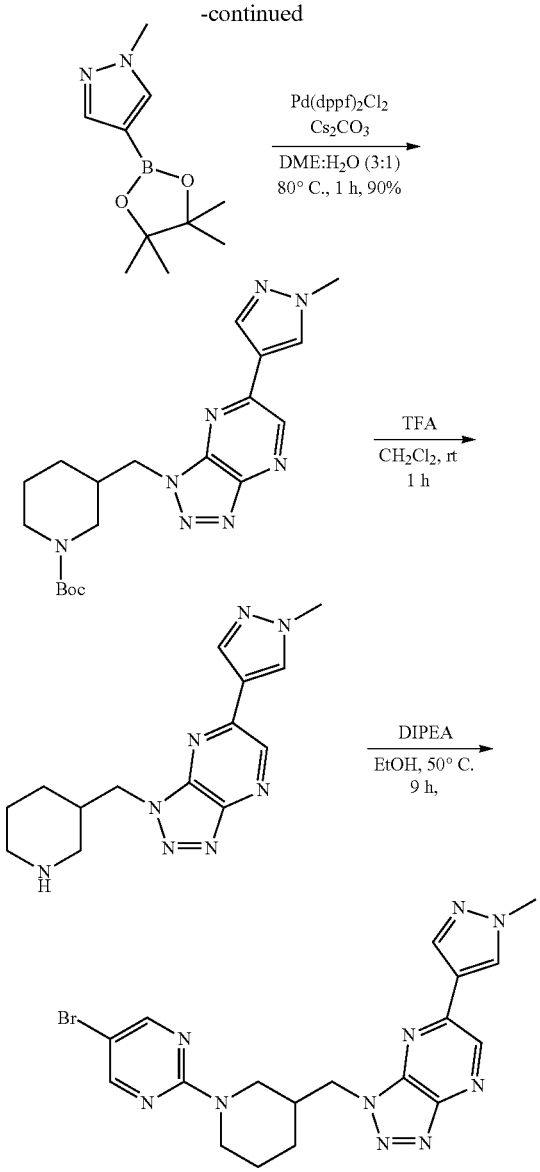

tert-butyl 3-(azidomethyl)piperidine-1-carboxylate tert-butyl 3-((tosyloxy)methyl)piperidine-1-carboxylate (8.85 g, 24 mmol) was dissolved in DMF (100 ml), and then NaN$_3$ (6.24 g, 96 mmol) and NaI (0.36 g, 2.40 mmol) were added, followed by stirring at 70° C. for hours. After the completion of the reaction, the reaction mixture was extracted with H$_2$O, EA, and brine, followed by drying (Na$_2$SO$_4$), filtration, and concentration under reduced pressure, and the residue was purified by column chromatography (EA:Hex=1:10), to give tert-butyl 3-(azidomethyl)piperidine-1-carboxylate (5.38 g, 92%).
$^1$H-NMR (300 MHz, CDCl$_3$) δ 4.09-3.82(m, 2H), 3.27-3.16(m, 2H), 2.95-2.54(m, 2H), 1.88-1.62(m, 3H), 1.52-1.42 (m, 1H), 1.47(s, 9H), 1.30-1.20(m, 1H)

tert-butyl 3-(aminomethyl)piperidine-1-carboxylate tert-butyl 3-(azidomethyl)piperidine-1-carboxylate (5.38 g, 22.40 mmol) was dissolved in MeOH (50 ml), and then Pd/C (5% mol) was added, followed by stirring under H$_2$ (gas) for 9 hours. After the completion of the reaction, the reaction mixture was filtered through celite, followed by filtration and concentration under reduced pressure, and then the next reaction was advanced without purification.
$^1$H-NMR (300 MHz, CDCl$_3$) δ 4.02-3.73 (m, 2H), 2.94-2.73 (m, 1H), 2.72-2.33 (m, 3H), 1.90-1.02 (m, 5H), 1.44 (s, 9H)

tert-butyl3-(((3-amino-6-bromopyrazin-2-yl)amino) methyl)piperidine-1-carboxylate tert-butyl 3-(aminomethyl)piperidine-1-carboxylate (4.97 g, 22.40 mmol) was dissolved in DMSO (80 ml), and then 3,5-dibromopyrazine-2-amine (8.5 g, 33.60 mmol) and Et$_3$N (6.3 ml) were added, followed by stirring at 130° C. overnight. After the completion of the reaction, the reaction mixture was extracted with H$_2$O, EA, and brine, followed by drying (Na$_2$SO$_4$), filtration, and concentration under reduced pressure, and the residue was purified by column chromatography (EA:Hex=1:1), to give tert-butyl 3-(((3-amino-6-bromopyrazine-2-yl)amino)methyl)piperidine-1-carboxylate (2.19 g, two steps: 26%).
$^1$H-NMR (300 MHz, CDCl$_3$) δ 7.39 (s, 1H), 4.64-4.23 (m, 2H), 3.79-2.92 (m, 5H), 2.25-1.19 (m, 4H), 1.46 (s, 9H)

tert-butyl 3-((6-bromo-1H-[1,2,3]triazolo[4,5-b] pyrazin-1-yl)methyl)piperidine-1-carboxylate tert-butyl 3-(((3-amino-6-bromopyrazine-2-yl)amino)methyl)piperidine-1-carboxylate (2.19 g, 5.70 mmol) was dissolved in DMF (15 ml), and isoamylnitrile (0.92 ml, 6.84 mmol) was slowly dropped at 0° C. After that, the mixture was stirred at 70° C. for 1 hour. After the completion of the reaction, the reaction mixture was extracted with H$_2$O, EA, and brine, followed by drying (Na$_2$SO$_4$), filtration, and concentration under reduced pressure, and the residue was purified by column chromatography (EA:Hex=1:8), to give tert-butyl 3-((6-bromo-1H-[1,2,3]triazolo[4,5-b]pyrazin-1-yl)methyl)piperidine-1-carboxylate (1.39 g, 62%).
$^1$H-NMR (300 MHz, CDCl$_3$) δ 8.78 (s, 1H), 4.63 (q, J=7.3 Hz, J=14.1 Hz, 2H), 3.96-3.67 (m, 2H), 3.05-2.74 (m, 2H), 2.47-2.31 (m, 1H), 1.81-1.67 (m, 2H), 1.56-1.14 (m, 2H), 1.40 (s, 9H)

tert-butyl 3-((6-(1-methyl-1H-pyrazol-4-yl)-1H-[1,2, 3]triazolo[4,5-b]pyrazin-1-yl)methyl)piperidine-1-carboxylate tert-butyl 3-((6-bromo-1H-[1,2,3]triazolo[4,5-b]pyrazin-1-yl)methyl)piperidine-1-carboxylate (0.5 g, 1.26 mmol), 1-methyl-4-(4,4,5,5-tetramethyl-1,3,2-dioxaborolane-2-yl)-1H-pyrazole (0.32 g, 1.51 mmol), Pd (dppf)$_2$Cl$_2$ (82 mg, 0.06 mmol), and Cs$_2$CO$_3$ (1.24 g, 3.78 mmol) were dissolved in DME (3 ml)+H$_2$O (1 ml), and the mixture was degassed with N$_2$, followed by stirring at 80° C. After the completion of the reaction, the reaction mixture was extracted with H$_2$O, EA, and brine, followed by drying (Na$_2$SO$_4$), filtration, and concentration under reduced pressure, and the residue was purified by column chromatography (EA:Hex=1:1), to give, tert-butyl 3-((6-(1-methyl-1H-pyrazol-4-yl)-1H-[1,2,3]triazolo [4,5-b]pyrazin-1-yl)methyl)piperidine-1-carboxylate (0.45 g, 89%).
$^1$H-NMR (300 MHz, CDCl$_3$) δ 8.87 (s, 1H), 8.17-8.07(m, 2H), 4.59(q, J=7.3 Hz, J=14.1 Hz, 2H), 4.00(s, 3H), 3.96-3.68 (m, 2H), 3.06-2.69(m, 2H), 2.45-2.27(m, 1H), 1.82-1.62(m, 2H), 1.53-1.17(m, 2H), 1.36(s, 9H)

6-(1-methyl-1H-pyrazol-4-yl)-1-(piperidin-3-ylmethyl)-1H-[1,2,3]triazolo[4,5-b]pyrazine 3-((6-(1-methyl-1H-pyrazol-4-yl)-1H-[1,2,3]triazolo[4,5-b]pyrazin-1-yl)methyl)piperidine-1-carboxylate (0.45 g, 0.89 mmol) was dissolved in CH$_2$Cl$_2$ (5 ml), and then TFA (5 ml) was added, followed by stirring at room temperature overnight. After the completion of the reaction, the reaction mixture was concentrated under reduced pressure, and the next reaction was advanced without purification.

1-((1-(5-bromopyrimidin-2-yl)piperidin-3-yl)methyl)-6-(1-methyl-1H-pyrazol-4-yl)-1H-[1,2,3]triazolo[4,5-b]pyrazine (Chemical Formula 3)

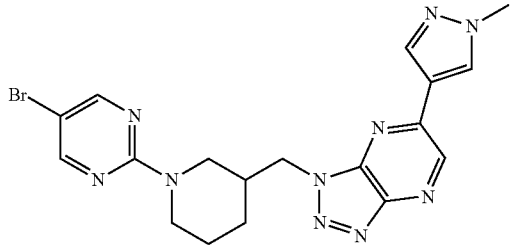 [SMILES: Cn1cc(-c2cnc3nnn(CC4CCCN(c5ncc(Br)cn5)C4)c3n2)cn1]

6-(1-methyl-1H-pyrazol-4-yl)-1-(piperidin-3-ylmethyl)-1H-[1,2,3]triazolo[4,5-b]pyrazine (0.26 g, 0.89 mmol) was dissolved in EtOH (15 ml), and then 5-bromo-2-chloropyrimidine (0.33 g, 1.33 mmol) and DIPEA (0.77 ml, 4.43 mmol) were added, followed by stirring at 50° C. overnight. After the completion of the reaction, the reaction mixture was extracted with H$_2$O, EA, and brine, followed by drying (Na$_2$SO$_4$), filtration, and concentration under reduced pressure, and the residue was purified by column chromatography (EA:Hex=1:1), to give (1-((1-(5-bromopyrimidin-2-yl)piperidin-3-yl)methyl)-6-(1-methyl-1H-pyrazol-4-yl)-1H-[1,2,3]triazolo[4,5-b]pyrazine (0.28 g, 70%).

$^1$H-NMR (300 MHz, CDCl$_3$) δ 8.92 (s, 1H), 8.19 (s, 2H), 8.15 (s, 1H), 8.08 (s, 1H), 4.78 (dd, J=6.9 Hz, J=13.8 Hz, 1H), 4.64 (dd, J=6.9 Hz, J=13.8 Hz, 1H), 4.34 (dd, J=3.7 Hz, J=13.3 Hz, 1H), 4.22 (dt, J=3.7 Hz, J=13.3 Hz, 1H), 4.05 (s, 3H), 3.40-3.32 (m, 1H), 3.23 (dd, J=9.0 Hz, J=13.3 Hz, 1H), 2.59-2.50 (m, 1H), 1.91-1.82 (m, 2H), 1.62-1.44 (m, 2H)

tert-butyl 4-(2-(3-((6-(1-methyl-1H-pyrazol-4-yl)-1H-[1,2,3]triazolo[4,5-b]pyrazin-1-yl)methyl)piperidin-1-yl)pyrimidin-5-yl)-5,6-dihydropyridine-1(2H)-carboxylate 1-((1-(5-bromopyrimidin-2-yl)piperidin-3-yl)methyl)-6-(1-methyl-1H-pyrazol-4-yl)-1H-[1,2,3]triazolo[4,5-b]pyrazine (0.2 g, 0.44 mmol), 1-methyl-4-(4,4,5,5-tetramethyl-1,3,2-dioxaborolane-2-yl)-1,2,3,6-tetrahydro pyridine (0.17 g, 0.53 mmol), Pd(dppf)$_2$Cl$_2$ (18 mg, 0.02 mmol), and K$_2$CO$_3$ (0.19 g, 1.32 mmol) were dissolved in dioxane (4 ml)+H$_2$O (1 ml), and then the mixture was degassed with N$_2$ (gas), followed by stirring at 80° C. for 2 hours. After the completion of the reaction, the reaction mixture was extracted with H$_2$O, EA, and brine, followed by drying (Na$_2$SO$_4$), filtration, and concentration under reduced pressure, and the residue was purified by column chromatography (EA:Hex=1:1), to give tert-butyl 4-(2-(3-((6-(1-methyl-1H-pyrazol-4-yl)-1H-[1,2,3]triazolo[4,5-b]pyrazin-1-yl)methyl)piperidin-1-yl)pyrimidin-5-yl)-5,6-dihydropyridine-1(2H)-carboxylate (0.2 g, 82%).

$^1$H-NMR (300 MHz, CDCl$_3$) δ 8.91 (s, 1H), 8.26 (s, 2H), 8.14 (s, 1H), 8.08 (s, 1H), 5.89-5.82 (m, 1H), 4.79 (dd, J=6.9 Hz, J=13.8 Hz, 1H), 4.65 (dd, J=6.9 Hz, J=13.8 Hz, 1H), 4.44 (dd, J=3.7 Hz, J=13.3 Hz, 1H), 4.30 (dt, J=3.7 Hz, J=13.3 Hz, 1H), 4.08-4.04 (m, 2H), 4.03 (s, 3H), 3.63 (t, J=4.7 Hz, 2H), 3.40-3.33 (m, 1H), 3.25 (dd, J=9.0 Hz, J=13.3 Hz, 1H), 2.59-2.51 (m, 1H), 2.42-2.35 (m, 2H), 1.92-1.82 (m, 2H), 1.71-1.43 (m, 2H), 1.51 (s, 9H)

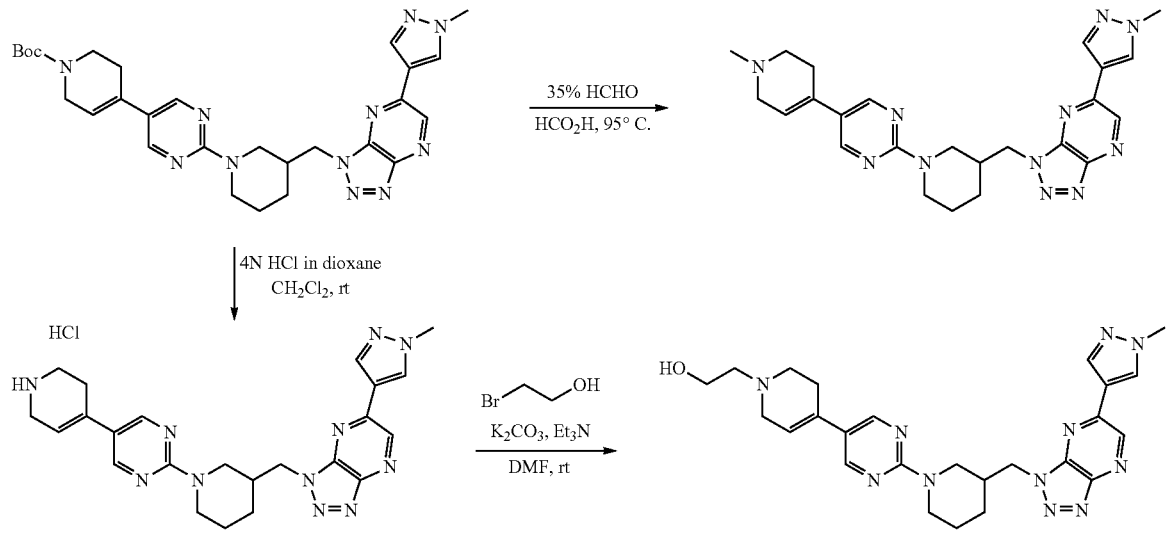

1-((1-(5-(1-methyl-1,2,3,6-tetrahydropyridin-4-yl)pyrimidin-2-yl)piperidin-3-yl)methyl)-6-(1-methyl-1H-pyrazol-4-yl)-1H-[1,2,3]triazolo[4,5-b]pyrazine (Chemical Formula 34)

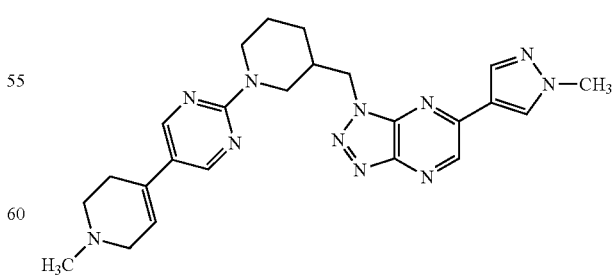

tert-butyl 4-(2-(3-((6-(1-methyl-1H-pyrazol-4-yl)-1H-[1,2,3]triazolo[4,5-b]pyrazin-1-yl)methyl)piperidin-1-yl)pyrimidin-5-yl)-5,6-dihydropyridine-1(2H)-carboxylate (71 mg, 0.13 mmol) was dissolved in 35% HCHO (0.2 ml)+HCO$_2$H (1 ml), followed by stirring at 95° C. overnight. After the completion of the reaction, the reaction mixture was adjusted to pH 11-12 with NaOH (aq.), and extracted with H$_2$O, EA, and brine, followed by drying (Na$_2$SO$_4$), filtration, and concentration under reduced pressure, and the residue was purified by column chromatography (MeOH:MC=1:10), to give (1-((1-(5-(1-methyl-1,2,3,6-tetrahydro pyridin-4-yl)pyrimidin-2-yl)piperidin-3-yl)methyl)-6-(1-methyl-1H-pyrazol-4-yl)-1H-[1,2,3]triazolo[4,5-b]pyrazine (10 mg, 16%).

$^1$H-NMR (300 MHz, CDCl$_3$) δ 8.92 (s, 1H), 8.28 (s, 2H), 8.15 (s, 1H), 8.08 (s, 1H), 5.91-5.88 (m, 1H), 4.79 (dd, J=6.9 Hz, J=13.8 Hz, 1H), 4.65 (dd, J=6.9 Hz, J=13.8 Hz, 1H), 4.44 (dd, J=3.7 Hz, J=13.3 Hz, 1H), 4.30 (dt, J=3.7 Hz, J=13.3 Hz, 1H), 4.03 (s, 3H), 3.39-3.32 (m, 1H), 3.24 (dd, J=9.0 Hz, J=13.3 Hz, 1H), 3.13-3.07 (m, 2H), 2.66 (t, J=5.3 Hz, 2H), 2.59-2.50 (m, 1H), 2.49-2.43 (m, 2H), 2.42 (s, 3H), 1.91-1.41 (m, 4H)

6-(1-methyl-1H-pyrazol-4-yl)-1-((1-(5-(1,2,3,6-tetrahydropyridin-4-yl)pyrimidin-2-yl)piperidin-3-yl)methyl)-1H-[1,2,3]triazolo[4,5-b]pyrazinehydrochloride (Chemical Formula 33)

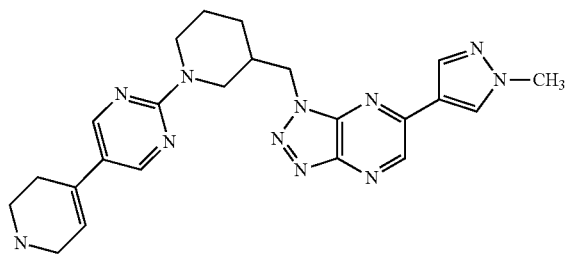 [SMILES: Cn1cc(-c2cnc3nnn(CC4CCCN(c5ncc(C6=CCNCC6)cn5)C4)c3n2)cn1]

1-((1-(5-(1-methyl-1,2,3,6-tetrahydropyridin-4-yl)pyrimidin-2-yl)piperidin-3-yl)methyl)-6-(1-methyl-1H-pyrazol-4-yl)-1H-[1,2,3]triazolo[4,5-b]pyrazine (125 mg, 0.22 mmol) was dissolved in CH$_2$Cl$_2$ (5 ml), and then 4 N HCl dissolved in dioxane (1 ml) was added, followed by stirring at room temperature. After the reaction was completed, the reaction mixture was concentrated under reduced pressure, and then purified with ether, to give 6-(1-methyl-1H-pyrazol-4-yl)-1-((1-(5-(1,2,3,6-tetrahydropyridin-4-yl)pyrimidin-2-yl)piperidin-3-yl)methyl)-1H-[1,2,3]triazolo[4,5-b]pyrazine hydrochloride (90 mg, 82%).

$^1$H-NMR (300 MHz, CDCl$_3$) δ 8.91 (s, 1H), 8.26 (s, 2H), 8.14 (s, 1H), 8.08 (s, 1H), 5.89-5.82 (m, 1H), 4.79 (dd, J=6.9 Hz, J=13.8 Hz, 1H), 4.65 (dd, J=6.9 Hz, J=13.8 Hz, 1H), 4.44 (dd, J=3.7 Hz, J=13.3 Hz, 1H), 4.30(dt, J=3.7 Hz, J=13.3 Hz, 1H), 4.08-4.04(m, 2H), 4.03(s, 3H), 3.63 (t, J=4.7 Hz, 2H), 3.40-3.33(m, 1H), 3.25(dd, J=9.0 Hz, J=13.3 Hz, 1H), 2.59-2.51(m, 1H), 2.42-2.35(m, 2H), 1.92-1.82(m, 2H), 1.71-1.43 (m, 2H)

2-(4-(2-(3-((6-(1-methyl-1H-pyrazol-4-yl)-1H-[1,2,3]triazolo[4,5-b]pyrazine-1-yl)methyl)piperidin-1-yl)pyrimidin-5-yl)-5,6-dihydropyridin-1(2H)-yl)ethanol (Chemical Formula 35)

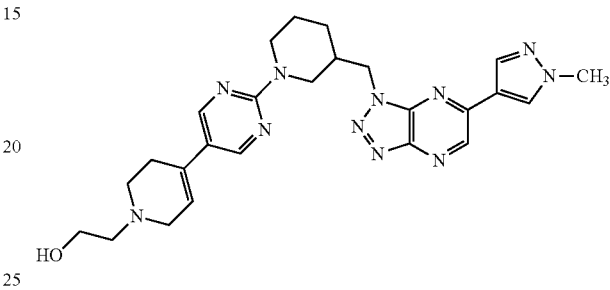

6-(1-methyl-1H-pyrazol-4-yl)-1-((1-(5-(1,2,3,6-tetrahydropyridin-4-yl)pyrimidin-2-yl)piperidin-3-yl)methyl)-1H-[1,2,3]triazolo[4,5-b]pyrazine hydrochloride (71 mg, 0.14 mmol) was dissolved in DMF (2 ml), and then 2-bromoethanol (16 μl, 0.22 mmol), K$_2$CO$_3$ (100 mg, 0.72 mmol), and Et$_3$N (100 ul, 0.72 mmol) were added, followed by stirring at room temperature overnight. After the completion of the reaction, the reaction mixture was extracted with H$_2$O, EA, and brine, followed by drying (Na$_2$SO$_4$), filtration, and concentration under reduced pressure, and the residue was purified by column chromatography (MeOH:MC=1:10), to give 2-(4-(2-(3-((6-(1-methyl-1H-pyrazol-4-yl)-1H-[1,2,3]triazolo[4,5-b]pyrazin-1-yl)methyl)piperidin-1-yl)pyrimidin-5-yl)-5,6-dihydropyridin-1(2H)-yl)ethanol (10 mg, 13%).

$^1$H-NMR (300 MHz, CDCl$_3$) δ 8.92 (s, 1H), 8.27 (s, 2H), 8.14 (s, 1H), 8.06 (s, 1H), 5.92-5.87 (m, 1H), 4.79 (dd, J=6.9 Hz, J=13.8 Hz, 1H), 4.64 (dd, J=6.9 Hz, J=13.8 Hz, 1H), 4.40 (dd, J=3.7 Hz, J=13.3 Hz, 1H), 4.27 (dt, J=3.7 Hz, J=13.3 Hz, 1H), 4.08-4.04 (m, 2H), 4.03 (s, 3H), 3.71 (t, J=5.3 Hz, 2H), 3.43-3.36(m, 1H), 3.27 (dd, J=9.0 Hz, J=13.3 Hz, 1H), 3.22-3.19(m, 2H), 2.77 (t, J=5.3 Hz, 2H), 2.60-2.52 (m, 1H), 2.45-2.40(m, 2H), 1.91-1.82(m, 2H), 1.63-1.44(m, 2H)

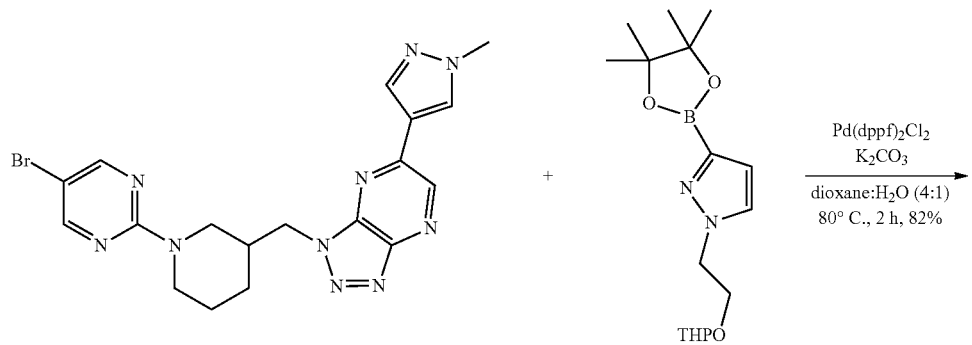

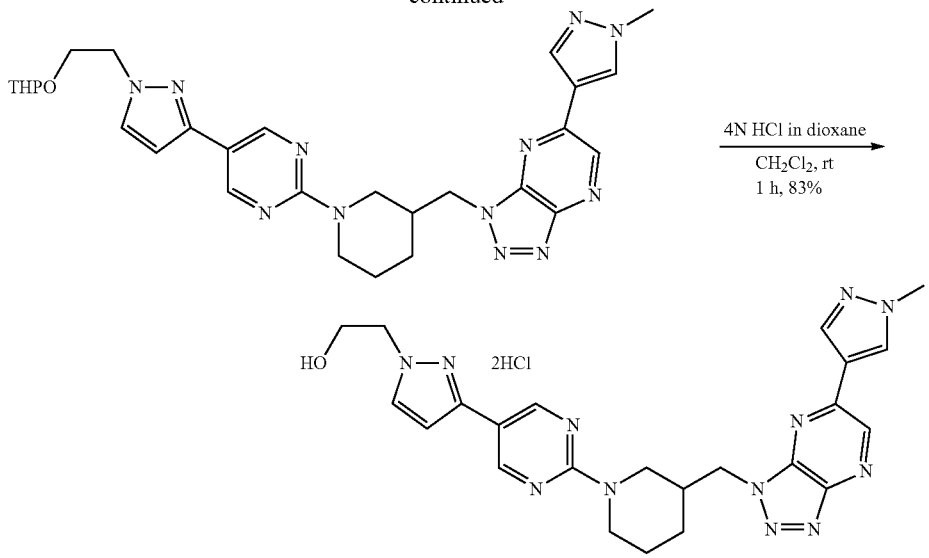

6-(1-methyl-1H-pyrazol-4-yl)-1-((1-(5-(1-(2-((tetrahydro-2H-pyran-2-yl)oxy)ethyl)-1H-pyrazol-3-yl)pyrimidin-2-yl)piperidin-3-yl)methyl)-1H-[1,2,3]triazolo[4,5-b]pyrazine 1-((1-(5-bromopyrimidin-2-yl)piperidin-3-yl)methyl)-6-(1-methyl-1H-pyrazol-4-yl)-1H-[1,2,3]triazolo[4,5-b]pyrazine (30 mg, 0.066 mmol), 1-(2-((tetrahydro-2H-pyran-2-yl)oxy)ethyl)-3-(4,4,5,5-tetramethyl-1,3,2-dioxaborolane-2-yl)-1H-pyrazole (32 mg, 0.099 mmol), Pd(dppf)₂Cl₂(2.7 mg, 0.003 mmol), and K₂CO₃(28 mg, 0.20 mmol) were dissolved in dioxane (1.2 ml)+H₂O (0.3 ml), and the mixture was degassed with N₂(gas), followed by stirring at 80° C. for 2 hours. After the completion of the reaction, the reaction mixture was extracted with H₂O, EA, and brine, followed by drying (Na₂SO₄), filtration, and concentration under reduced pressure, and the residue was purified by column chromatography (MeOH:MC=1:20), to give 6-(1-methyl-1H-pyrazol-4-yl)-1-((1-(5-(1-(2-((tetrahydro-2H-pyran-2-yl)oxy)ethyl)-1H-pyrazol-3-yl)pyrimidin-2-yl)piperidin-3-yl)methyl)-1H-[1,2,3]triazolo[4,5-b]pyrazine (28 mg, 78%).

¹H-NMR (300 MHz, CDCl₃) δ 8.90 (s, 1H), 8.32 (d, J=3.2 Hz, 2H), 8.13 (s, 1H), 8.06 (s, 1H), 7.64-7.61 (m, 2H), 4.64 (dd, J=6.9 Hz, J=13.8 (m, 2H), 4.58-4.55 (m, 1H), 4.43-4.38 (m, 1H), 4.36-4.23(m, 1H), 4.13-4.06 (mm, 2H), 49(d, s, 2H), 486-3.76(m, 1H), 3.69-3.63(m, 1H), 3.49-3.35(m, 2H), 3.30-3.23(m, 1H), 2.61-2.52(m, 1H), 1.92-1.43(m, 10H)

2-(3-(2-(3-((6-(1-methyl-1H-pyrazol-4-yl)-1H-[1,2,3]triazolo[4,5-b]pyrazin-1-yl)methyl)piperidin-1-yl)pyrimidin-5-yl)-1H-pyrazol-1-yl)ethanolhydrochloride (Chemical Formula 36)

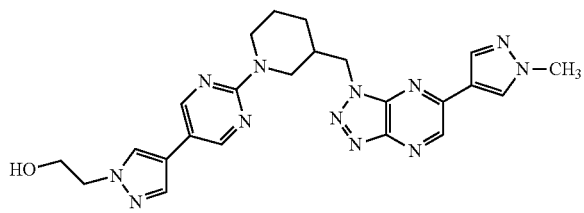 [SMILES: Cn1cc(-c2cnc3nnn(CC4CCCN(c5ncc(-c6cnn(CCO)c6)cn5)C4)c3n2)cn1]

6-(1-methyl-1H-pyrazol-4-yl)-1-((1-(5-(1-(2-((tetrahydro-2H-pyran-2-yl)oxy)ethyl)-1H-pyrazol-3-yl)pyrimidin-2-yl)piperidin-3-yl)methyl)-1H-[1,2,3]triazolo[4,5-b]pyrazine (28 mg, 0.049 mmol) was dissolved in CH₂Cl₂ (5 ml), and then 4 N HCl dioxane (1 ml) was added, followed by stirring at room temperature for 1 hour. After the reaction was completed, the reaction mixture was purified with ether to give 2-(3-(2-(3-((6-(1-methyl-1H-pyrazol-4-yl)-1H-[1,2,3]triazolo[4,5-b]pyrazin-1-yl)methyl)piperidin-1-yl)pyrimidin-5-yl)-1H-pyrazol-1-yl)ethanolhydrochloride (21.5 mg, 83%).

¹H-NMR (300 MHz, CDCl₃) δ 8.90 (s, 1H), 8.32 (d, J=3.2 Hz, 2H), 8.13 (s, 1H), 8.06 (s, 1H), 7.64-7.61 (m, 2H), 4.64 (dd, J=6.9 Hz, J=13.8 Hz, 1H), 4.43-4.38 (m, 1H), 4.30-4.23 (m, 1H), 4.13-4.06 (m, 1H), 3.99 (s, 3H), 3.86-3.76 (m, 1H), 3.69-3.63 (m, 1H), 3.49-3.35 (m, 2H), 3.30-3.23 (m, 1H), 2.61-2.52 (m, 1H), 1.92-1.43 (m, 4H)

tert-butyl 4-(3-(2-(3-((6-(1-methyl-1H-pyrazol-4-yl)-1H-[1,2,3]triazolo[4,5-b]pyrazin-1-yl)methyl)piperidin-1-yl)pyrimidin-5-yl)-1H-pyrazol-1-yl)piperidine-1-carboxylate 1-((1-(5-bromopyrimidin-2-yl)piperidin-3-yl)methyl)-6-(1-methyl-1H-pyrazol-4-yl)-1H-[1,2,3]triazolo[4,5-b]pyrazine (20 mg, 0.0434 mmol), tert-butyl 4-(4-(4,4,5,5-tetramethyl-1,3,2-dioxaborolane-2-yl)-1H-pyrazol-1-yl)piperidine-1-carboxylate (20 mg, 0.053 mmol), Pd(PPh₃)₄ (2.6 mg, 0.0022 mmol), and Na₂CO₃ (17 mg, 0.13 mmol) were dissolved in THF (1 ml)+H₂O (0.6 ml), and then the mixture was degassed with N₂ (gas), followed by stirring at 80° C. for 2 hours. After the completion of the reaction, the reaction mixture was extracted with H₂O, EA, and brine, followed by drying (Na₂SO₄), filtration, and concentration under reduced pressure, and the residue was purified by column chromatography (MeOH:MC=1:20), to give tert-butyl 4-(3-(2-(3-((6-(1-methyl-1H-pyrazol-4-yl)-1H-[1,2,3]triazolo[4,5-b]pyrazin-1-yl)methyl)piperidin-1-yl)pyrimidin-5-yl)-1H-pyrazol-1-yl)piperidine-1-carboxylate (25 mg, 90%).

¹H-NMR (300 MHz, CDCl₃) δ 8.91 (s, 1H), 8.32 (s, 2H), 8.13 (s, 1H), 8.05 (s, 1H), 7.63 (s, 1H), 7.51 (s, 1H), 4.80 (dd, J=6.9 Hz, J=13.8 Hz, 1H), 4.64 (dd, J=6.9 Hz, J=13.8 Hz, 1H), 4.40 (dd, J=3.7 Hz, J=13.3 Hz, 1H), 4.33-4.23 (m, 3H), 3.98 (s, 3H), 3.43-3.36 (m, 1H), 3.27 (dt J=9.0 Hz, J=13.3 Hz, 1H), 2.98-2.84 (m, 1H), 2.61-2.52 (m, 1H), 2.19-2.13 (m, 2H), 2.11-2.07 (m, 1H), 2.01-1.80 (m, 4H), 1.63-1.44 (m, 2H), 1.49 (s, 9H)

61

6-(1-methyl-1H-pyrazol-4-yl)-1-((1-(5-(1-(piperidin-4-yl)-1H-pyrazol-3-yl)pyrimidin-2-yl)piperidin-3-yl)methyl)-1H-[1,2,3]triazolo[4,5-b]pyrazinehydrochloride (Chemical formula 37)

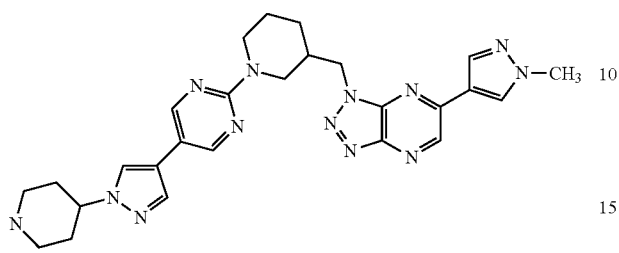

4-(3-(2-(3-((6-(1-methyl-1H-pyrazol-4-yl)-1H-[1,2,3]triazolo[4,5-b]pyrazin-1-yl)methyl)piperidin-1-yl)pyrimidin-5-yl)-1H-pyrazol-1-yl)piperidine-1-carboxylate (25 mg, 0.04 mmol) was dissolved in $CH_2Cl_2$ (5 ml), and then 4 N HCl in dioxane (1 ml) was added, followed by stirring at room temperature for 1 hour. After the reaction was completed, the reaction mixture was concentrated under reduced pressure, and then purified with ether, to give 6-(1-methyl-1H-pyrazol-4-yl)-1-((1-(5-(1-(piperidin-4-yl)-1H-pyrazol-3-yl)pyrimidin-2-yl)piperidin-3-yl)methyl)-1H-[1,2,3]triazolo[4,5-b]pyrazine hydrochloride (18 mg, 75%).

$^1$H-NMR (300 MHz, $CDCl_3$) δ 8.91(s, 1H), 8.32(s, 2H), 8.13(s, 1H), 8.05 (s, 1H), 7.63(s, 1H), 7.51(s, 1H), 4.80 (dd, J=6.9 Hz, J=13.8 Hz, 1H), 4.64 (dd, J=6.9 Hz, J=13.8 Hz, 1H), 4.40 (dd, J=3.7 Hz, J=13.3 Hz, 1H), 4.33-4.23(m, 3H), 3.98 (s, 3H), 3.43-3.36(m, 1H), 3.27 (dt J=9.0 Hz, J=13.3 Hz, 1H), 2.98-2.84(m, 1H), 2.61-2.52(m, 1H), 2.19-2.13 (m, 2H), 2.11-2.07(m, 1H), 2.01-1.80(m, 4H), 1.63-1.44 (m, 2H)

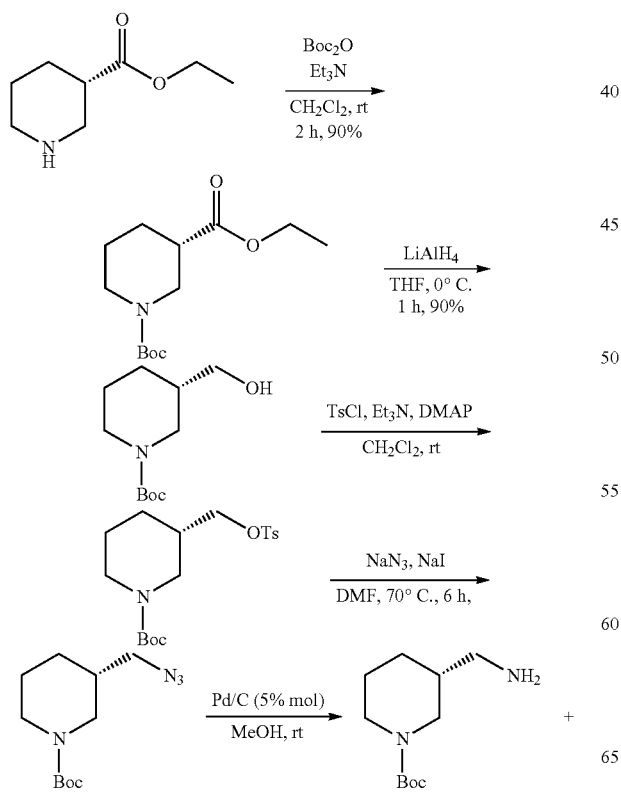

62

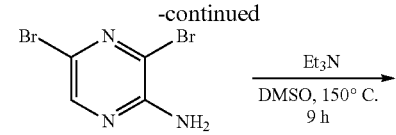

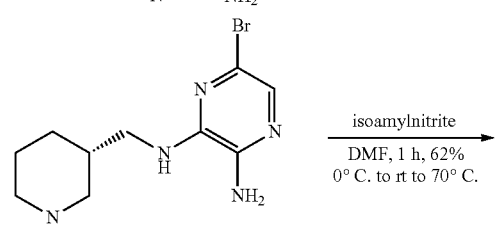

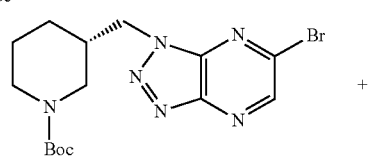

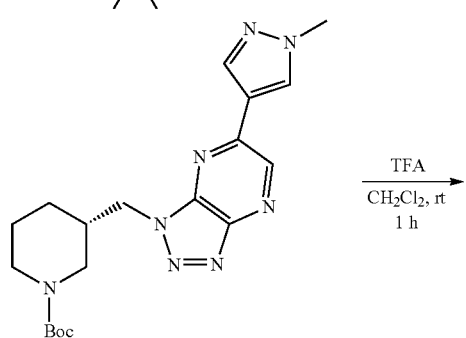

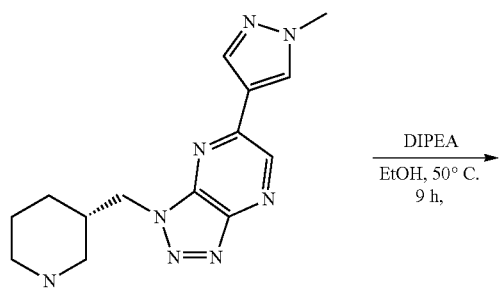

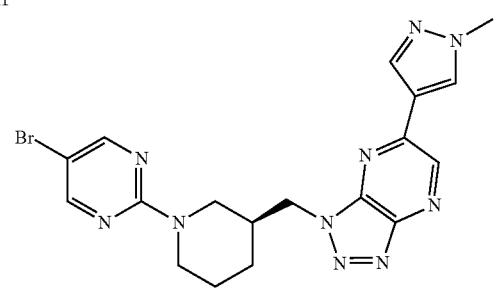

(S)-1-tert-butyl 3-ethyl piperidine-1,3-dicarboxylate (S)-ethyl piperidine-3-carboxylate (3 g, 19.08 mmol) was dissolved in CH$_2$Cl$_2$ (50 ml), and then BOC$_2$O (5 g, 22.90 mmol) and Et$_3$N (4 ml, 28.62 mmol) were added, followed by stirring at room temperature for 3 hours.

After the completion of the reaction, the reaction mixture was extracted with H$_2$O, EA, and brine, followed by drying (Na$_2$SO$_4$), filtration, and concentration under reduced pressure, and the residue was purified by column chromatography (EA:Hex=1:10), to give (S)-1-tert-butyl 3-ethyl piperidine-1,3-dicarboxylate (4.27 g, 87%).

$^1$H-NMR (300 MHz, CDCl$_3$) δ 4.14 (q, J=7.1 Hz, J=14.3 Hz, 2H), 4.30-4.05 (m, 1H), 3.92 (d, J=12.1 Hz, 1H), 3.11-2.87 (m, 1H), 2.85-2.77 (m, 1H), 2.44 (t, J=10.0 Hz, 1H), 2.09-2.00 (m, 1H), 1.75-1.51 (m, 3H), 1.47 (s, 9H), 1.26 (t, J=7.1 Hz, 3H)

(S)-tert-butyl 3-(hydroxymethyl)piperidine-1-carboxylate (S)-1-tert-butyl 3-ethylpiperidine-1,3-dicarboxylate (4.27 g, 16.59 mmol) was dissolved in THF (100 ml), and then LiAlH$_4$ (1.26 g, 33.19 mmol) was added at 0° C. The mixture was stirred for 1 hour, and then again at room temperature for 2 hours. When the reaction was completed, H$_2$O (1.26 ml) was slowly added, and NaOH (15%, 1.26 ml) was slowly added. After that, H$_2$O (4 ml) was added, followed by stirring at room temperature for 1 hour. The mixture was filtered through celite, and dried over MgSO$_4$, followed by filtration and then concentration under reduced pressure, to give (S)-tert-butyl 3-(hydroxymethyl)piperidine-1-carboxylate (3.5 g, 99%).

$^1$H-NMR (300 MHz, CDCl$_3$) δ 3.91-3.51(m, 2H), 3.50(d, J=5.9 Hz, 2H), 3.24-2.75(m, 2H), 2.62-2.08(m, 2H), 1.86-1.18(m, 4H), 1.45(s, 9H)

(S)-tert-butyl 3-((tosyloxy)methyl)piperidine-1-carboxylate (S)-tert-butyl 3-(hydroxymethyl)piperidine-1-carboxylate (3.5 g, 16.59 mmol) was dissolved in CH$_2$Cl$_2$ (60 ml), and then TsCl (3.8 g, 19.91 mmol), Et$_3$N (3.47 ml, 24.87 mmol), and DMAP (0.21 g, 1.66 mmol) were added, followed by stirring at room temperature for 3 hours. After the completion of the reaction, the reaction mixture was extracted with H$_2$O, MC, and brine, followed by drying (Na$_2$SO$_4$), filtration, and concentration under reduced pressure, and the residue was purified by column chromatography (EA:Hex=1:5), to give (S)-tert-butyl 3-((tosyloxy)methyl)piperidine-1-carboxylate (6 g, 97%).

$^1$H-NMR (300 MHz, CDCl$_3$) δ 7.78(d, J=8.0 Hz, 2H), 7.35(d, J=8.0 Hz, 2H), 3.88(d, J=6.4 Hz, 2H), 3.85-3.75(m, 2H), 2.81(t, J=11.0 Hz, 1H), 2.74-2.50(m, 1H), 2.45(s, 3H), 1.91-1.15(m, 5H), 1.43 (s, 9H)

(S)-tert-butyl 3-(azidomethyl)piperidine-1-carboxylate (S)-tert-butyl 3-((tosyloxy)methyl)piperidine-1-carboxylate (8.85 g, 24 mmol) was dissolved in DMF (100 ml), and then NaN$_3$ (6.24 g, 96 mmol) and NaI (0.36 g, 2.40 mmol) were added, followed by stirring at 70° C. for 4 hours. After the completion of the reaction, the reaction mixture was extracted with H$_2$O, EA, and brine, followed by drying (Na$_2$SO$_4$), filtration, and concentration under reduced pressure, and the residue was purified by column chromatography (EA:Hex=1:10), to give (S)-tert-butyl 3-(azidomethyl)piperidine-1-carboxylate (5.38 g, 92%).

$^1$H-NMR (300 MHz, CDCl$_3$) δ 4.09-3.82 (m, 2H), 3.27-3.16 (m, 2H), 2.95-2.54 (m, 2H), 1.88-1.62 (m, 3H), 1.52-1.42 (m, 1H), 1.47 (s, 9H), 1.30-1.20 (m, 1H)

(R)-tert-butyl 3-(aminomethyl)piperidine-1-carboxylate (S)-tert-butyl 3-(azidomethyl)piperidine-1-carboxylate (5.38 g, 22.40 mmol) was dissolved in MeOH (50 ml), and then Pd/C (5% mol) was added, followed by stirring at room temperature under H$_2$ (gas) for 9 hours. After the completion of the reaction, the reaction mixture was filtered through celite, followed by filtration and concentration under reduced pressure, and then the next reaction was advanced without purification.

$^1$H-NMR (300 MHz, CDCl$_3$) δ 4.02-3.73 (m, 2H), 2.94-2.73 (m, 1H), 2.72-2.33 (m, 3H), 1.90-1.02 (m, 5H), 1.44 (s, 9H)

(R)-tert-butyl 3-(((3-amino-6-bromopyrazine-2-yl)amino)methyl)piperidine-1-carboxylate (R)-tert-butyl 3-(aminomethyl)piperidine-1-carboxylate (4.97 g, 22.40 mmol) was dissolved in DMSO (80 ml), and then 3,5-dibromopyrazine-2-amine (8.5 g, 33.60 mmol) and Et$_3$N (6.3 ml) were added, followed by stirring at 130° C. overnight. After the completion of the reaction, the reaction mixture was extracted with H$_2$O, EA, and brine, followed by drying (Na$_2$SO$_4$), filtration, and concentration under reduced pressure, and the residue was purified by column chromatography (EA:Hex=1:1), to give (R)-tert-butyl 3-(((3-amino-6-bromopyrazine-2-yl)amino)methyl)piperidine-1-carboxylate (2.19 g, two steps: 26%).

$^1$H-NMR (300 MHz, CDCl$_3$) δ 7.39 (s, 1H), 4.64-4.23 (m, 2H), 3.79-2.92 (m, 5H), 2.25-1.19 (m, 4H), 1.46 (s, 9H)

(S)-tert-butyl 3-((6-bromo-1H-[1,2,3]triazolo[4,5-b]pyrazin-1-yl)methyl) piperidine-1-carboxylate (R)-tert-butyl 3-(((3-amino-6-bromopyrazine-2-yl)amino)methyl)piperidine-1-carboxylate (2.19 g, 5.70 mmol) was dissolved in DMF (15 ml), and then isoamylnitrile (0.92 ml, 6.84 mmol) was slowly dropped at 0° C. After that, the mixture was stirred at 70° C. for 1 hour. After the completion of the reaction, the reaction mixture was extracted with H$_2$O, EA, and brine, followed by drying (Na$_2$SO$_4$), filtration, and concentration under reduced pressure, and the residue was purified by column chromatography (EA:Hex=1:8), to give (S)-tert-butyl 3-((6-bromo-1H-[1,2,3]triazolo[4,5-b]pyrazin-1-yl)methyl)piperidine-1-carboxylate (1.39 g, 62%).

$^1$H-NMR (300 MHz, CDCl$_3$) δ 8.78 (s, 1H), 4.63 (q, J=7.3 Hz, J=14.1 Hz, 2H), 3.96-3.67 (m, 2H), 3.05-2.74 (m, 2H), 2.47-2.31 (m, 1H), 1.81-1.67 (m, 2H), 1.56-1.14 (m, 2H), 1.40 (s, 9H)

(S)-tert-butyl 3-((6-(1-methyl-1H-pyrazol-4-yl)-1H-[1,2,3]triazolo[4,5-b]pyrazin-1-yl)methyl)piperidine-1-carboxylate (S)-tert-butyl 3-((6-bromo-1H-[1,2,3]triazolo[4,5-b]pyrazin-1-yl)methyl)piperidine-1-carboxylate (0.5 g, 1.26 mmol), 1-methyl-4-(4,4,5,5-tetramethyl-1,3,2-dioxaborolane-2-yl)-1H-pyrazole (0.32 g, 1.51 mmol), Pd(dppf)$_2$Cl$_2$ (82 mg, 0.06 mmol), and Cs$_2$CO$_3$ (1.24 g, 3.78 mmol) were dissolved in DME (3 ml)+H$_2$O (1 ml), and then degassed with N$_2$ (gas), followed by stirring at 80° C. After the completion of the reaction, the reaction mixture was extracted with H$_2$O, EA, and brine, followed by drying (Na$_2$SO$_4$), filtration, and concentration under reduced pressure, and the residue was purified by column chromatography (EA:Hex=1:1), to give, (S)-tert-butyl 3-((6-(1-methyl-1H-pyrazol-4-yl)-1H-[1,2,3]triazolo[4,5-b]pyrazin-1-yl)methyl)piperidine-1-carboxylate (0.45 g, 89%).

$^1$H-NMR (300 MHz, CDCl$_3$) δ 8.87 (s, 1H), 8.17-8.07 (m, 2H), 4.59 (q, J=7.3 Hz, J=14.1 Hz, 2H), 4.00 (s, 3H), 3.96-3.68 (m, 2H), 3.06-2.69 (m, 2H), 2.45-2.27 (m, 1H), 1.82-1.62 (m, 2H), 1.53-1.17 (m, 2H), 1.36 (s, 9H)

(S)-6-(1-methyl-1H-pyrazol-4-yl)-1-(piperidin-3-yl)methyl)-1H-[1,2,3]triazolo[4,5-b]pyrazine (S)-tert-butyl 3-((6-(1-methyl-1H-pyrazol-4-yl)-1H-[1,2,3]triazolo[4,5-b]pyrazin-1-yl)methyl)piperidine-1-carboxylate (0.45 g, 0.89 mmol) was dissolved in CH$_2$Cl$_2$ (5 ml), and then TFA (5 ml) was added, followed by stirring at room temperature overnight. After the completion of the reaction, the reaction mixture was concentrated under reduced pressure, and the next reaction was advanced without purification.

(S)-1-((1-(5-bromopyrimidin-2-yl)piperidin-3-yl)methyl)-6-(1-methyl-1H-pyrazol-4-yl)-1H-[1,2,3]triazolo[4,5-b]pyrazine (S)-6-(1-methyl-1H-pyrazol-4-yl)-1-(piperidin-3-yl)methyl)-1H-[1,2,3]triazolo[4,5-b]pyrazine (0.26 g, 0.89 mmol) was dissolved in EtOH (15 ml), and 5-bromo-2-chloropyrimidine (0.33 g, 1.33 mmol) and DIPEA (0.77 ml, 4.43 mmol) were added, followed by stirring at 50° C. overnight. After the completion of the reaction, the reaction mixture was extracted with H$_2$O, EA, and brine, followed by drying (Na$_2$SO$_4$), filtration, and concentration under reduced pressure, and the residue was purified by column chromatography (EA:Hex=1:1), to give (S)-1-((1-(5-bromo pyrimidin-2-yl)piperidin-3-yl)methyl)-6-(1-methyl-1H-pyrazol-4-yl)-1H-[1,2,3]triazolo[4,5-b]pyrazine (0.28 g, 70%).

$^1$H-NMR (300 MHz, CDCl$_3$) δ 8.92 (s, 1H), 8.19 (s, 2H), 8.15 (s, 1H), 8.08 (s, 1H), 4.78 (dd, J=6.9 Hz, J=13.8 Hz, 1H), 4.64 (dd, J=6.9 Hz, J=13.8 Hz, 1H), 4.34 (dd, J=3.7 Hz, J=13.3 Hz, 1H), 4.22 (dt, J=3.7 Hz, J=13.3 Hz, 1H), 4.05 (s, 3H), 3.40-3.32 (m, 1H), 3.23 (dd, J=9.0 Hz, J=13.3 Hz, 1H), 2.59-2.50 (m, 1H), 1.91-1.82 (m, 2H), 1.62-1.44 (m, 2H)

(S)-2-((6-(1-methyl-1H-pyrazol-4-yl)-1H-[1,2,3]triazolo[4,5-b]pyrazin-1-yl)methyl)-4-(5-(4-((4-methylpiperazin-1-yl)methyl)phenyl)pyrimidin-2-yl)morpholine (Chemical Formula 17)

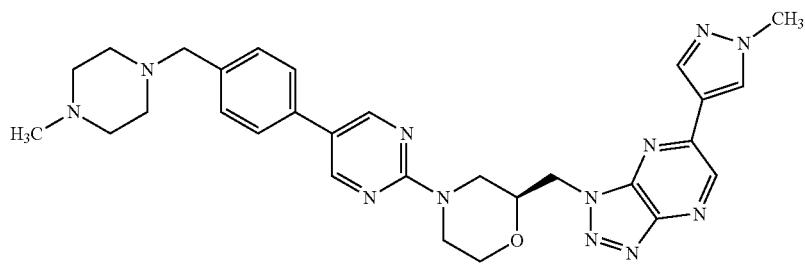

(S)-1-((1-(5-bromopyrimidin-2-yl)piperidin-3-yl)methyl)-6-(1-methyl-1H-pyrazol-4-yl)-1H-[1,2,3]triazolo[4,5-b]pyrazine (250 mg, 0.55 mmol), 1-methyl-4-(4-(4,4,5,5-tetramethyl-1,3,2-dioxaborolane-2-yl)benzyl)piperazine (210 mg, 0.66 mmol), Pd(dppf)$_2$Cl$_2$ (23 mg, 0.027 mmol), and K$_2$CO$_3$ (228 mg, 1.65 mmol) were dissolved in dioxane (6 ml)+H$_2$O (1.5 ml), and then degassed with N$_2$ (gas), followed by stirring at 80° C. for hours. After the completion of the reaction, the reaction mixture was extracted with H$_2$O, EA, and brine, followed by drying (Na$_2$SO$_4$), filtration, and concentration under reduced pressure, and the residue was purified by column chromatography (MeOH:MC=1:10), to give (S)-2-((6-(1-methyl-1H-pyrazol-4-yl)-1H-[1,2,3]triazolo[4,5-b]pyrazin-1-yl)methyl)-4-(5-(4-((4-methylpiperazin-1-yl)methyl)phenyl)pyrimidin-2-yl)morpholine (210 mg, 71%).

(S)-1-(4-(4-(2-(2-((6-(1-methyl-1H-pyrazol-4-yl)-1H-[1,2,3]triazolo[4,5-b]pyrazin-1-yl)methyl)morpholino)pyrimidin-5-yl)benzyl)piperazin-1-yl)ethanone (Chemical Formula 45)

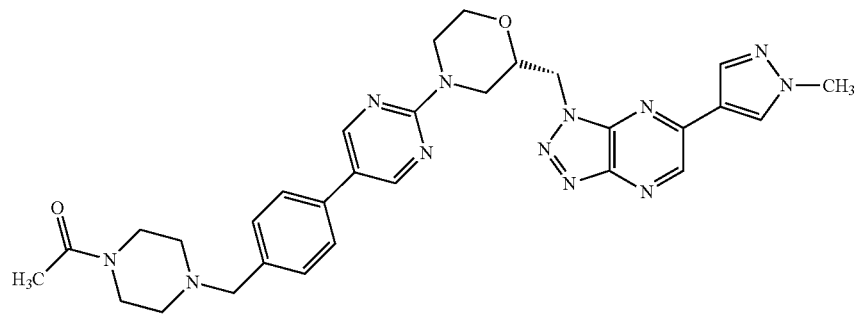

(S)-4-(5-bromopyrimidin-2-yl)-2-((6-(1-methyl-1H-pyrazol-4-yl)-1H-[1,2,3]triazolo[4,5-b]pyrazin-1-yl)methyl)morpholine (50 mg, 0.11 mmol), 1-(4-(4-(4,4,5,5-tetramethyl-1,3,2-dioxaborolane-2-yl)benzyl)piperazin-1-yl)ethanone (45 mg, 0.13 mmol), Pd(dppf)$_2$Cl$_2$ (4.5 mg, 0.005 mmol), and K$_2$CO$_3$ (45 mg, 0.33 mmol) were dissolved in dioxane (4 ml)+H$_2$O (1 ml), and then degassed with N$_2$ (gas), followed by stirring at 80° C. for 2 hours. After the completion of the reaction, the reaction mixture was extracted with H$_2$O, EA, and brine, followed by drying (Na$_2$SO$_4$), filtration, and concentration under reduced pressure, and the residue was purified by column chromatography (MeOH:MC=1:10), to give (S)-1-(4-(4-(2-(2-((6-(1-methyl-1H-pyrazol-4-yl)-1H-[1,2,3]triazolo[4,5-b]pyrazine-1-yl)methyl)morpholino)pyrimidin-5-yl)benzyl)piperazin-1-yl)ethanone (58 mg, 90%).

$^1$H-NMR (300 MHz, CDCl$_3$) δ 8.92 (s, 1H), 8.55 (s, 2H), 8.17 (s, 1H), 8.13 (s, 1H), 7.55-7.28 (m, 2H), 4.96 (dd, J=7.7 Hz, J=14.2 Hz, 1H), 4.86-4.71 (m, 2H), 4.48 (d, J=13.2 Hz, 1H), 4.34-4.23 (m, 1H), 4.02 (s, 3H), 4.02-3.97(m, 1H), 3.68-3.59(m, 3H), 3.56(s, 2H), 3.47 (t, J=4.3 Hz, 2H), 3.29-3.08 (m, 2H), 2.51-2.40(m, 4H), 2.11(s, 3H)

(S)-1-(4-(4-(2-(2-((6-(1-methyl-1H-pyrazol-4-yl)-1H-[1,2,3]triazolo[4,5-b]pyrazin-1-yl)methyl)morpholino)pyrimidin-5-yl)benzyl)piperazin-1-yl)ethanone hydrochloride (S)-1-(4-(4-(2-(2-((6-(1-methyl-1H-pyrazol-4-yl)-1H-[1,2,3]triazolo[4,5-b]pyrazin-1-yl)methyl)morpholino)pyrimidin-5-yl)benzyl)piperazin-1-yl)ethanone (58 mg, 0.084 mmol) was dissolved in CH$_2$Cl$_2$ (5 ml), and then 4 N HCl in dioxane (1 ml) was added, followed by stirring at room temperature for 1 hour. After the reaction was completed, the reaction mixture was purified with ether to give (S)-1-(4-(4-(2-(2-((6-(1-methyl-1H-pyrazol-4-yl)-1H-[1,2,3]triazolo[4,5-b]pyrazin-1-yl)methyl)morpholino)pyrimidin-5-yl)benzyl)piperazin-1-yl)ethanone hydrochloride (47 mg, 90%).

(S)-1-(4-(4-(2-(3-((6-(1-methyl-1H-pyrazol-4-yl)-1H-[1,2,3]triazolo[4,5-b]pyrazin-1-yl)methyl)piperidin-1-yl)pyrimidin-5-yl)benzyl)piperazin-1-yl)ethanone (Chemical Formula 46)

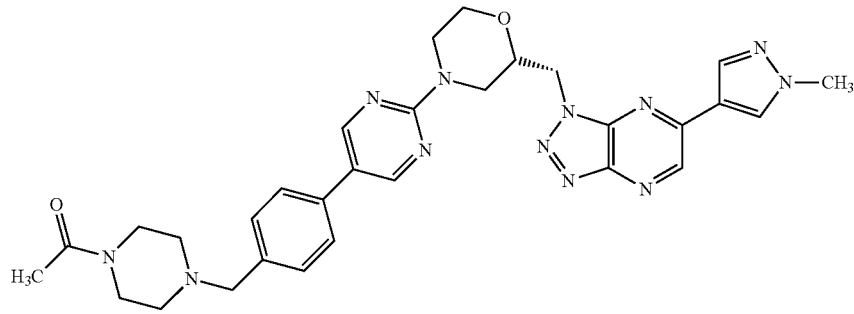

(S)-1-((1-(5-bromopyrimidin-2-yl)piperidin-3-yl)methyl)-6-(1-methyl-1H-pyrazol-4-yl)-1H-[1,2,3]triazolo[4,5-b]pyrazine (50 mg, 0.11 mmol), 1-(4-(4-(4,4,5,5-tetramethyl-1,3,2-dioxaborolane-2-yl)benzyl)piperazin-1-yl)ethanone (45 mg, 0.13 mmol), Pd(dppf)$_2$Cl$_2$ (4.5 mg, 0.0054 mmol), and K$_2$CO$_3$ (45 mg, 0.33 mmol) were dissolved in dioxane (4 ml)+H$_2$O (1 ml), and then degassed with N$_2$(gas), followed by stirring at 80° C. for 2 hours. After the completion of the reaction, the reaction mixture was extracted with H$_2$O, EA, and brine, followed by drying (Na$_2$SO$_4$), filtration, and concentration under reduced pressure, and the residue was purified by column chromatography (MeOH:MC=1:10), to give (S)-1-(4-(4-(2-(3-((6-(1-methyl-1H-pyrazol-4-yl)-1H-[1,2,3]triazolo[4,5-b]pyrazin-1-yl)methyl)piperidin-1-yl)pyrimidin-5-yl)benzyl)piperazin-1-yl)ethanone (48 mg, 74%).

$^1$H-NMR (300 MHz, CDCl$_3$) δ 8.90 (s, 1H), 8.45 (s, 2H), 8.13 (s, 1H), 8.05(s, 1H), 7.27(s, 1H), 4.80(dd, J=7.0 Hz, J=14.1 Hz, 1H), 4.46(dd, J=3.3 Hz, J=13.1 Hz, 1H), 4.38-4.27(m, 1H), 3.97(s, 3H), 3.63(t, J=4.3 Hz, 2H), 3.55 (s, 2H), 3.47(t, J=4.3 Hz, 2H), 3.44-3.33(m, 1H), 3.27 (dd, J=8.7 Hz, 13.4 Hz, 1H), 2.63-2.50 (m, 1H), 2.50-2.39 (m, 4H), 2.08(s, 3H), 1.94-1.80(m, 2H), 1.66-1.44(m, 2H)

(S)-1-(4-(4-(2-(3-((6-(1-methyl-1H-pyrazol-4-yl)-1H-[1,2,3]triazolo[4,5-b]pyrazin-1-yl)methyl)piperidin-1-yl)pyrimidin-5-yl)benzyl)piperazin-1-yl)ethanone hydrochloride

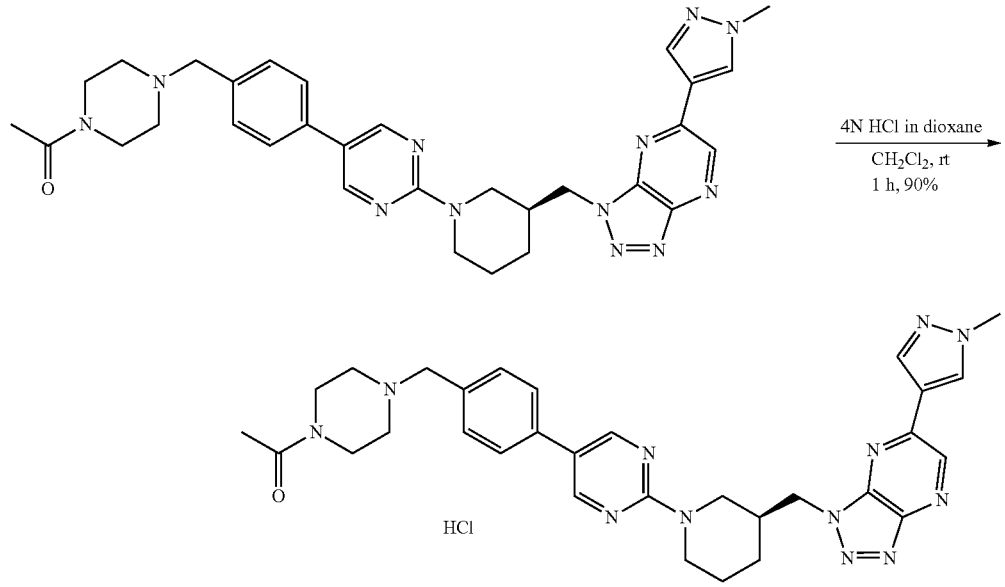

(S)-1-(4-(4-(2-(3-((6-(1-methyl-1H-pyrazol-4-yl)-1H-[1,2,3]triazolo[4,5-b]pyrazin-1-yl)methyl)piperidin-1-yl)pyrimidin-5-yl)benzyl)piperazin-1-yl)ethanone (48 mg, 0.08 mmol) was dissolved in $CH_2Cl_2$(5 ml), and 4 N HCl in dioxane (1 ml) was added, followed by stirring at room temperature for 1 hour. After the reaction was completed, the reaction mixture was purified with ether to give (S)-1-(4-(4-(2-(3-((6-(1-methyl-1H-pyrazol-4-yl)-1H-[1,2,3]triazolo[4,5-b]pyrazin-1-yl)methyl)piperidin-1-yl)pyrimidin-5-yl)benzyl)piperazin-1-yl)ethanone hydrochloride (46 mg, 90%).

(S)-(4-(2-(2-((6-(1-methyl-1H-pyrazol-4-yl)-1H-[1,2,3]triazolo[4,5-b]pyrazin-1-yl)methyl)morpholino)pyrimidin-5-yl)phenyl)(4-methylpiperazin-1-yl)methanone (Chemical Formula 47)

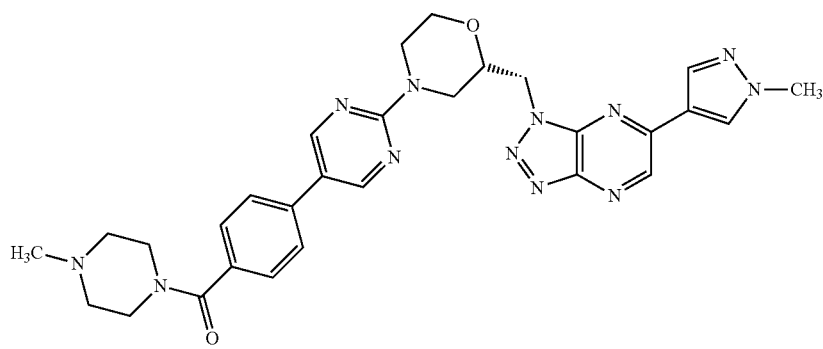

(S)-4-(5-bromopyrimidin-2-yl)-2-((6-(1-methyl-1H-pyrazol-4-yl)-1H-[1,2,3]triazolo[4,5-b]pyrazin-1-yl)methyl)morpholine (50 mg, 0.11 mmol), (4-methylpiperazin-1-yl)(4-(4,4,5,5-tetramethyl-1,3,2-dioxaborolane-2-yl)phenyl)methanone (45 mg, 0.13 mmol), Pd(dppf)$_2$Cl$_2$ (4.5 mg, 0.0054 mmol), and K$_2$CO$_3$ (45 mg, 0.33 mmol) were dissolved in dioxane (4 ml)+H$_2$O (1 ml), and then degassed with N$_2$(gas), followed by stirring at 80° C. for 2 hours. After the completion of the reaction, the reaction mixture was extracted with H$_2$O, EA, and brine, followed by drying (Na$_2$SO$_4$), filtration, and concentration under reduced pressure, and the residue was purified by column chromatography (MeOH: MC=1:10), to give (S)-(4-(2-(2-((6-(1-methyl-1H-pyrazol-4-yl)-1H-[1,2,3]triazolo[4,5-b]pyrazin-1-yl)methyl)morpholino)pyrimidin-5-yl)phenyl) (4-methylpiperazin-1-yl)methanone (62 mg, 98%).

$^1$H-NMR (300 MHz, CDCl$_3$) δ 8.92 (s, 1H), 8.56(s, 2H), 8.17 (s, 1H), 8.13 (s, 1H), 7.55-7.45 (m, 4H), 4.97 (dd, J=7.7 Hz, J=14.2 Hz, 1H), 4.87-4.73(m, 2H), 4.50(d, J=13.1 Hz, 1H), 4.34-4.23(m, 1H), 4.02(s, 3H), 4.02-3.97(m, 1H), 3.90-3.69 (m, 2H), 3.61 (dt, J=2.4 Hz, J=11.2 Hz, 1H), 3.30-3.09 (m, 2H), 2.58-2.36 (m, 4H), 2.34(s, 3H)

(S)-(4-(2-(2-((6-(1-methyl-1H-pyrazol-4-yl)-1H-[1,2,3]triazolo[4,5-b]pyrazin-1-yl)methyl)morpholino)pyrimidin-5-yl)phenyl)(4-methylpiperazin-1-yl)methanone hydrochloride

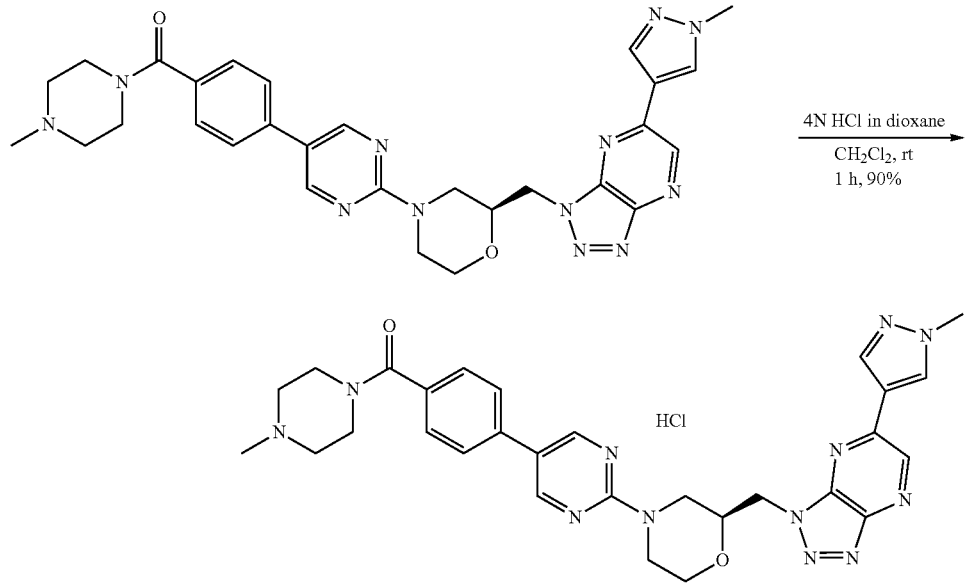

(S)-(4-(2-(2-((6-(1-methyl-1H-pyrazol-4-yl)-1H-[1,2,3]triazolo[4,5-b]pyrazin-1-yl)methyl)morpholino)pyrimidin-5-yl)phenyl) (4-methylpiperazin-1-yl)methanone (62 mg, 0.11 mmol) was dissolved in $CH_2Cl_2$ (5 ml), and 4 N HCl in dioxane (1 ml) was added, followed by stirring at room temperature for 1 hour. After the reaction was completed, the reaction mixture was purified with ether to give (S)-(4-(2-(2-((6-(1-methyl-1H-pyrazol-4-yl)-1H-[1,2,3]triazolo[4,5-b]pyrazin-1-yl)methyl)morpholino)pyrimidin-5-yl)phenyl)(4-methylpiperazin-1-yl)methanone hydrochloride (59 mg, 90%).

(S)-(4-(2-(3-((6-(1-methyl-1H-pyrazol-4-yl)-1H-[1,2,3]triazolo[4,5-b]pyrazin-1-yl)methyl)piperidin-1-yl)pyrimidin-5-yl)phenyl)(4-methylpiperazin-1-yl)methanone (Chemical Formula 48)

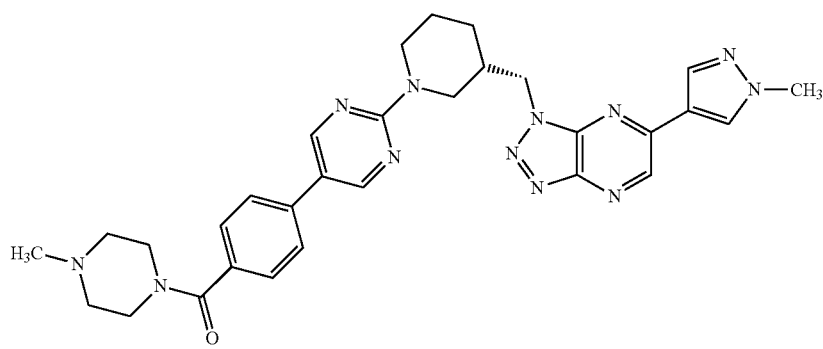

(S)-1-((1-(5-bromopyrimidin-2-yl)piperidin-3-yl)methyl)-6-(1-methyl-1H-pyrazol-4-yl)-1H-[1,2,3]triazolo[4,5-b]pyrazine (50 mg, 0.11 mmol), (4-methylpiperazin-1-yl)(4-(4,4,5,5-tetramethyl-1,3,2-dioxaborolane-2-yl)phenyl)methanone (45 mg, 0.13 mmol), $Pd(dppf)_2Cl_2$ (4.5 mg, 0.0054 mmol), and $K_2CO_3$ (45 mg, 0.33 mmol) were dissolved in dioxane (4 ml)+$H_2O$ (1 ml), and then degassed with $N_2$(gas), followed by stirring at 80□ for 2 hours. After the completion of the reaction, the reaction mixture was extracted with $H_2O$, EA, and brine, followed by drying ($Na_2SO_4$), filtration, and concentration under reduced pressure, and the residue was purified by column chromatography (MeOH:MC=1:10), to give (S)-1-(4-(4-(2-(3-((6-(1-methyl-1H-pyrazol-4-yl)-1H-[1,2,3]triazolo[4,5-b]pyrazine-1-yl)methyl)piperidin-1-yl)pyrimidin-5-yl)benzyl)piperazin-1-yl)ethanone (48 mg, 74%).

$^1$H-NMR (300 MHz, $CDCl_3$) δ 8.89 (s, 1H), 8.45 (s, 2H), 8.12 (s, 1H), 8.04 (s, 1H), 7.50-7.40 (m, 4H), 4.80 (dd, J=7.7 Hz, J=14.2 Hz, 1H), 4.64 (dd, J=7.7 Hz, J=14.2 Hz, 1H), 4.48 (dd, J=2.4 Hz, J=13.2 Hz, 2H), 4.37-4.26 (m, 1H), 3.97 (s, 3H), 3.90-3.70 (m, 2H), 3.61-3.37 (m, 3H), 3.30 (dd, J=9.2 Hz, J=13.1 Hz, 1H), 2.65-2.37 (m, 5H), 2.34 (s, 3H), 1.95-1.78 (m, 2H), 1.67-1.40 (m, 2H)

(S)-(4-(2-(3-((6-(1-methyl-1H-pyrazol-4-yl)-1H-[1,2,3]triazolo[4,5-b]pyrazin-1-yl)methyl)piperidin-1-yl)pyrimidin-5-yl)phenyl)(4-methylpiperazin-1-yl)methanone hydrochloride

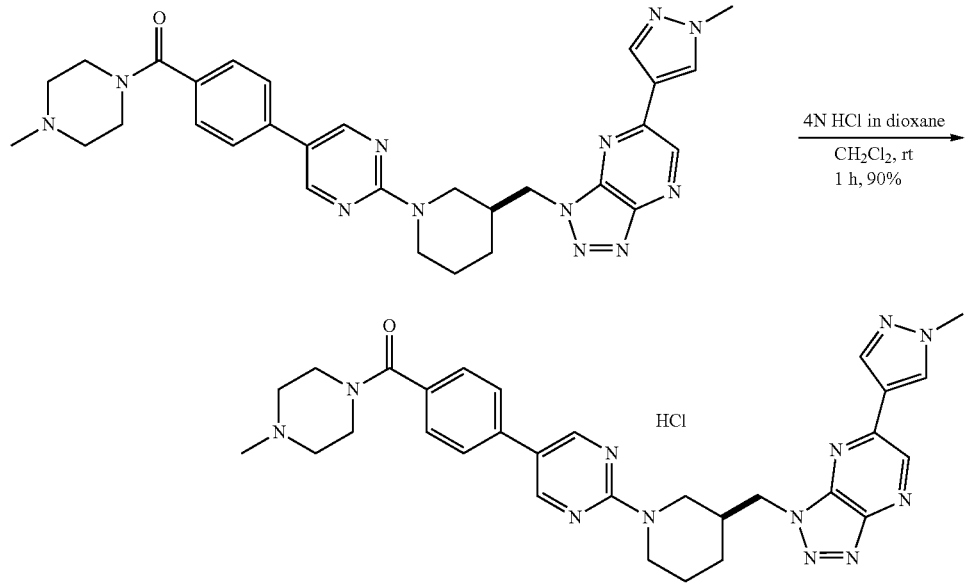

(S)-(4-(2-(3-((6-(1-methyl-1H-pyrazol-4-yl)-1H-[1,2,3]triazolo[4,5-b]pyrazin-1-yl)methyl)piperidin-1-yl)pyrimidin-5-yl)phenyl)(4-methylpiperazin-1-yl)methanone (48 mg, 0.083 mmol) was dissolved in CH$_2$Cl$_2$ (5 ml), and 4 N HCl in dioxane (1 ml) was added, followed by stirring at room temperature for 1 hour. After the reaction was completed, the reaction mixture was purified with ether to give (S)-(4-(2-(3-((6-(1-methyl-1H-pyrazol-4-yl)-1H-[1,2,3]triazolo[4,5-b]pyrazin-1-yl)methyl)piperidin-1-yl)pyrimidin-5-yl)phenyl)(4-methylpiperazin-1-yl)methanone hydrochloride (46 mg, 90%).

(S)-3-(1-((4-(5-(4-((4-methylpiperazin-1-yl)methyl)phenyl)pyrimidin-2-yl)morpholin-2-yl)methyl)-1H-[1,2,3]triazolo[4,5-b]pyrazin-6-yl)benzonitrile
(Chemical Formula 49)

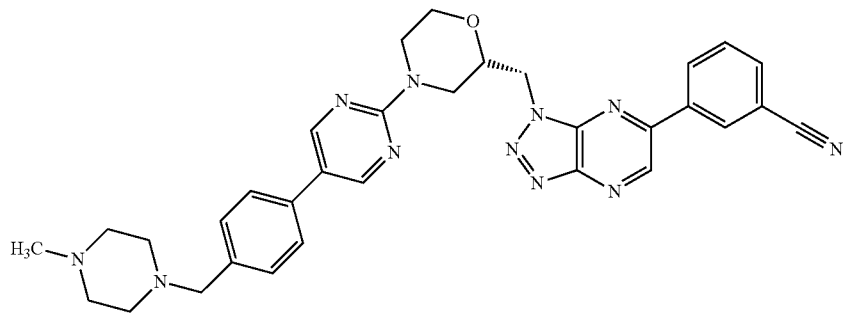

(S)-3-(1-((4-(5-bromopyrimidin-2-yl)morpholine-2-yl)methyl)-1H-[1,2,3]triazolo[4,5-b]pyrazin-6-yl)benzonitrile (30 mg, 0.063 mmol), 1-methyl-4-(4-(4,4,5,5-tetramethyl-1,3,2-dioxaborolane-2-yl)benzyl)piperazine (24 mg, 0.094 mmol), Pd(dppf)$_2$Cl$_2$ (2 mg, 0.003 mmol), and Cs$_2$CO$_3$ (62 mg, 0.18 mmol) were dissolved in dioxane (4 ml)+H$_2$O (1 ml), and then degassed with N$_2$ (gas), followed by stirring at 80° C. for hours. After the completion of the reaction, the reaction mixture was extracted with H$_2$O, EA, and brine, followed by drying (Na$_2$SO$_4$), filtration, and concentration under reduced pressure, and the residue was purified by column chromatography (MeOH:MC=1:10), to give (S)-3-(1-((4-(5-(4-((4-methylpiperazin-1-yl)methyl)phenyl)pyrimidin-2-yl)morpholine-2-yl)methyl)-1H-[1,2,3]triazolo[4,5-b]pyrazin-6-yl)benzonitrile (12.1 mg, 33%).

$^1$H-NMR (300 MHz, CDCl$_3$) δ 9.25 (s, 1H), 8.58 (s, 2H), 8.54 (s, 1H), 8.40 (d, J=7.2 Hz, 1H), 7.86 (d, J=7.2 Hz, 1H), 7.73 (t, J=7.9 Hz, 1H), 7.48-7.39 (m, 4H), 5.08 (dd, J=7.9 Hz, J=14.1 Hz, 1H), 4.95 (dd, J=4.3 Hz, J=14.1 Hz, 1H), 4.87-4.80 (m, 1H), 4.54-4.48 (m, 1H), 4.37-4.29 (m, 1H), 4.05-3.98 (m, 1H), 3.63 (dt, J=2.5 Hz, J=11.4 Hz, 1H), 3.28-3.21 (m, 1H), 3.18 (dt, J=10.8 Hz, J=14.4 Hz, 1H), 2.62-2.35 (m, 8H), 2.31 (s, 3H)

(S)-3-(1-((4-(5-(4-((4-acetylpiperazin-1-yl)methyl)phenyl)pyrimidin-2-yl)morpholin-2-yl)methyl)-1H-[1,2,3]triazolo[4,5-b]pyrazin-6-yl)benzonitrile
(Chemical Formula 50)

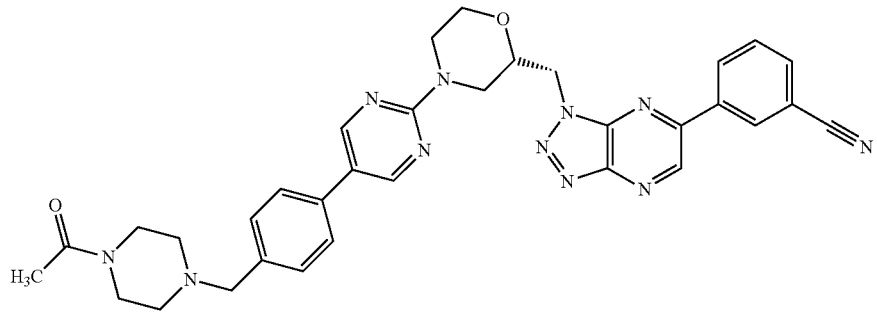

(S)-3-(1-((4-(5-bromopyrimidin-2-yl)morpholine-2-yl)methyl)-1H-[1,2,3]triazolo[4,5-b]pyrazin-6-yl)benzonitrile (30 mg, 0.063 mmol), 1-methyl-4-(4-(4,4,5,5-tetramethyl-1,3,2-dioxaborolane-2-yl)benzyl)piperazine (24 mg, 0.094 mmol), Pd(dppf)$_2$Cl$_2$(2 mg, 0.003 mmol), and Cs$_2$CO$_3$(62 mg, 0.18 mmol) were dissolved in dioxane (4 ml)+H$_2$O (1 ml), and then degassed with N$_2$ (gas), followed by stirring at 80° C. for 2 hours. After the completion of the reaction, the reaction mixture was extracted with H$_2$O, EA, and brine, followed by drying (Na$_2$SO$_4$), filtration, and concentration under reduced pressure, and the residue was purified by column chromatography (MeOH:MC=1:10), to give (S)-3-(1-((4-(5-(4-((4-methylpiperazin-1-yl)methyl)phenyl)pyrimidin-2-yl)morpholine-2-yl)methyl)-1H-[1,2,3]triazolo[4,5-b]pyrazin-6-yl)benzonitrile (15.1 mg, 41%).

$^1$H-NMR (300 MHz, CDCl$_3$) δ 9.25(s, 1H), 8.58(s, 2H), 8.54(s, 1H), 8.40(d, J=7.2 Hz, 1H), 7.86(d, J=7.2 Hz, 1H), 7.73(t, J=7.9 Hz, 1H), 7.48-7.39(m, 4H), 5.08 (dd, J=7.9 Hz, J=14.1 Hz, 1H), 4.95 (dd, J=4.3 Hz, J=14.1 Hz, 1H), 4.87-4.80(m, 1H), 4.54-4.48(m, 1H), 4.37-4.29(m, 1H), 4.05-3.98 (m, 1H), 3.69-3.59(m, 3H), 3.58(s, 2H), 3.55-3.48(m, 4H), 3.29-3.20(m, 1H), 3.18(dd, J=10.5 Hz, J=13.3 Hz, 1H), 2.53-2.40(m, 4H), 2.11(s, 3H)

FORMULATION EXAMPLES

Formulation Example 1

Tablet (Direct Pressing)

An active ingredient 5.0 mg was sieved, and then mixed with lactose 14.1 mg, crospovidone USNF 0.8 mg, and magnesium stearate 0.1 mg, followed by pressing, to formulate a tablet.

Formulation Example 2

Tablet (Wet Formulation)

An active ingredient 5.0 mg was sieved, and then mixed with lactose 16.0 mg and starch 4.0 mg. After polysolvate 80 (0.3 mg) was dissolved in pure water, an appropriate amount of this solution was added, and then atomized. After drying, fine granules were sieved, and then mixed with silicon dioxide 2.7 mg and magnesium stearate 2.0 mg. The fine grains were pressed to be formulated into a tablet.

Formulation Example 3

Powder and Capsule

An active ingredient 5.0 mg was sieved, and then mixed with lactose 14.8 mg, polyvinyl pyrrolidone 10.0 mg, and magnesium stearate 0.2 mg. The mixture was filled into a No. 5 hard gelatin capsule using a suitable apparatus.

Formulation Example 4

Injection Solution

An injection was formulated by containing, in addition to an active ingredient 100 mg, mannitol 180 mg, Na$_2$HPO$_4$2H$_2$O 26 mg, and distilled water 2974 mg.

TEST EXAMPLES

Test Example 1 c-Met Kinase Inhibitory Activity

In order to determine abnormal cell proliferation inhibitory activity of the triazolopyrazine derivatives or pharmaceutically acceptable salts thereof according to the present invention at a cellular stage, the following test was conducted.

The c-Met kinase inhibitory activity was analyzed using dissociation enhanced lanthanide fluoro-immunoassay (DELFIA, Perkin Elmer), which is a kind of time-resolved fluorescence (TRF). 10 mL of the compound prepared in the present invention, as a test compound, was put in a Greiner 96-well V-shaped bottom plate, and a tyrosin kinase buffer (20 mL) mixed with a c-Met enzyme was added thereto, and then the enzyme and the test compound were stirred for 15 minutes, followed by culturing. An ATP solution (10 mL) was added thereto to proceed with a kinase reaction at room temperature for 30 minutes, and then a 50 mM ethylene diamine acetic acid solution (EDTA, 40 mL) was added to stop the reaction. After that, the reaction mixture was transferred to a plate coated with Streptavidin, followed by culturing under shaking. After 2 hours, the cultured material was washed three times with a PBS-T buffer (PBS 0.05% Tween 20).

The europium-labeled anti-phosphotyrosine antibody was diluted to 1:2,500, and 100 mL of the diluent was added per well, followed by culturing under shaking. After 1 hour, the cultured material was washed three times with a PBS-T buffer (PBS 0.05% Tween 20). 100 mL of an enhancement solution was added, followed by shaking culturing for 5 minutes, and then the reaction material was read out within a wavelength range of 615/665 nm using a Wallac Envision 2103 device. The $IC_{50}$ value of the test compound was determined by two sets of data, and obtained using Prism (version 5.01, Graphpad) software.

The $IC_{50}$ values of the compounds at which the c-Met kinase activity is reduced to 50% were tabulated in table 1.

TABLE 1 c-Met $IC_{50}$ (μM) value of each compound

| Compound | c-Met $IC_{50}$ (μM) |
|---|---|
| Chemical formula 4 | 0.011 |
| Chemical formula 5 | 0.029 |
| Chemical formula 6 | 0.002 |
| Chemical formula 7 | 0.006 |
| Chemical formula 8 | 0.004 |
| Chemical formula 9 | 0.003 |
| Chemical formula 10 | 0.004 |
| Chemical formula 11 | 0.003 |
| Chemical formula 12 | 0.004 |
| Chemical formula 13 | 0.015 |
| Chemical formula 14 | 0.014 |
| Chemical formula 15 | 0.006 |
| Chemical formula 17 | 0.003 |
| Chemical formula 18 | 0.005 |
| Chemical formula 19 | 0.007 |
| Chemical formula 20 | 0.002 |
| Chemical formula 21 | 0.005 |
| Chemical formula 22 | 0.004 |
| Chemical formula 23 | 0.003 |
| Chemical formula 24 | 0.002 |
| Chemical formula 25 | 0.005 |
| Chemical formula 26 | 0.005 |
| Chemical formula 27 | 0.005 |
| Chemical formula 28 | 0.004 |
| Chemical formula 29 | 0.002 |
| Chemical formula 30 | 0.002 |
| Chemical formula 31 | 0.002 |
| Chemical formula 32 | 0.001 |
| Chemical formula 33 | 0.003 |
| Chemical formula 34 | 0.003 |

TABLE 1-continued c-Met $IC_{50}$ (μM) value of each compound

| Compound | c-Met $IC_{50}$ (μM) |
|---|---|
| Chemical formula 35 | 0.003 |
| Chemical formula 36 | 0.002 |
| Chemical formula 37 | 0.002 |
| Chemical formula 38 | 0.003 |
| Chemical formula 39 | 0.002 |
| Chemical formula 40 | 0.002 |
| Chemical formula 42 | 0.004 |
| Chemical formula 45 | 0.008 |
| Chemical formula 46 | 0.007 |
| Chemical formula 47 | 0.013 |
| Chemical formula 48 | 0.006 |
| Chemical formula 49 | 0.008 |

Most novel compounds showed $IC_{50}$ values of 0.01 μM or less, and thus have very excellent in vitro activities on c-Met. Hence, it can be seen that the novel triazolopyrazine derivatives or pharmaceutically acceptable salts thereof according to the present invention have an excellent c-Met kinase inhibitory effect.

Test example 2

Cancer Cell Proliferation Inhibitory Test

In order to determine the cancer cell proliferation inhibitory activity of the triazolopyrazine derivatives or pharmaceutically acceptable salts thereof according to the present invention, the following test was conducted.

<2-1> Materials

RPMI 1640 cell culture medium, fetal bovine serum (FBS), and trypsin were purchased from Gibco (Grand Island, N.Y.), and Sigma Chemical products of sodium hydrogen carbonate, amphotericin B, and gentamicin were used. In addition, reagents, such as sulforhodamine B (SRB), Trisma base, and trichloroactic acid (TCA), were purchased from Sigma Chemical Co. For the MTS analysis, CellTiter 96® AQueous Non-Radioactive Cell Proliferation Assay was purchased from Promega Co. In addition, for the cell culture, products from Palcon co. (Lincoln Park, N.J.) were used for T-25 culture flask, 96-well plates, and other disposable glassware and vial necessary for cell culture.

As an Elizar reader (microplate reader) for cytotoxicity measurement, E-max or SpectraMax250 from Molecular Devices Co. (Sunnyvale, Calif.) was used.

<2-2> Method

The drug used in the test was diluted to a desired concentration as a test medium, and the final concentration of dimethyl sulfoxide was 0.5% or less.

All the cancer cell lines used in the test originated from the human body, and gastric cancer cell lines Hs746T and MKN-45 were used. Culturing was conducted in a 5% carbon dioxide incubator at 37° C. using RPMI 1640 medium containing with 10% fetal bovine serum (FBS), and sub-culturing continued every 3-4 days.

$5\times10^3$ cells of Hs746T were dispensed to each well of the 96-well flat bottom micro-plate. MKN-45 was dispensed at $1\times10^4$ cells. The cells were cultured for 24 hours, so that the cells adhered to the bottom, and then the culture liquid was removed. The culture liquid containing each of the compounds of the present invention was added, followed by culturing for 72 hours. After the culturing with the compound was completed, the cytotoxicity was measured using protein stain reagent SRB or MTS assay.

Specifically, after the culturing with the compound of the present invention was completed, the cultured liquid was removed. Each well was treated with a cool TCA solution, and allowed to stand at 4° C. for 1 hour to fix cells. The TCA solution was removed, followed by drying at room temperature, and then a stain solution containing 0.4% SRB dissolved in 1% acetic acid solution was added, and then the mixture was allowed to stand for 30 minutes to stain cells. Extra SRB unbinding with cells was removed by washing with a 1% acetic acid solution, and 10 mM trisma base (unbuffered) of pH 10.3-10.5 was added to the stained cells to elute SRB. The absorbance of each well was measured at a wavelength range of 520 nm using an Eliza reader (micro-plate reader).

The drug cytotoxicity was measured from the OD values for the well added without the drug (C), each well added with the drug (T), and the well initially added with the drug (Tz):

$$[(T-Tz)/(C-Tz)]\times100 \text{ for } Tz=T; \text{ or}$$

$$[(T-Tz)/(Tz)]\times100 \text{ for } Tz>T.$$

The cancer cell inhibitory activity measurement using MTS assay was conducted as follows. Specifically, after the culturing with the compound of the present invention was completed, the PMS solution and MTS solution constituting the CellTiter 96® AQueous Non-Radioactive Cell Proliferation Assay product from Promega Co. were mixed, and 20 µL was put into each well. After the cells were placed in an incubator for 4 hours, and then taken out and allowed to stand at room temperature for 10 minutes. The absorbance at 490 nM was measured using SpectraMax250 from Molecular Devices Co., and then $IC_{50}$ value was calculated.

The $IC_{50}$ values of the compounds at which the cancer cell (Hs746T) proliferation is inhibited to 50% were tabulated in table 2.

TABLE 2

Cancer cell (Hs746T) proliferation inhibition of each compound [$IC_{50}$ (µM)]

| Compound | Hs746T $IC_{50}$ (µM) |
| --- | --- |
| Chemical formula 4 | 0.0012 |
| Chemical formula 5 | 0.0013 |
| Chemical formula 6 | 0.00017 |
| Chemical formula 7 | 0.00011 |
| Chemical formula 8 | 0.00014 |
| Chemical formula 9 | 0.00095 |
| Chemical formula 10 | 0.0011 |
| Chemical formula 11 | 0.00093 |
| Chemical formula 12 | 0.00096 |
| Chemical formula 13 | 0.00086 |
| Chemical formula 14 | 0.0041 |
| Chemical formula 16 | 0.0021 |
| Chemical formula 17 | 0.00012 |
| Chemical formula 18 | 0.0096 |
| Chemical formula 19 | 0.0012 |
| Chemical formula 20 | 0.0020 |
| Chemical formula 21 | 0.0056 |
| Chemical formula 22 | 0.0098 |
| Chemical formula 23 | 0.0001 |
| Chemical formula 24 | 0.00008 |
| Chemical formula 25 | 0.0011 |
| Chemical formula 26 | 0.0009 |
| Chemical formula 27 | 0.0007 |
| Chemical formula 28 | 0.0007 |
| Chemical formula 29 | 0.0001 |
| Chemical formula 30 | 0.00011 |
| Chemical formula 31 | 0.00018 |
| Chemical formula 32 | 0.00014 |
| Chemical formula 33 | 0.0095 |
| Chemical formula 34 | 0.015 |
| Chemical formula 35 | 0.002 |
| Chemical formula 36 | 0.0038 |
| Chemical formula 37 | 0.0013 |
| Chemical formula 38 | 0.00014 |

As shown in table 2, the $IC_{50}$ values of all the compounds on cancer cells Hs746T showed to be 0.01 μM or less. Especially, the compounds of chemical formulas 6 to 9, 11 to 13, 17, 23, 24, 26 to 32, and 38 showed very low $IC_{50}$ values of 0.001 μM or less. Hence, it can be seen that the novel triazolopyrazine derivatives or pharmaceutically acceptable salts thereof according to the present invention have a very excellent effect of inhibiting the proliferation of cancer cells or the like.

Preparative examples for the composition of the present invention are exemplified as follows.

Preparative Example 1

Preparation of Pharmaceutical Preparation

<1-1> Preparation of Powder

| Triazolopyrazine derivative 2 g |
| Lactose 1 g |

The above ingredients were mixed, and then filled in a sealed package, thereby preparing a powder.

<1-2> Preparation of Tablet

| Triazolopyrazine derivative 100 mg |
| Corn starch 100 mg |
| Lactose 100 mg |
| Magnesium stearate 2 mg |

The above ingredients were mixed, and then tabulated by the general tablet preparation method, thereby preparing a tablet.

<1-3> Preparation of Capsule

| Triazolopyrazine derivative 100 mg |
| Corn starch 100 mg |
| Lactose 100 mg |
| Magnesium stearate 2 mg |

The above ingredients were mixed, and then filled in a gelatin capsule by the general capsule preparation method, thereby preparing a capsule.

<1-4> Preparation of Injection Solution

| Triazolopyrazine derivative 10 μg/ml |
| Dilute hydrochloric acid BP until pH 3.5 |
| Injectable sodium chloride BP maximum 1 ml |

The triazolopyrazine derivative according to the present invention was dissolved in an appropriate volume of injectable sodium chloride BP, and the pH of the resultant solution was adjusted to 3.5 by using diluted hydrochloric acid BP. Then the volume of the solution was adjusted by using injectable sodium chloride BP, and the solution was thoroughly mixed. The resulting solution was filled into a 5 ml type I ampoule made of transparent glass, and the glass was melted to seal the ampoule under the upper grid of air. The ampoule was sterilized by autoclaving at 120° C. for 15 minutes or more, to give an injection solution.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A triazolopyrazine derivative represented by chemical formula 1:

Chemical formula 1

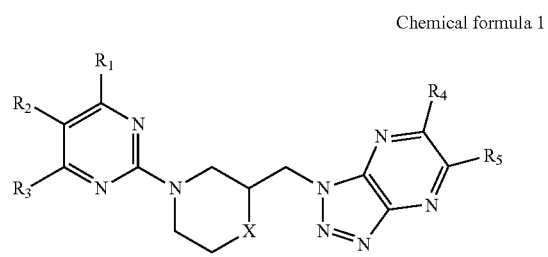

or a pharmaceutically acceptable salt thereof, wherein:

$R_1$ to $R_3$ are each independently hydrogen, halogen, 5- to 6-membered heterocycloalkyl, 5- to 6-membered heterocycloalkenyl, $C_1$-C3 alkoxy substituted with 5- to 6-membered heterocycloalkyl, $C_1$-$C_5$ alkyl substituted with 5- to 6-membered heterocycloalkyl, $C_1$-$C_3$ alkoxy substituted with 5- to 6-membered heterocycloalkyl, phenyl substituted with halogen, acetyl piperazine, or piperazinyl carbonyl, or 5- to 6-membered heteroaryl substituted with 5- to 6-membered heterocycloalkyl, hydroxy $C_1$-$C_5$ alkyl, or $C_1$-$C_5$ alkyl;

wherein at least one of $R_1$ to $R_3$ is not hydrogen;

$R_4$ and $R_5$ are each independently hydrogen, 5- to 6-membered heteroaryl unsubstituted or substituted with $C_1$-$C_5$ alkyl, or phenyl substituted with cyano, halogen, or $C_1$-$C_5$ alkyl; wherein at least one of $R_4$ and $R_5$ is not hydrogen; and X is oxygen or carbon.

2. The triazolopyrazine derivative of claim 1, or a pharmaceutically acceptable salt thereof, wherein $R_1$ to $R_3$ are each independently hydrogen; halogen; pyrazole substituted with methyl, hydroxy ethyl, piperidine, or N-methyl piperidine; tetrahydropyridine unsubstituted or substituted with methyl or hydroxy ethyl; phenyl substituted with halogen, morpholinoethoxy, piperazinylethoxy, piperazinylmethyl, morpholinomethyl, acetyl piperazine, or piperazinyl carbonyl; morpholinoethoxy; piperazinylethoxy; or piperidine unsubstituted or substituted with methyl or hydroxy ethyl, wherein two of $R_1$ to $R_3$ are hydrogen.

3. The triazolopyrazine derivative of claim 1, or a pharmaceutically acceptable salt thereof, wherein $R_4$ and $R_5$ are each independently hydrogen; N-methyl pyrazole; or phenyl substituted with cyano or halogen, wherein one of $R_4$ and $R_5$ is hydrogen.

4. A triazolopyrazine derivative, or a pharmaceutically acceptable salt thereof, wherein the triazolopyrazine derivative is selected from the group consisting of compounds represented by chemical formulas 2 to 50 below:

Chemical formula 2
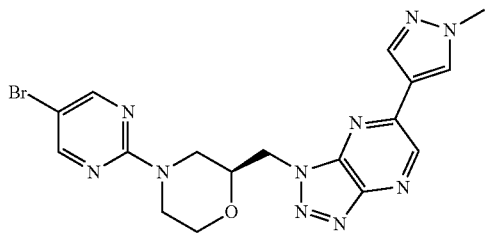
Chemical formula 3
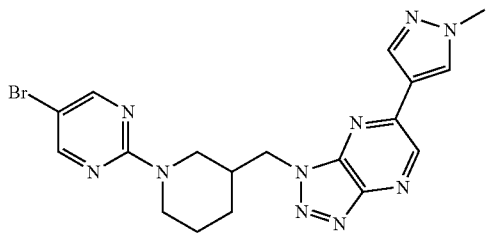
Chemical formula 4
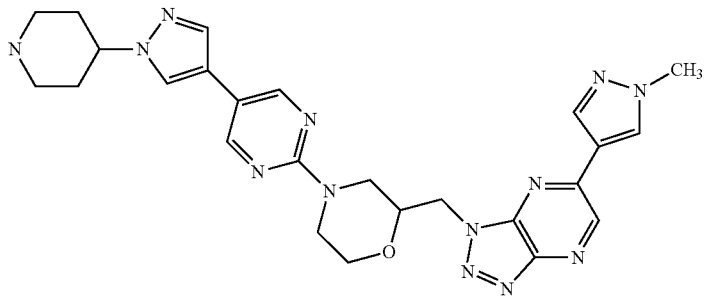
Chemical formula 5
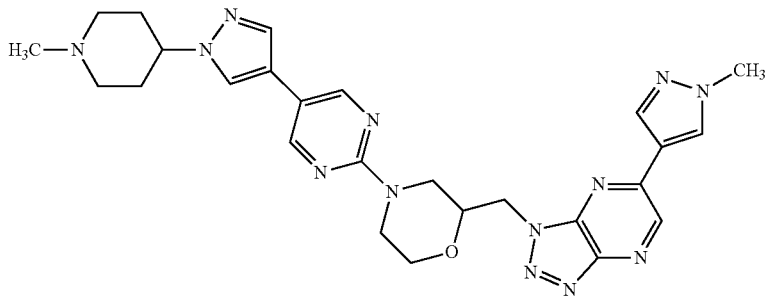
Chemical formula 6
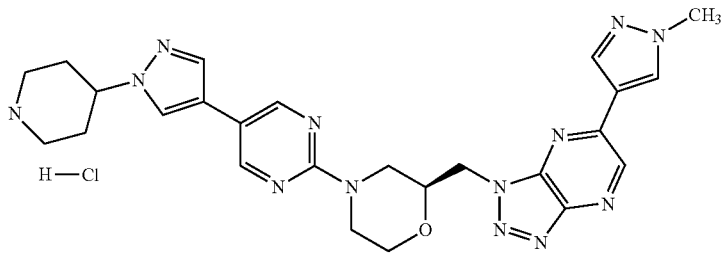
Chemical formula 7
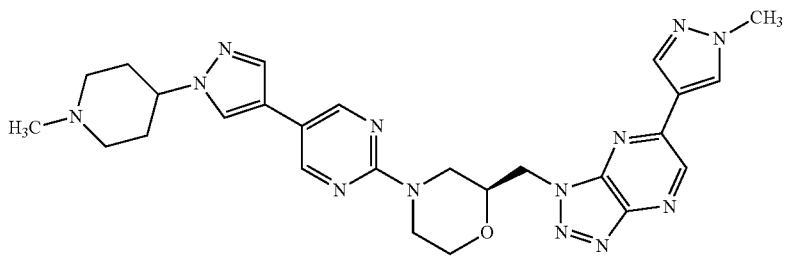
Chemical formula 8
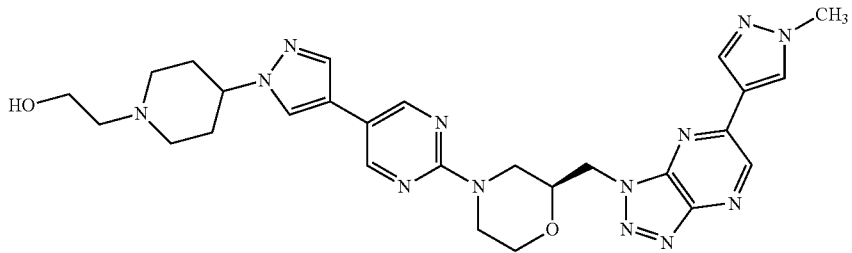

-continued
Chemical formula 9
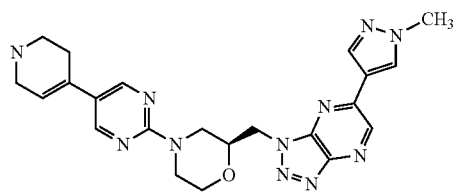
Chemical formula 10
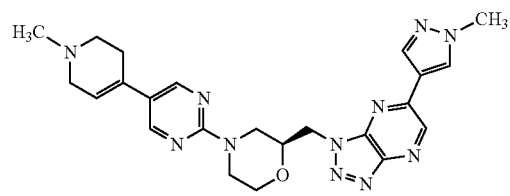
Chemical formula 11
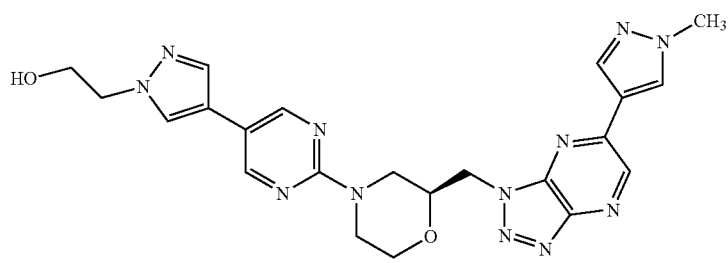
Chemical formula 12
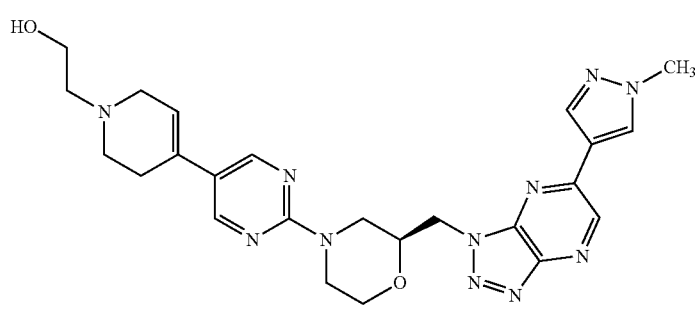
Chemical formula 13
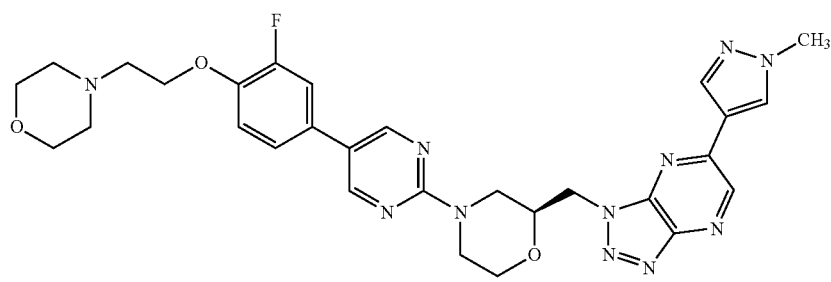
Chemical formula 14
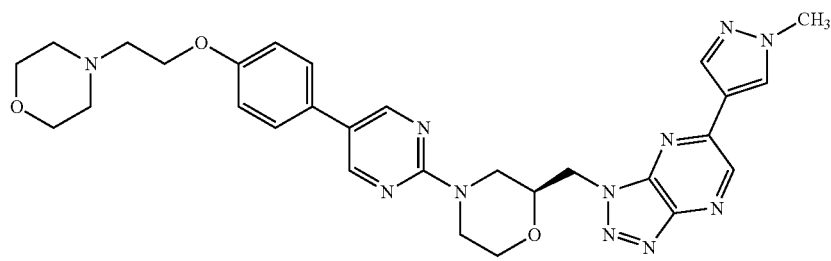
Chemical formula 15
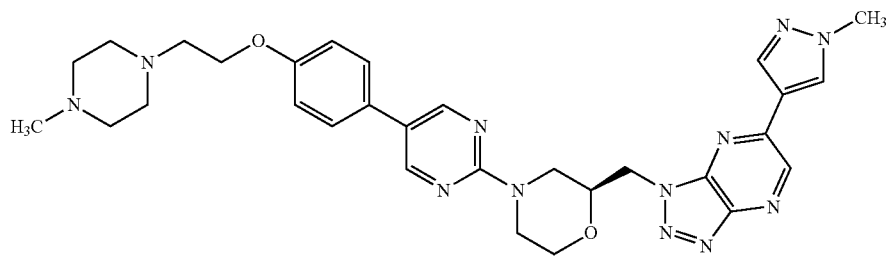

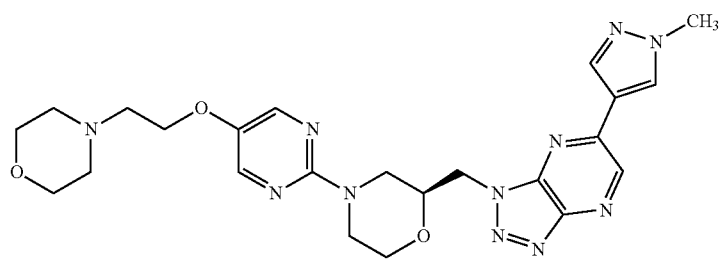
Chemical formula 16
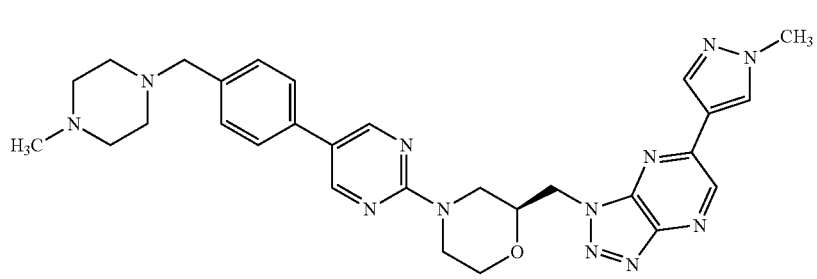
Chemical formula 17
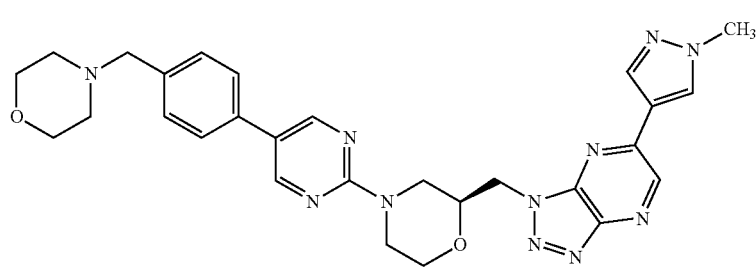
Chemical formula 18
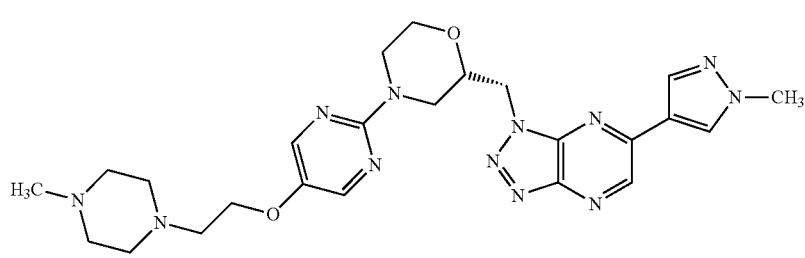
Chemical formula 19
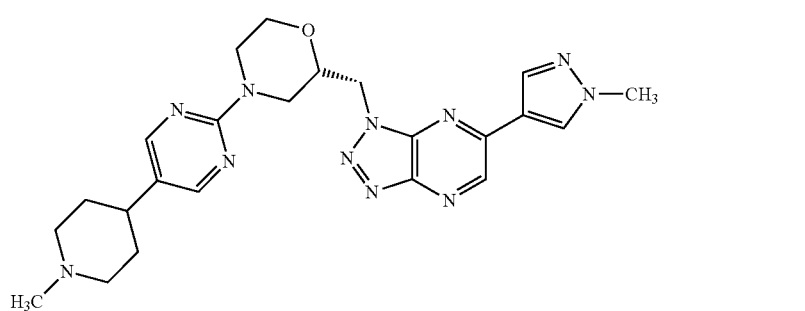
Chemical formula 20

Chemical formula 21
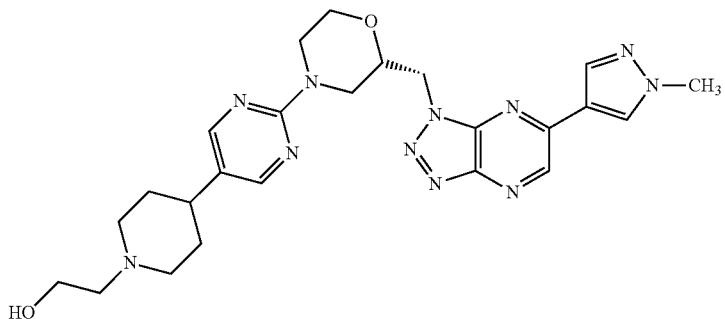
Chemical formula 22
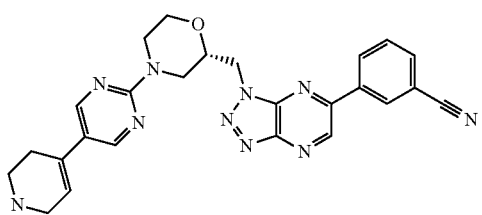
Chemical formula 23
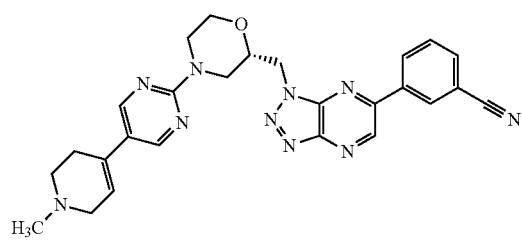
Chemical formula 24
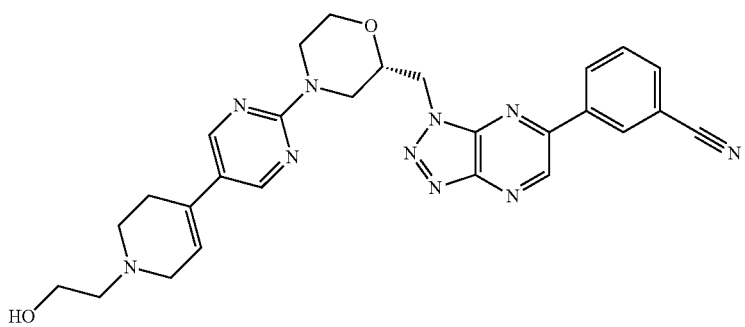
Chemical formula 25
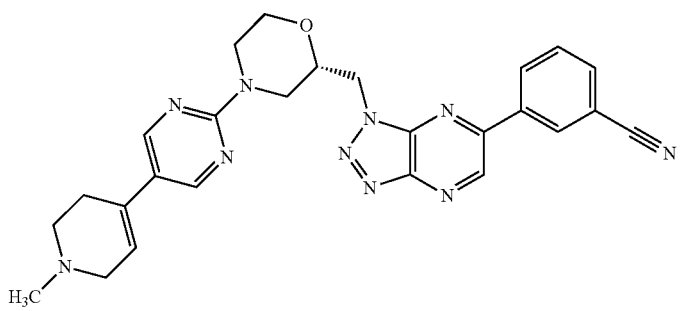
Chemical formula 26
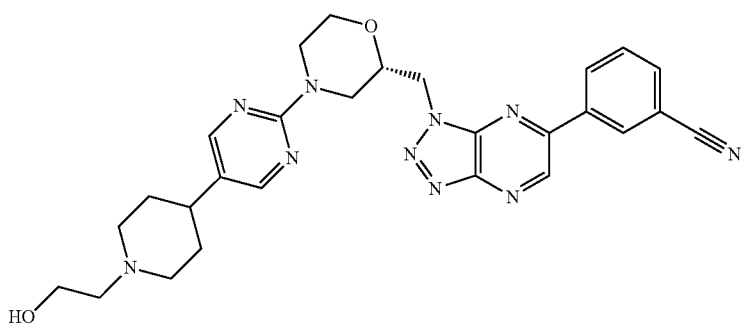

-continued
Chemical formula 27
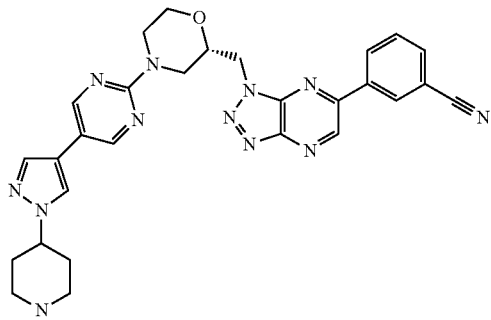
Chemical formula 28
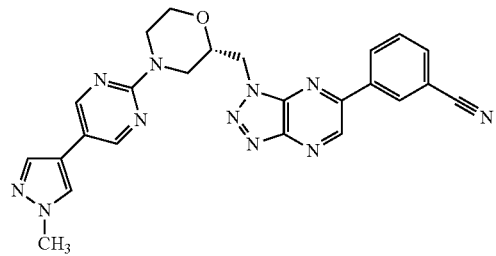
Chemical formula 29
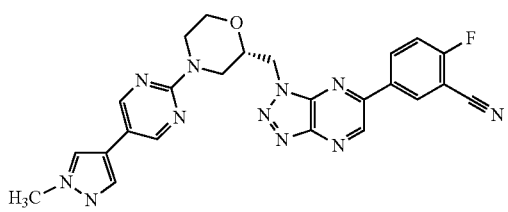
Chemical formula 30
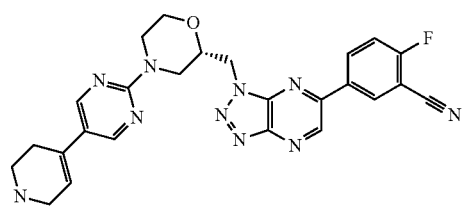
Chemical formula 31
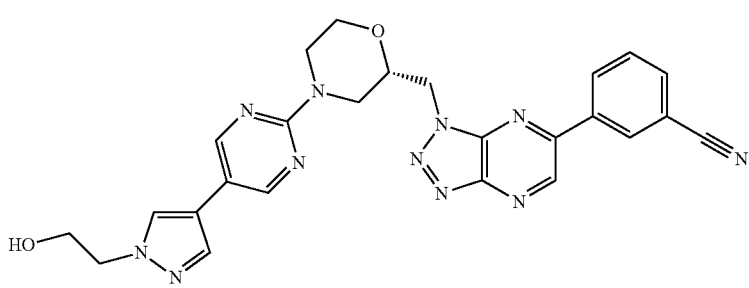
Chemical formula 32
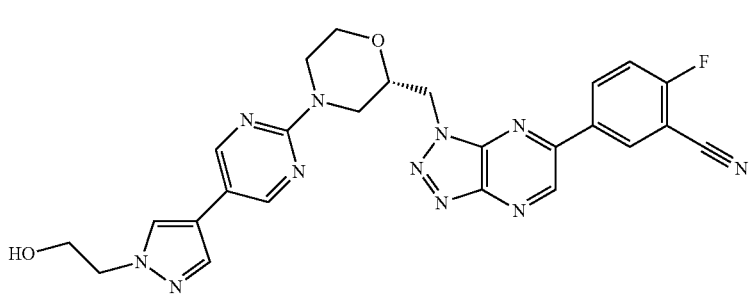
Chemical formula 33
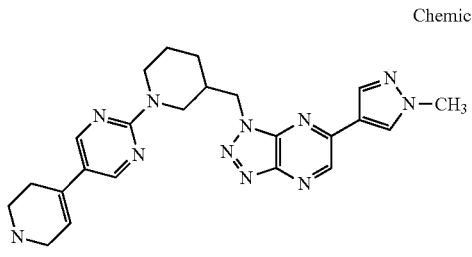
Chemical formula 34
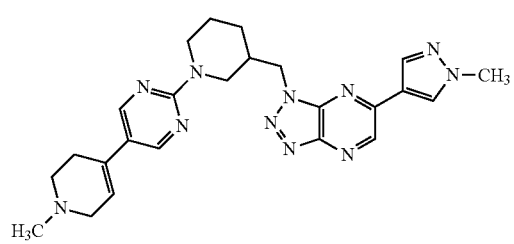

-continued
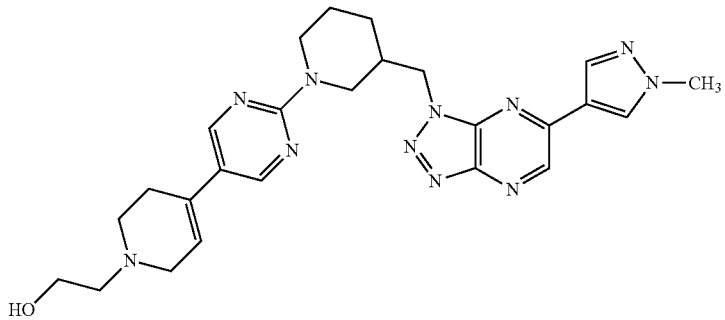
Chemical formula 35
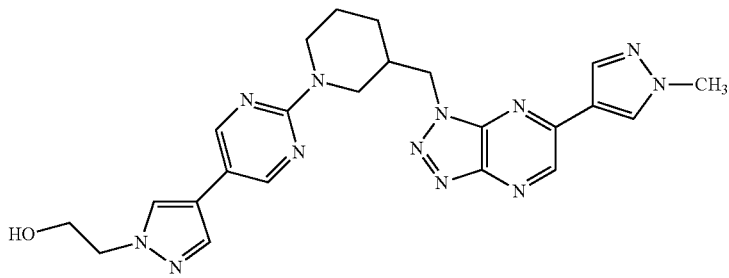
Chemical formula 36
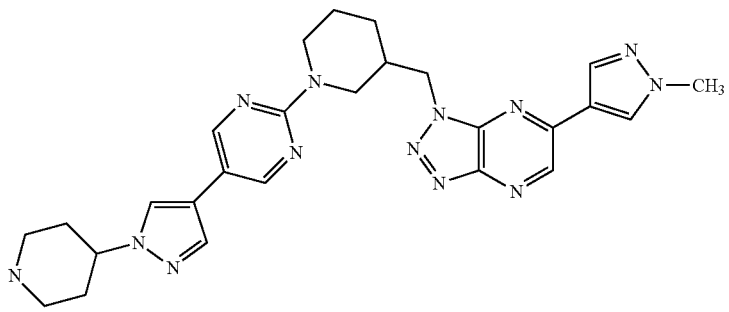
Chemical formula 37
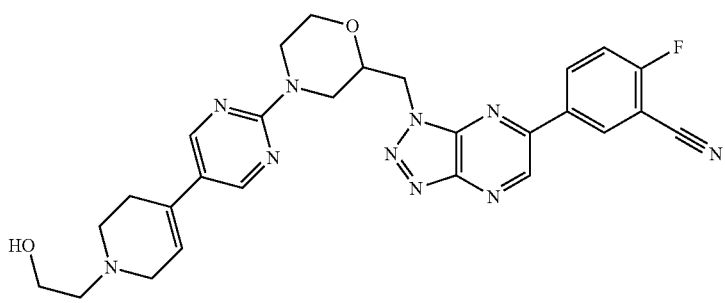
Chemical formula 38
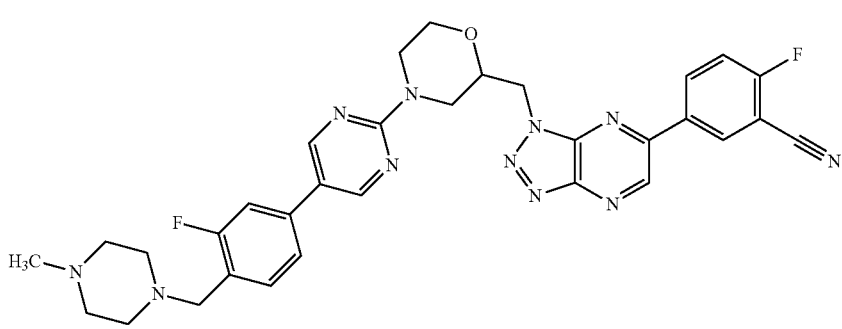
Chemical formula 39

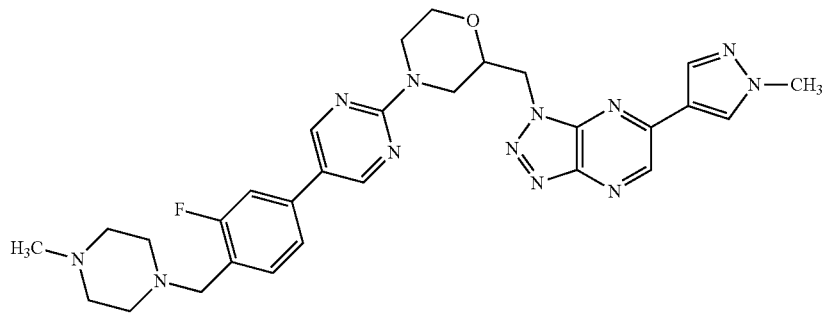
Chemical formula 40
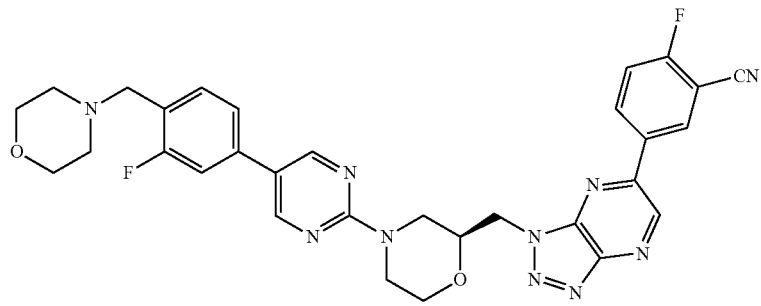
Chemical formula 41
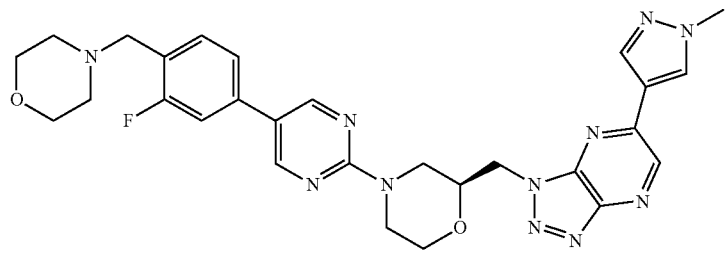
Chemical formula 42
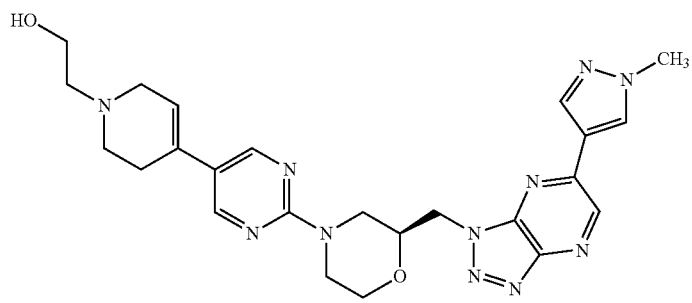
Chemical formula 43
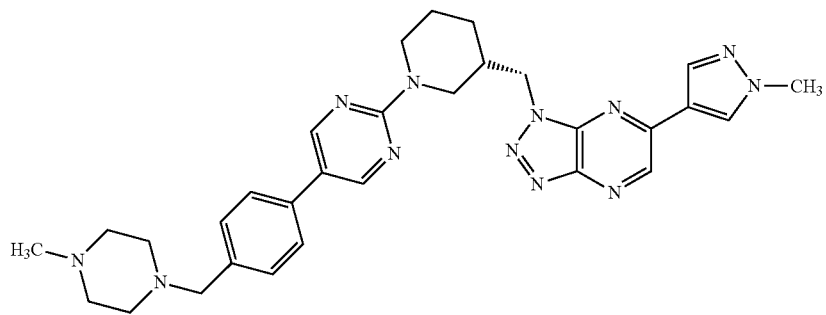
Chemical formula 44

-continued
Chemical formula 45
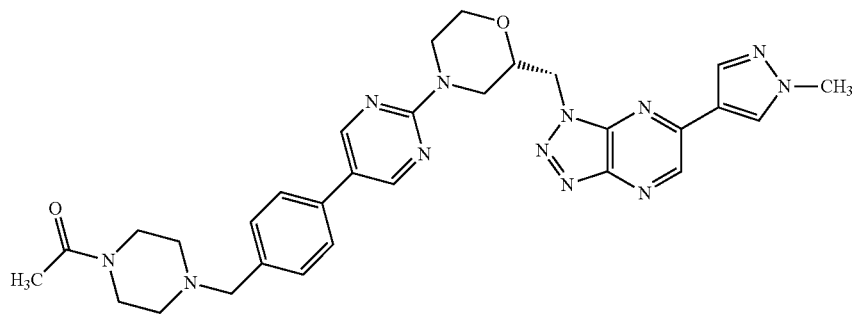
Chemical formula 46
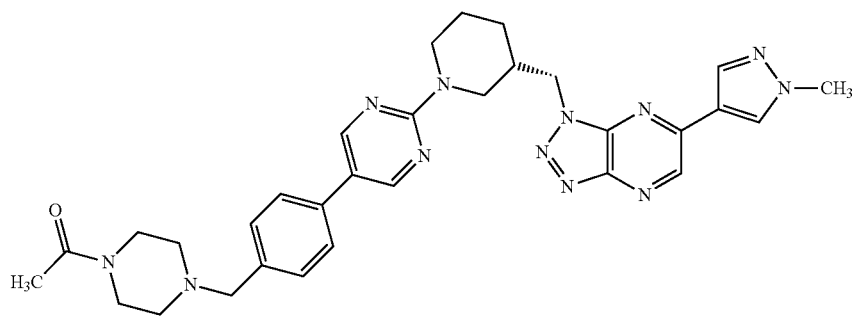
Chemical formula 47
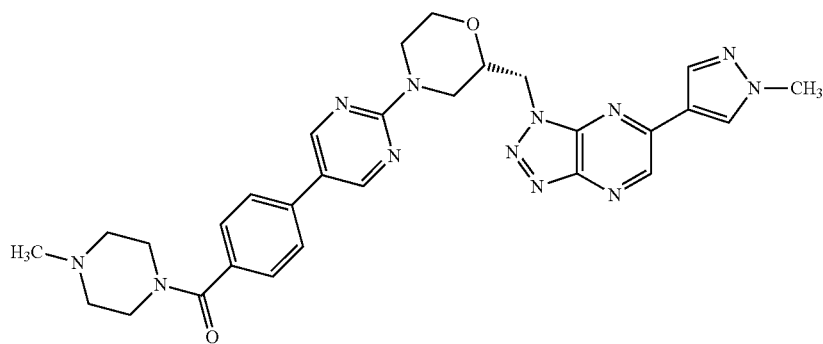
Chemical formula 48
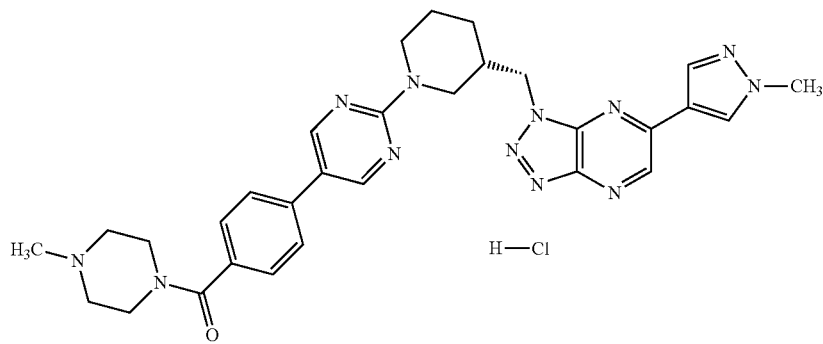
Chemical formula 49
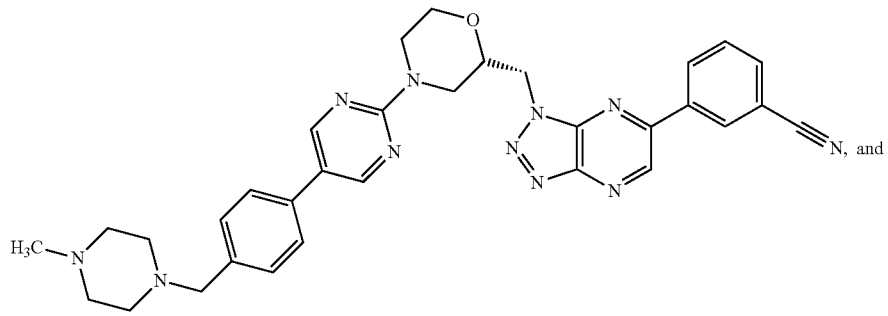

-continued

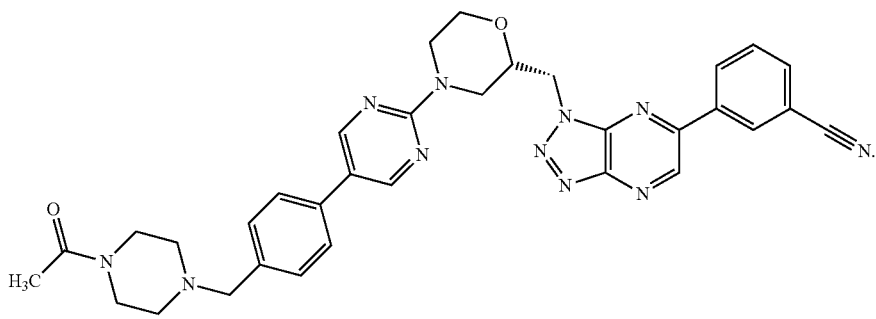

Chemical formula 50

5. The triazolopyrazine derivative of claim 4, or a pharmaceutically acceptable salt thereof, wherein the triazolopyrazine derivative is selected from the group consisting of compounds represented by chemical formulas 6 to 9, 11 to 13, 17, 23, 24, 26 to 32, and 38.

6. A pharmaceutical composition containing, the triazolopyrazine derivative of claim 1, or a pharmaceutically acceptable salt or solvate thereof.

7. A method for treating gastric cancer, the method comprising administering the triazolopyrazine derivative of claim 1, or a pharmaceutically acceptable salt or solvate thereof.

8. The triazolopyrazine derivative of claim 4, wherein the triazolopyrazine derivative is a compound represented by chemical formula 7, or a pharmaceutically acceptable salt thereof.

9. The triazolopyrazine derivative of claim 4, wherein the triazolopyrazine derivative is a compound represented by chemical formula 8, or a pharmaceutically acceptable salt thereof.

10. The triazolopyrazine derivative of claim 4, wherein the triazolopyrazine derivative is a compound represented by chemical formula 17, or a pharmaceutically acceptable salt thereof.

11. The triazolopyrazine derivative of claim 4, wherein the triazolopyrazine derivative is a compound represented by chemical formula 23, or a pharmaceutically acceptable salt thereof.

12. The triazolopyrazine derivative of claim 4, wherein the triazolopyrazine derivative is a compound represented by chemical formula 24, or a pharmaceutically acceptable salt thereof.

13. The triazolopyrazine derivative of claim 4, wherein the triazolopyrazine derivative is a compound represented by chemical formula 29, or a pharmaceutically acceptable salt thereof.

14. The triazolopyrazine derivative of claim 4, wherein the triazolopyrazine derivative is a compound represented by chemical formula 30, or a pharmaceutically acceptable salt thereof.

15. The triazolopyrazine derivative of claim 4, wherein the triazolopyrazine derivative is a compound represented by chemical formula 32, or a pharmaceutically acceptable salt thereof.

16. The triazolopyrazine derivative of claim 4, wherein the triazolopyrazine derivative is a compound represented by chemical formula 38, or a pharmaceutically acceptable salt thereof.

* * * * *